United States Patent [19]

Kawamoto et al.

[11] Patent Number: 5,310,735

[45] Date of Patent: May 10, 1994

[54] CARBAPENEM DERIVATIVES HAVING ANTIBIOTIC ACTIVITY, THEIR PREPARATION AND THEIR USE

[75] Inventors: Isao Kawamoto; Masao Miyauchi; Eiji Nakayama; Rokuro Endo; Satoshi Ohya; Yukio Utsui, all of Tokyo, Japan

[73] Assignee: Sankyo Company, Limited, Tokyo, Japan

[21] Appl. No.: 938,483

[22] Filed: Aug. 31, 1992

Related U.S. Application Data

[63] Continuation of Ser. No. 658,975, Feb. 21, 1991, abandoned.

[30] Foreign Application Priority Data

Feb. 23, 1990 [JP] Japan ................................. 2-42796
Aug. 10, 1990 [JP] Japan ................................ 2-212283

[51] Int. Cl.$^5$ .................. A01N 43/00; A61K 31/395; C07D 487/04
[52] U.S. Cl. ...................................... 514/210; 540/350
[58] Field of Search ........................ 540/350; 514/210

[56] References Cited

U.S. PATENT DOCUMENTS 3,950,357 4/1976 Kahan et al. .
4,194,047 3/1980 Kahan et al. .
4,552,873 11/1985 Miyadera et al. .
4,771,046 9/1988 Kawamoto et al. .
5,227,376 7/1993 Sunagawa et al. .............. 514/210

FOREIGN PATENT DOCUMENTS 0126587 11/1984 European Pat. Off. .
0242134 10/1987 European Pat. Off. .
0333175  9/1989 European Pat. Off. .
0442497  8/1991 European Pat. Off. .

OTHER PUBLICATIONS

Kim et al, *J Med Chem*, 1989, 32, 601–604.

*Primary Examiner*—Marianne M. Cintins
*Assistant Examiner*—Rebecca Cook
*Attorney, Agent, or Firm*—Frishauf, Holtz, Goodman & Woodward

[57] ABSTRACT

Carbapenem compounds of formula (I):

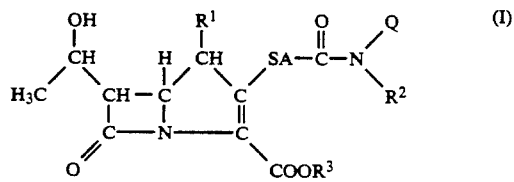

in which: A is a fully saturated heterocyclic group, of which at least one ring atom is nitrogen; $R^1$ is hydrogen or methyl; $R^2$ is hydrogen or alkyl; $R^3$ is hydrogen or a negative ion; Q is: (i) —B—N$^+$R$^8$R$^9$R$^{10}$, where R$^8$, R$^9$ and R$^{10}$ are alkenyl, alkynyl or optionally substituted alkyl, and B is alkylene or alkylidene.

12 Claims, No Drawings

CARBAPENEM DERIVATIVES HAVING ANTIBIOTIC ACTIVITY, THEIR PREPARATION AND THEIR USE

This application is a continuation of application Ser. No. 07/658,975, filed Feb. 21, 1991, now abandoned.

BACKGROUND TO THE INVENTION

The present invention relates to a series of novel carbapenem derivatives, and provides methods and compositions using these for the treatment and prevention of bacterial infections; it also provides processes for their preparation.

The class of $\beta$-lactam antibiotics includes the well known penicillins and cephalosporins, as well as the more recently introduced carbapenem compounds, of which the most successful member to date is imipenem (a derivative of the well known thienamycin), which is one of the isomers of 2-{2-[(iminomethyl)amino]ethyl-thio}-6-(1-hydroxyethyl)-1-carbapen-2-em-3-carboxylic acid. In this specification, as is common in this field, the carbapenem derivatives, including those of the present invention, are named as derivatives of the notional 1-carbapen-2-em:

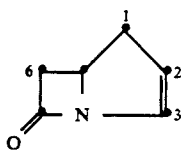

As can be seen from the above formula, the 1-carbapen-2-em system resembles the basic penicillin nucleus, except that there is a carbon atom (replacing a sulfur atom) at the 1-position. The carbapenem compounds also normally have substituents at the 2-, 3- and 6-positions. The substituent at the 6-position is most commonly, as in imipenem and thienamycin, a 1-hydroxyethyl group. These carbapenem compounds have a carbon-carbon double bond between the 2- and 3-positions.

In general, although thienamycin derivatives have been found to have excellent antibacterial activity, it has been reported that inactivation occurs in the human body as a result of decomposition of the compound due to the action of dehydropeptidase I; this is shown experimentally by a poor urinary recovery [H. Kropp et al: Antimicrob. Agents Chemother., 22, 62 (1982); S. R. Norrby et al.: ibid., 23, 300 (1983)]. As a consequence, the known thienamycin derivatives are of limited practical use. Although imipenem has been used clinically in combination with another compound, cilastatin, to protect it against this degradation, it is clearly undesirable to administer two or more drugs where one would suffice, and the restricted stability of the thienamycin derivatives has thus severely limited their use.

In recent years, many carbapenem derivatives have been disclosed for potential use as antibiotics, these generally differing in the nature of the substituent at the 2-position on the carbapenem nucleus. For example, European Patent Publications No. 126 587 and 333 175, which are believed to represent the closest prior art to the present invention of which we are presently aware, both disclose 1-carbapen-2-em-3-carboxylic acid derivatives having, like some of the compounds of the present invention, a substituted pyrrolidin -3-ylthio substituent at the 2-position. The compounds of the present invention differ from those of the prior art in possessing a quaternary nitrogen atom, and it appears that this results in a significant and unexpected increase in antimicrobial, especially antibacterial, activity as well as a much improved stability in the mammalian body, as demonstrated by improved urinary recovery. When comparing compounds of the type generally disclosed in the prior art with precisely equivalent compounds in which the nitrogen atom has been quaternised in accordance with the present invention, we have found a consistent improvement in urinary recovery in the compounds of the present invention as compared with the prior compounds. This activity is accompanied by a low toxicity, enabling the compounds to be used in therapy.

The compounds of the present invention are therefore expected to be of considerable value in the treatment and prophylaxis of microbial infections in mammals, especially humans.

BRIEF SUMMARY OF INVENTION

In accordance with the present invention there are provided novel 1-carbapen-2-em-3carboxylic acid derivatives, which are those compounds of formula (I):

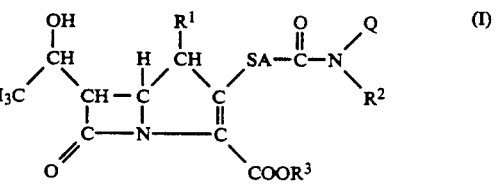

in which:

A represents a fully saturated heterocyclic group having from 4 to 6 ring atoms, said nitrogen atom and the remainder are carbon atoms, said nitrogen atom having on its remaining valence a group or atom $R^4$, wherein:

$R^4$ represents: a hydrogen atom; an alkenyl group having from 2 to 5 carbon atoms; an alkynyl group having from 2 to 5 carbon atoms; an alkyl group having from 1 to 6 carbon atoms; a substituted alkyl group having from 1 to 6 carbon atoms and having at least one substituent selected from the group consisting of substituents (a), defined below; or a group of formula $—C(=NH)R^5$, wherein $R^5$ represents a hydrogen atom or an alkyl group having from 1 to 6 carbon atoms;

$R^1$ represents a hydrogen atom or a methyl group;

$R^2$ represents a hydrogen atom or an alkyl group having from 1 to 6 carbon atoms;

$R^3$ represents a hydrogen atom or a negative ionic charge;

Q represents:

(i) a group of formula $—B—N^+R^8R^9R^{10}$, wherein: $R^8$, $R^9$ and $R^{10}$ are independently selected from the group consisting of alkenyl groups having from 2 to 5 carbon atoms, alkynyl groups having from 2 to 5 carbon atoms, alkyl groups having from 1 to 6 carbon atoms and substituted alkyl groups which have from 1 to 6 carbon atoms and which have at least one substituent selected from the group consisting of substituents (b), defined below; and B represents an alkylene or alkylidene group having from 1 to 4 carbon atoms;

(ii) a heterocyclic group having from 4 to 10 ring atoms in a single or bridged ring, one of said ring atoms being a quaternary nitrogen atom of formula $>N^+R^{11}R^{12}$, wherein:

$R^{11}$ and $R^{12}$ are independently selected from the group consisting of alkenyl groups having from 2 to 5 carbon atoms, alkynyl groups having from 2 to 5 carbon atoms, alkyl groups having from 1 to 6 carbon atoms and substituted alkyl groups having from 1 to 6 carbon atoms and having at least one substituent selected from the group consisting of substituents (b), defined below; and 0, 1 or 2 of said ring atoms being selected from the group consisting of nitrogen, oxygen and sulfur heteroatoms, the remainder being carbon atoms, said heterocyclic group being otherwise unsubstituted or having at least one substituent selected from the group consisting of substituents (c), defined below;

(iii) an alkyl group having from 1 to 6 carbon atoms and substituted by a heterocyclic group as defined in (ii) above; or (iv) an alkyl group having from 1 to 6 carbon atoms and substituted by an aromatic heterocyclic group having from 5 to 8 ring atoms, one of said ring atoms being a quaternary nitrogen atom of formula

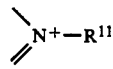

wherein $R^{11}$ is as defined above, and 0, 1 or 2 of said ring atoms being an additional hetero-atom selected from the group consisting of nitrogen, oxygen and sulfur hetero-atoms; or $R^2$ and Q, together with the nitrogen atom to which they are attached, represent a group of formula (II):

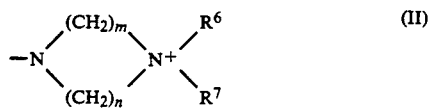

wherein:

m and n are each 1, 2 or 3;

$R^6$ represents an alkyl group having from 1 to 6 carbon atoms or a substituted alkyl group which has from 1 to 6 carbon atoms and which has at least one substituent selected from the group consisting of substituents (a), defined below;

$R^7$ represents an alkenyl group having from 2 to 5 carbon atoms, an alkynyl group having from 2 to 5 carbon atoms, an alkyl group having from 1 to 6 carbon atoms or a substituted alkyl group which has from 1 to 6 carbon atoms and which has at least one substituent selected from the group consisting of substituents (b), defined below;

and the carbon atoms of said group of formula (II) are unsubstituted or they are substituted by at least one substituent selected from the group consisting of alkyl groups having from 1 to 6 carbon atoms and oxygen atoms (to form an oxo group);

substituents (a):

hydroxy groups, carboxy groups, cyano groups, sulfamoyl groups, sulfo groups, halogen atoms, and groups of formula $-NR^aR^b$ or $-CONR^aR^b$, where $R^a$ and $R^b$ are independently selected from the group consisting of hydrogen atoms and alkyl groups having from 1 to 4 carbon atoms;

substituents (b):

hydroxy groups; carboxy groups; groups of formula $-NR^aR^b$, where $R^a$ and $R^b$ are as defined above; groups of formula $-CONR^cR^d$ or $-OCONR^cR^d$, where $R^c$ and $R^d$ are independently selected from the group consisting of hydrogen atoms, alkyl groups having from 1 to 4 carbon atoms and substituted alkyl groups which have from 1 to 4 atoms and which have at least one substituent selected from the group consisting of substituents (d) defined below; cyano groups; sulfamoyl groups; ureido groups; sulfo groups; halogen atoms; alkenyl groups having from 2 to 5 carbon atoms; alkoxy groups having from 1 to 4 carbon atoms; alkoxycarbonyl groups having from 2 to 5 carbon atoms; alkanoyl groups having from 1 to 4 carbon atoms; alkanoylamino groups having from 1 to 4 carbon atoms; alkanoyloxy groups having from 1 to 4 carbon atoms; alkylthio groups having from 1 to 4 carbon atoms; alkylsulfinyl groups having from 1 to 4 carbon atoms and alkylsulfonyl groups having from 1 to 4 carbon atoms;

substituents (c):

hydroxy groups, groups of formula $-CONR^aR^b$, where $R^a$ and $R^b$ are as defined above, alkyl groups having from 1 to 4 carbon atoms and halogen atoms;

substituents (d):

hydroxy groups, carboxy groups and groups of formula $-CONR^aR^b$ or $-OCONR^aR^b$, where $R^a$ and $R^b$ are as defined above; and salts thereof and, where $R^3$ represents a hydrogen atom, esters of said compound, provided that, where where $R^3$ represents a hydrogen atom or an ester, the compound also includes an anion.

The invention also provides a pharmaceutical composition for the treatment or prophylaxis of bacterial infections, which composition comprises an effective amount of an antibacterial agent in admixture with a pharmaceutically acceptable carrier or diluent, wherein the antibacterial agent is selected from the group consisting of compounds of formula (I) and pharmaceutically acceptable salts and esters thereof, as defined above.

The invention still further provides a method for the treatment or prophylaxis of bacterial infections in an animal, preferably a mammal, which may be human, which method comprises administering to said animal an effective amount of an antibacterial agent in admixture with a pharmaceutically acceptable carrier or diluent, wherein the antibacterial agent is selected from the group consisting of compounds of formula (I) and pharmaceutically acceptable salts and esters thereof, as defined above.

The invention also provides processes for the preparation of the compounds of the present invention, which are described in more detail hereafter.

DETAILED DESCRIPTION OF INVENTION

In the compounds of the present invention, A represents a fully saturated heterocyclic group having from 4 to 6 ring atoms, of which one is a nitrogen atom and the remainder are carbon atoms, said nitrogen atom having on its remaining valence a group or atom $R^4$.

This group may be represented by the formula (III):

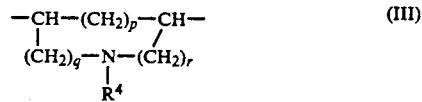

in which $R^4$ is as defined above and p, q and r are each zero or an integer such that (p+q+r)=an integer from 1 to 3, more preferably 1 or 2. Still more preferably p is 0, 1 or 2, q is 0 or 1 and r is 0, provided that (p+q+r)=an integer from 1 to 3.

Where $R^4$ represents an alkenyl group having from 2 to 5 carbon atoms, this may be a straight or branched chain group having from 2 to 5, preferably 3 or 4, carbon atoms, and examples include the vinyl, allyl, methallyl, 1-propenyl, isopropenyl, 1-butenyl, 2-butenyl, 3-butenyl, 1-pentenyl, 2-pentenyl, 3-pentenyl and 4-pentenyl groups, of which the vinyl, allyl, methallyl, 1-propenyl, isopropenyl and butenyl groups are preferred, the allyl and 2-butenyl groups being most preferred.

Where $R^4$ represents an alkynyl group having from 2 to 5 carbon atoms, this may be a straight or branched chain group having from 2 to 5, preferably 3 or 4, carbon atoms, and examples include the ethynyl, propargyl (2-propynyl), 1-propynyl, 1-butynyl, 2-butynyl, 3-butynyl, 1-pentynyl, 2-pentynyl, 3-pentynyl and 4-pentynyl groups, of which the propynyl and butynyl groups are preferred, the propargyl and 2-butynyl groups being most preferred.

Where $R^4$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, sec-pentyl, t-pentyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl and ethyl groups.

Where $R^4$ represents a substituted alkyl group having from 1 to 6 carbon atoms, this may be a straight or branched chain group having from 1 to 6, preferably from 1 to 4, carbon atoms, and examples include those unsubstituted groups listed above which are substituted by one or more of substituents (a). There is, in principle, no restriction on the number of such substituents, except such as may be imposed by the number of substitutable positions or, possibly, by steric constraints. In general, although not restrictive, from 1 to 5 substituents re common, from 1 to 3 being more usual, and, in many cases, one being most common.

Examples of groups and atoms which may be included in the list of substituents (a) are:

hydroxy groups, carboxy groups, cyano groups, sulfamoyl groups and sulfo groups;

groups of formula $-NR^aR^b$ or $-CONR^aR^b$, where $R^a$ and $R^b$ are independently selected from the group consisting of hydrogen atoms and alkyl groups having from 1 to 4 carbon atoms (examples of which are included among the alkyl groups which may be represented by $R^4$), i.e. amino and carbamoyl groups which may be unsubstituted or have one or two alkyl substituents, such as the amino, methylamino, ethylamino, propylamino, isopropylamino, dimethylamino, diethylamino, N-butyl-N-methylamino, N-t-butyl-N-methylamino, N-methyl-N-propylamino, N-ethyl-N-propylamino, dipropylamino, diisopropylamino, butylamino, isobutylamino, dibutylamino, diisobutylamino, carbamoyl, methylcarbamoyl, ethylcarbamoyl, propylcarbamoyl, isopropylcarbamoyl, dimethylcarbamoyl, diethylcarbamoyl, N-butyl-N-methylcarbamoyl, N-t-butyl-N-methylcarbamoyl, N-methyl-N-propylcarbamoyl, N-ethyl-N-propylcarbamoyl, dipropylcarbamoyl, diisopropylcarbamoyl, butylcarbamoyl, isobutylcarbamoyl, dibutylcarbamoyl and diisobutylcarbamoyl groups; and halogen atoms, such as the fluorine, chlorine, bromine and iodine atoms.

Where $R^4$ represents a group of formula $-C(=NH)R^5$, $R^5$ represents a hydrogen atom or an alkyl group having from 1 to 6 carbon atoms. Such alkyl groups may be as defined and exemplified in relation to the alkyl groups included in the groups which may be represented by $R^4$ $R^1$ may represent a hydrogen atom or a methyl group, but is preferably a methyl group.

Where $R^2$ may represent a hydrogen atom or an alkyl group, the alkyl groups may be as defined and exemplified in relation to the alkyl groups included in the groups which may be represented by $R^4$ Where Q represents a group of formula $-B-N^+R^8R^9R^{10}$, and any of $R^8$, $R^9$ and $R^{10}$ represents an alkenyl group having from 2 to 5 carbon atoms, an alkynyl group having from 2 to 5 carbon atoms or an alkyl group having from 1 to 6 carbon atoms, all of these groups are exemplified in relation to the similar groups which may be represented by $R^4$ and the examples given there apply *mutatis mutandis* to $R^8$, $R^9$ and $R^{10}$. Where $R^8$ and/or $R^9$ and/or $R^{10}$ represents a substituted alkyl group having from 1 to 6 carbon atoms, this may be as defined and exemplified above in relation to the unsubstituted groups, but is substituted by at least one substituent selected from the group consisting of substituents (b), for example:

hydroxy groups, carboxy groups, cyano groups, sulfamoyl groups, ureido groups and sulfo groups;

groups of formula $-NR^aR^b$, where $R^a$ and $R^b$ are as defined above, such as the amino, methylamino, ethylamino, propylamino, isopropylamino, dimethylamino, diethylamino, N-butyl-N-methylamino, N-t-butyl-N-methylamino, N-methyl-N-propylamino, N-ethyl-N-propylamino, isobutylamino, dibutylamino and diisobutylamino groups;

groups of formula $-CONR^cR^d$ or $-OCONR^cR^d$, where $R^c$ and $R^d$ are independently selected from the group consisting of hydrogen atoms, alkyl groups having from 1 to 4 carbon atoms, and substituted alkyl groups which have from 1 to 4 carbon atoms and which have at least one substituent selected from the group consisting of substituents (d) defined above and exemplified below, such as the carbamoyl, methylcarbamoyl, ethylcarbamoyl, propylcarbamoyl, isopropylcarbamoyl, dimethylcarbamoyl, diethylcarbamoyl, N-butyl-N-methylcarbamoyl, N-t-butyl-N-methylcarbamoyl, N-methyl-N-propylcarbamoyl, N-ethyl-N-propylcarbamoyl, dipropylcarbamoyl, diisopropylcarbamoyl, butylcarbamoyl, isobutylcarbamoyl, dibutylcarbamoyl and diisobutylcarbamoyl groups and such groups having one or more (preferably one) of substituents (d), defined above and exemplified below;

halogen atoms, such as the fluorine, chlorine, bromine and iodine atoms;

alkenyl groups having from 2 to 5, preferably 3 or 4, carbon atoms, such as the vinyl, allyl, methallyl, 1-propenyl, isopropenyl, 1-butenyl, 2-butenyl, 3-butenyl, 1-pentenyl, 2-pentenyl, 3-pentenyl and 4-pentenyl groups, of which the vinyl, allyl, methallyl, 1-propenyl, isopropenyl and butenyl groups are preferred, the allyl and 2-butenyl groups being most preferred;

alkoxy groups having from 1 to 4 carbon atoms, such as the methoxy, ethoxy, propoxy, isopropoxy, butoxy, isobutoxy, sec-butoxy and t-butoxy groups;

alkoxycarbonyl groups having from 2 to 5 carbon atoms, such as the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups;

alkanoyl groups having from 1 to 4 carbon atoms, such as the formyl, acetyl, propionyl, butyryl and isobutyryl groups;

alkanoylamino groups having from 1 to 4 carbon atoms, such as the formylamino, acetylamino, propionylamino, butyrylamino and isobutyrylamino groups;

alkanoyloxy groups having from 1 to 4 carbon atoms, such as the formyloxy, acetoxy, propionyloxy, butyryloxy and isobutyryloxy groups;

alkylthio groups having from 1 to 4 carbon atoms, such as the methylthio, ethylthio, propylthio, isopropylthio, butylthio, isobutylthio, sec-butylthio and t-butylthio groups;

alkylsulfinyl groups having from 1 to 4 carbon atoms, such as the methylsulfinyl, ethylsulfinyl, propylsulfinyl, isopropylsulfinyl, butylsulfinyl, isobutylsulfinyl, sec-butylsulfinyl and t-butylsulfinyl groups; and alkylsulfonyl groups having from 1 to 4 carbon atoms, such as the methylsulfonyl, ethylsulfonyl, propylsulfonyl, isopropylsulfonyl, butylsulfonyl, isobutylsulfonyl, sec-butylsulfonyl and t-butylsulfonyl groups.

Examples of the groups which may be included in substituents (d) are:

hydroxy and carboxy groups; and groups of formulae $-CONR^aR^b$ and $-OCONR^aR^b$, where $R^a$ and $R^b$ are as defined above, e.g. the carbamoyl, methylcarbamoyl, ethylcarbamoyl, propylcarbamoyl, isopropylcarbamoyl, dimethylcarbamoyl, diethylcarbamoyl, N-butyl-N-methylcarbamoyl, N-t-butyl-N-methylcarbamoyl, N-methyl-N-propylcarbamoyl, N-ethyl-N-propylcarbamoyl, dipropylcarbamoyl, diisopropylcarbamoyl, butylcarbamoyl, isobutylcarbamoyl, dibutylcarbamoyl, diisobutylcarbamoyl, carbamoyloxy, methylcarbamoyloxy, ethylcarbamoyloxy, propylcarbamoyloxy, isopropylcarbamoyloxy, dimethylcarbamoyloxy, diethylcarbamoyloxy, N-butyl-N-methylcarbamoyloxy, N-t-butyl-N-methylcarbamoyloxy, N-methyl-N-propylcarbamoyloxy, N-ethyl-N-propylcarbamoyloxy, dipropylcarbamoyloxy, diisopropylcarbamoyloxy, butylcarbamoyloxy, isobutylcarbamoyloxy, dibutylcarbamoyloxy and diisobutylcarbamoyloxy groups.

In the above formula, B represents an alkylene or alkylidene group having from 1 to 4 carbon atoms. This can be attached to the group of formula $-N^+R^8R^9R^{10}$ and the group of formula $-S-A-CO-N-$ through the same atom (in which case the group is correctly called an "alkylidene" group) or through different atoms (in which case the name "alkylene" group is appropriate). For the avoidance of doubt, it should be noted that both types of group are often referred to collectively as "alkylene" groups. Examples of such groups include the methylene, ethylene, ethylidene, trimethylene, tetramethylene, isopropylidene, propylidene, 1-methylethylene, 1-ethylethylene, 2-methylethylene, 2-ethylethylene, 1-methylpropylene and 2-methylpropylene groups. Of these, the methylene, ethylene, trimethylene and propylidene groups are preferred.

Where Q represents a heterocyclic group having from 4 to 10 ring atoms in a single or bridged ring, one of said ring atoms is a quaternary nitrogen atom of formula $>N^+R^{11}R^{12}$, wherein $R^{11}$ and $R^{12}$ are independently selected from the group consisting of alkenyl groups having from 2 to 5 carbon atoms, alkynyl groups having from 2 to 5 carbon atoms and alkyl groups having from 1 to 6 carbon atoms; all of these groups are exemplified in relation to the similar groups which may be represented by $R^4$ and the examples given there apply *mutatis mutandis* to $R^{11}$ and $R^{12}$. Where $R^{11}$ and/or $R^{12}$ represents a substituted alkyl group having from 1 to 6 carbon atoms, this may be as defined and exemplified above in relation to the unsubstituted groups, but is substituted by at least one substituent selected from the group consisting of substituents (b), for example those substituents (b) exemplified above.

The heterocyclic group represented by Q may be a fully saturated ring, or it may be partially unsaturated; it must, however, contain a quaternary nitrogen atom attached to two groups, $R^{11}$ and $R^{12}$, and so that atom, at least, must not take part in any multiple bonds. In addition, it may optionally contain one or two other hetero-atoms, which may be oxygen, sulfur or nitrogen atoms. Where there are two such additional hetero-atoms, we prefer that both should be nitrogen atoms or one should be a nitrogen atom and one should be an oxygen or sulfur atom, although both can be sulfur or oxygen atoms or one can be a sulfur atom and one can be an oxygen atom, if desired. The remaining atoms are carbon atoms. Preferably, where the ring represented by Q is a monocyclic ring, it has from 4 to 7, more preferably 5 or 6, ring atoms, and, where it is a bicyclic ring system, it has from 6 to 10, more preferably from 7 to 9, ring atoms. Examples of heterocyclic rings which may form part of Q include the pyrrolidine, piperidine, morpholine, thiomorpholine, azetidine, piperazine, quinuclidine and homopiperazine rings, and these may be attached to the group of formula $-S-A-CO-N-$ via any ring atom, provided that at least one nitrogen atom is free to be quaternised. That is the groups are optionally substituted azetidinio, pyrrolidinio, piperidinio, piperazinio, homopiperazinio, quinuclidinio, morpholinio or thiomorpholinio groups.

Such a heterocyclic group represented by Q is, of course, substituted on the quaternary nitrogen atom; other than this, it may be unsubstituted or it may be substituted by at least one, and preferably from 0 to 3, of substituents (c):

hydroxy groups;

groups of formula $-CONR^aR^b$, where $R^a$ and $R^b$ are as defined above, e.g. carbamoyl, methylcarbamoyl, ethylcarbamoyl, propylcarbamoyl, isopropylcarbamoyl, dimethylcarbamoyl, diethylcarbamoyl, N-butyl-N-methylcarbamoyl, N-t-butyl-N-methylcarbamoyl, N-methyl-N-propylcarbamoyl, N-ethyl-N-propylcarbamoyl, dipropylcarbamoyl, diisopropylcarbamoyl, butylcarbamoyl, isobutylcarbamoyl, dibutylcarbamoyl and diisobutylcarbamoyl groups;

alkyl groups having from 1 to 4 carbon atoms, such as the methyl, ethyl, propyl, isopropyl, butyl, isobutyl, sec-butyl and t-butyl groups; and halogen atoms, such as the fluorine, chlorine, bromine and iodine atoms.

Where Q represents an alkyl group having from 1 to 6 carbon atoms substituted by a heterocyclic group as defined above, the alkyl group may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, sec-pentyl, t-pentyl, hexyl and isohexyl groups. Of these, we prefer those alkyl groups having from 1 to 3 carbon atoms, preferably the methyl, ethyl and propyl groups, and most preferably the methyl and ethyl groups.

Where Q represents an alkyl group having from 1 to 6 carbon atoms and substituted by an aromatic heterocyclic group having from 5 to 8 ring atoms, one of said ring atoms being a quaternary nitrogen atom of formula

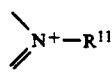

(wherein $R^{11}$ is as defined above), the alkyl group and $R^{11}$ may be as defined and exemplified above, and the heterocyclic group may have 0, 1 or 2 other nitrogen and/or oxygen and/or sulfur hetero-atoms. Examples of such groups include the imidazolio, thiazolio, thiadiazolio, pyrazolio, oxazolio, isoxazolio, triazolio, pyridinio, pyrazinio, pyrimidinio and pyridazinio groups.

Where $R^2$ and Q, together with the nitrogen atom to which they are attached, represent a group of formula (II):

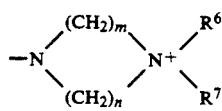

(II)

in which m, n, $R^6$ and $R^7$ are as defined above, we prefer that m and n should each be 2 or 3, more preferably m should be 2 and n should be 2 or 3. $R^6$ may represent an alkyl group having from 1 to 6 carbon atoms or a substituted alkyl group which has from 1 to 6 carbon atoms and which is substituted by at least one of substituents (a), whilst $R^7$ may represents an alkyenyl group having from 2 to 5 carbon atoms, an alkynyl group having from 2 to 5 carbon atoms, an alkyl group having from 1 to 6 carbon atoms or a substituted alkyl group which has from 1 to 6 carbon atoms and which is substituted by at least one of substituents (b); in each case, these may be as exemplified above in relation to $R^4$ or $R^8$, $R^9$ and $R^{10}$, as appropriate.

Where the group of formula (II) is substituted on one or more of the carbon atoms, the substituents are selected from the group consisting of alkyl groups and oxygen atoms. There is no particular restriction on the number of the substituents, which will only be limited by the number of substitutable positions and possibly by steric constraints; however, in the case of alkyl substituents, from 1 to 4, more preferably from 1 to 3 and most preferably 1 or 2, are preferred; in the case of oxygen atoms (which, with the carbon atoms to which they are attached, form an oxo group), 1 or 2 are preferred, 1 being more preferred. In general, however, the unsubstituted groups are preferred. The alkyl groups may be straight or branched chain groups having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, sec-pentyl, t-pentyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

Those compounds of the present invention where $R^3$ represents a hydrogen atom are carboxylic acids and can form esters. There is no limitation upon the nature of such esters, provided that, where the resulting compound is to be used for therapeutic purposes, it is pharmaceutically acceptable, which, as is well known in the art, means that the compound does not have reduced activity (or unacceptably reduced activity) or increased toxicity (or unacceptably increased toxicity) as compared with the corresponding compound of formula (I), i.e. the free acid. Where, however, the compound is to be used for non-therapeutic purposes, e.g. as an intermediate in the preparation of other compounds, even this limitation does not apply, and the nature of the ester group may be chosen having regard simply to process criteria. Examples of suitable ester groups which may replace the hydrogen atom of the carboxy group include:

$C_1$–$C_6$ alkyl groups, such as those exemplified in relation to $R^4$, but most preferably the methyl, ethyl and t-butyl groups;

aralkyl groups in which the aromatic group is $C_6$–$C_{14}$, which may be substituted or unsubstituted, and, if substituted, may have at least one substituent, for example selected from the group consisting of substituents (e), defined below; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 4-methoxybenzyl and piperonyl groups;

alkenyl groups, having from 2 to 6 carbon atoms, which may be substituted or unsubstituted and, if substituted, have at least one substituent selected from the group consisting of halogen atoms; examples of the unsubstituted groups are given above in relation to $R^4$, and preferred groups include the allyl, 2-chloroallyl and 2-methylallyl groups;

halogenated $C_1$–$C_6$, preferably $C_1$–$C_4$, alkyl groups in which the alkyl part is as defined and exemplified in relation to the alkyl groups which may be represented by $R^4$, and the halogen atom is chlorine, fluorine, bromine or iodine, such as the 2,2,2-trichloroethyl, 2-haloethyl (e.g. 2-chloro- ethyl, 2-fluoroethyl, 2-bromoethyl or 2-iodoethyl), 2,2-dibromoethyl and 2,2,2-tribromoethyl group;

substituted silylalkyl groups, in which the alkyl part is as defined and exemplified in relation to the alkyl groups which may be represented by $R^4$, and the silyl group has up to 3 substituents selected from the group consisting of $C_1$–$C_6$ alkyl groups and phenyl groups which are unsubstituted or have at lest one substituent selected from the group consisting of substituents (e) defined below, for example a 2-trimethylsilylethyl group;

phenacyl groups, which may be unsubstituted or have at least one substituent selected from the group consisting of substituents (e) defined below, for example the phenacyl group itself or the p-bromophenacyl group;

alkoxymethyl groups, in which the alkoxy part is $C_1$–$C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxymethyl groups, in which the acyl group is preferably an alkanoyl group and is more preferably a $C_2$-$C_6$ alkanoyl group, such as the acetoxymethyl, propionyloxymethyl, butyryloxymethyl, isobutyryloxymethyl and pivaloyloxymethyl groups;

higher aliphatic acyloxyalkyl groups in which the acyl group is preferably an alkanoyl group and is more preferably a $C_2$-$C_6$ alkanoyl group, and the alkyl part is $C_2$-$C_6$, and preferably $C_2$-$C_4$, such as the 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably a $C_2$-$C_6$ alkanoyl group, the cycloalkyl substituent is $C_3$-$C_7$, and the alkyl part is a $C_1$-$C_6$ alkyl group, preferably a $C_1$-$C_4$ alkyl group, such as the (cyclohexylacetoxy)methyl, 1-)cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part is $C_1$-$C_{10}$, preferably $C_1$-$C_6$, and more preferably $C_1$-$C_4$, and the alkyl part is $C_1$-$C_6$, preferably $C_1$-$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$-$C_6$, preferably $C_1$-$C_4$, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group is $C_3$-$C_{10}$, preferably $C_3$-$C_7$, is mono- or poly-cyclic and is optionally substituted by at lest one (and preferably only one) $C_1$-$C_4$ alkyl group (e.g. selected from those alkyl groups exemplified above) and the alkyl group is a $C_1$-$C_6$, more preferably $C_1$-$C_4$, alkyl group (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethy, cyclopentylcarbonyloxymethyl, 1-cyclohexloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1methylcyclopentylcarbonyloxy)propyl, 2-(1-metylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent being $C_3$-$C_{10}$, preferably $C_3$-$C_7$, and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

(5-alkyl- or 5-phenyl- 2-oxo-1,3-dioxolen-4-yl) alkyl groups in which each alkyl group (which may be the same or different) is $C_1$-$C_6$, preferably $C_1$-$C_4$, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl and 1-(5-methyl-2-oxo-1,3-dioxolen-4-yl)ethyl groups; and other groups, such as the phthalidyl, indanyl and 2-oxo-4,5,6,7-tetrahydro-1,3-benzodioxolen-4-yl groups.

Of the above groups, we especially prefer the benzyl, benzhydryl, 4-nitrobenzyl, 4-methoxybenzyl, allyl, 2,2,2-trichloroethyl, 2,2,2-tribromoethyl, 2-trimethylsilylethyl, acetoxymethyl, pivaloyloxymethyl and 1-ethoxycarbonyloxyethyl groups.

Examples of groups and atoms which may be included in substituents (e) include:

hydroxy groups; carboxy groups; groups of formula $-NR^aR^b$, where $R^a$ and $R^b$ are as defined above; groups of formula $-CONR^cR^d$ or $-OCONR^cR^d$, where $R^c$ and $R^d$ are as defined above; cyano groups; sulfamoyl groups; ureido groups; sulfo groups; halogen atoms; alkenyl groups having from 2 to 5 carbon atoms; alkoxy groups having from 1 to 4 carbon atoms; alkoxycarbonyl groups having from 2 to 5 carbon atoms; alkanoyl groups having from 1 to 4 carbon atoms; alkanoylamino groups having from 1 to 4 carbon atoms; alkanoyloxy groups having from 1 to 4 carbon atoms; alkylthio groups having from 1 to 4 carbon atoms; alkylsulfinyl groups having from 1 to 4 carbon atoms and alkylsulfonyl groups having from 1 to 4 carbon atoms; all of which are as exemplified in relation to substituents (b), above;

nitro groups;

alkyl groups having from 1 to 6, preferably 1 to 4 carbon atoms, e.g. as exemplified in relation to $R^4$ above;

halogenated alkyl groups having from 1 to 6, preferably from 1 to 4 carbon atoms, e.g. as exemplified in relation to the ester groups above; and alkylenedioxy groups having from 1 to 3 carbon atoms, especially the methylenedioxy, ethylenedioxy and trimethylenedioxy groups, preferably the methylenedioxy group.

The compounds of formula (I) include a positively charged ion on the quarternary ammonium ion in the group represented by Q. Where $R^3$ represents a negative ionic charge, the positive charge of the quarternary ammonium ion is balanced by $R^3$. In this case, an acid addition salt may be formed with one or more of the other nitrogen atoms in the compound of formula (I). However, where $R^3$ represents a hydrogen atom or is replaced by an ester group, such as those exemplified above, the compound requires another anion to balance that positive charge. This other anion may be provided by the anionic part of an acid. In either case, the nature of the acid employed is not critical to the invention, provided that, where the resulting compound is to be used for therapeutic purposes, it is pharmaceutically acceptable, i.e. it does not have reduced activity (or unacceptably reduced activity) or increased toxicity (or unacceptably increased toxicity) as compared with the corresponding compound of formula (I). Where, however, the compound is to be used for non-therapeutic purposes, e.g. as an intermediate in the preparation of other compounds, even this limitation does not apply, and the nature of the ester group may be chosen having regard simply to process criteria. Examples of suitable acids which may be used to provide the balancing anion or which may form acid addition salts include:

mineral acids, especially hydrohalic acids, such as hydrochloric acid, hydrofluoric acid, hydrobromic acid or hydroiodic acid, or other mineral acids, such as sulfuric acid, nitric acid, perchloric acid or phosphoric acid;

organic carboxylic acids, such as oxalic acid, tartaric acid, maleic acid, succinic acid, acetic acid, benzoic acid, mandelic acid, ascorbic acid, lactic acid, gluconic acid, malic acid or citric acid; and sulfonic acids, e.g. fluorosulfonic acid, or alkanesulfonic or haloalkanesulfonic acids, such as methanesulfonic acid, trifluoromethanesulfonic acid or ethanesulfonic acid, or arylsulfonic acids, such as benzenesulfonic acid or p-toluenesulfonic acid.

Where $R^3$ represents a hydrogen atom, the compounds of the present invention can also form salts with cations, for example:

metals, especially alkali metals, such as sodium or potassium, alkaline earth metals, such as calcium or barium, and other metals, such as magnesium or aluminum;

the ammonium ion; and organic bases, including trialkylamines, such as trimethylamine or triethylamine, and other basic amines, such as procaine, dibenzylamine or phenethylamine.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific syntesis techniques are employed, individual isomers may be prepared directly; on the other hand, if a mixture of isomers is prepared, the individual isomers may be obtained by conventional resolution techniques.

Of the various isomers of the compounds of the present invention, we especially prefer those in which:

(a) when $R^1$ represents a hydrogen atom, those having the (5R, 6S) configuration and in which the hydroxy substituent at the α-position of the side chain at the 6-position is in the R configuration, which is the same configuration as that of thienamycin;

(b) when $R^1$ represents a methyl group, those in which the methyl group at the 1-position is in the R configuration, and especially those having the (5S, 6S) configuration and in which the hydroxy substituent at the α-position of the side chain at the 6-position is in the R configuration.

Preferred classes of compound of the present invention are those compounds of formula (I) and salts and esters thereof, wherein:

(A) A represents a fully saturated heterocyclic group having from 4 to 6 ring atoms, of which one is a nitrogen atom and the remainder are carbon atoms, said nitrogen atom having on its remaining valence a group or atom $R^4$, wherein:

$R^4$ represents: a hydrogen atom; an alkenyl group having 3 or 4 carbon atoms; an alkynyl group having 3 or 4 carbon atoms; an alkyl group having from 1 to 4 carbon atoms; a substituted alkyl group which has from 1 to 4 carbon atoms and which has at least one substituent selected from the group consisting of substituents ($a^i$), defined below; or a group of formula $-C(=NH)R^5$, wherein $R^5$ represents a hydrogen atom or an alkyl group having from 1 to 4 carbon atoms;

substituents ($a^i$):

hydroxy groups, carboxy groups, carbamoyl groups, cyano groups, sulfamoyl groups, sulfo groups, halogen atoms, and groups of formula $-NR^{a'}R^{b'}$, where $R^{a'}$ and $R^{b'}$ are independently selected from the group consisting of hydrogen atoms and alkyl groups having from 1 to 3 carbon atoms.

(B) $R^2$ represents a hydrogen atom or an alkyl group having from 1 to 4 carbon atoms.

(C) $R^2$ and Q, together with the nitrogen atom to which they are attached represent a group of formula (II), as defined above, wherein:

m and n are each 1, 2 or 3;

$R^6$ represents an alkyl group having from 1 to 4 carbon atoms or a substituted alkyl group which has from 1 to 4 carbon atoms and which has at least one substituent selected from the group consisting of substituents ($a^i$), defined in (A) above; and $R^7$ represents: an alkenyl group having 3 or 4 carbon atoms; an alkynyl group having 3 or 4 carbon atoms; an alkyl group having from 1 to 4 carbon atoms; or a substituted alkyl group which has from 1 to 4 carbon atoms and which has at least one substituent selected from the group consisting of substituents ($b^i$), defined below;

and the carbon atoms of said group of formula (II) are unsubstituted or they are substituted by at least one substituent selected from the group consisting of alkyl groups having from 1 to 4 carbon atoms and oxygen atoms;

substituents ($b^i$):

hydroxy groups; carboxy groups; groups of formula $-NR^aR^b$, where $R^a$ and $R^b$ are as defined above; groups of formula $-CONR^{c'}R^{d'}$ or $-OCONR^{c'}R^{d'}$, where $R^{c'}$ and $R^{d'}$ are independently selected from the group consisting of hydrogen atoms, alkyl groups having from 1 to 3 carbon atoms and substituted alkyl groups which have from 1 to 3 carbon atoms and which have at least one substituents selected from the group consisting of substituents ($d^i$) defined below, and $R^{c''}$ and $R^{d''}$ are independently selected from the group consisting of hydrogen atoms and alkyl groups having from 1 to 3 carbon atoms; cyano groups; sulfamoyl groups; ureido groups; sulfo groups; halogen atoms; alkoxy groups having from 1 to 3 carbon atoms; alkoxycarbonyl groups having from 2 to 4 carbon atoms; alkanoyl groups having from 1 to 3 carbon atoms; alkanoylamino groups having from 1 to 3 carbon atoms; alkanoyloxy groups having from 1 to 3 carbon atoms; alkylthio groups having from 1 to 3 carbon atoms; alkylsulfinyl groups having from 1 to 3 carbon atoms and alkylsulfonyl groups having from 1 to 3 carbon atoms; and substituents (d$^i$):

hydroxy groups; carboxy groups; carbamoyl groups; and carbamoyloxy groups.

(D) Q represents a group of formula —B—N$^+$R$^8$R$^9$R$^{10}$, wherein: R$^8$, R$^9$ and R$^{10}$ are independently selected from the group consisting of alkenyl groups having 3 or 4 carbon atoms, alkynyl groups having 3 or 4 carbon atoms, alkyl groups having from 1 to 4 carbon atoms and substituted alkyl groups which have from 1 to 4 carbon atoms and which have at least one substituent selected from the group consisting of substituents (b$^i$), defined above; and B represents an alkylene or alkylidene group having from 1 to 4 carbon atoms.

(E) Q represents a non-aromatic heterocyclic group having from 4 to 10 ring atoms in a single or bridged ring, one of said ring atoms being a quarternary nitrogen atom of formula >N$^+$R$^{11}$R$^{12}$, wherein:

R$^{11}$ and R$^{12}$ are independently selected from the group consisting of alkenyl groups having 3 or 4 carbon atoms; alkynyl groups having 3 or 4 carbon atoms; alkyl groups having from 1 to 4 carbon atoms; and substituted alkyl groups having from 1 to 4 carbon atoms and having at least one substituent selected from the group consisting of substituents (b$^i$), defined above;

and 0, 1 or 2 of said ring atoms being selected from the group consisting of nitrogen, oxygen and sulfur heteroatoms, the remainder being carbon atoms, said heterocyclic group being otherwise unsubstituted or having at least one substituent selected from the group consisting of substituents (c$^i$), defined below;

substituents (c$^i$):

hydroxy groups, carbamoyl groups, alkyl groups having from 1 to 3 carbon atoms and halogen atoms.

(F) Q represents an alkyl group having from 1 to 4 carbon atoms and substituted by a non-aromatic heterocyclic group having from 4 to 10 ring atoms in a single or bridged ring, one of said ring atoms being a quarternary nitrogen atom of formula >N$^+$R$^{11}$R$^{12}$, wherein:

R$^{11}$ and R$^{12}$ are independently selected from the group consisting of: alkenyl groups having 3 or 4 carbon atoms; alkynyl groups having 3 or 4 carbon atoms; alkyl groups having from 1 to 4 carbon atoms; and substituted alkyl groups having from 1 to 4 carbon atoms and having at least one substituent selected from the group consisting of substituents (b$^i$), defined above; and 0, 1 or 2 of said ring atoms being selected from the group consisting of nitrogen, oxygen and sulfur heteroatoms, the remainder being carbon atoms, said heterocyclic group being otherwise unsubstituted or having at least one substituent selected from the group consisting of substituents (c$^i$), defined above.

(G) Q represents an alkyl group having from 1 to 4 carbon atoms and substituted by an aromatic heterocyclic group having from 5 to 7 ring atoms, one of said ring atoms being a quarternary nitrogen atom of formula

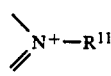

wherein R$^{11}$ represents: an alkenyl group having 3 or 4 carbon atoms; an alkynyl group having 3 or 4 carbon atoms; an alkyl group having from 1 to 4 carbon atoms; or a substituted alkyl group having from 1 to 4 carbon atoms and having at least one substituent selected from the group consisting of substituents (b$^i$), defined above: and 0, 1 or 2 of said ring atoms being selected from the group consisting of nitrogen, oxygen and sulfur heteroatoms, the remainder being carbon atoms, said heterocyclic group being otherwise unsubstituted or having at least one substituent selected from the group consisting of substituents (c$^i$), defined above.

Particularly preferred among these are those compounds in which A is as defined in (A) above and either R$^2$ and Q are as defined in (C) above or R$^2$ is as defined in (B) above and Q is as defined in one of (D), (E), (F) or (G) above.

More preferred compounds of the present invention are those compounds of formula (I) and salts and esters thereof, wherein:

(H) A represents a fully saturated heterocyclic group having from 4 to 6 ring atoms, of which one is a nitrogen atom and the remainder are carbon atoms, said nitrogen atom having on its remaining valence a group of atom R$^4$, wherein:

R$^4$ represents a hydrogen atom; an alkyl group having from 1 to 4 carbon atoms; a substituted alkyl group which has from 1 to 4 carbon atoms and which has at least one substituent selected from the group consisting of substituents (a$^{ii}$), defined below; or a group of formula —C(=NH)R$^5$, wherein R$^5$ represents a hydrogen atom or an alkyl group having from 1 to 4 carbon atoms;

substituents (a$^{ii}$):

hydroxy groups, carboxy groups, carbamoyl groups, cyano groups, halogen atoms, and groups of formula —NR$^{a'}$R$^{b'}$, where R$^{a'}$ and R$^{b'}$ are independently selected from the group consisting of hydrogen atoms and alkyl groups having from 1 to 3 carbon atoms.

(I) R$^2$ and Q, together with the nitrogen atom to which they are attached represent a group of formula (II), as defined above, wherein:

m and n are each 1, 2 or 3;

R$^6$ represents an alkyl group having from 1 to 4 carbon atoms or a substituted alkyl group which has from 1 to 4 carbon atoms and which has at least one substituent selected from the group consisting of substituents (a$^{iii}$), defined below; and R$^7$ represents: an alkyl group having from 1 to 3 carbon atoms; or a substituted alkyl group which has from 1 to 3 carbon atoms and which has at least one substituent selected from the group consisting of substituents (b$^{ii}$), defined below;

and the carbon atoms of said group of formula (II) are unsubstituted or they are substituted by at least one substituent selected from the group consisting of alkyl groups having from 1 to 4 carbon atoms and oxygen atoms;

substituents (a$^{iii}$):

hydroxy groups, carboxy groups, carbamoyl groups, halogen atoms, and amino groups;

substituents (b$^{ii}$):

hydroxy groups; carboxy groups; groups of formula —NR$^{a''}$R$^{b''}$, where R$^{a''}$ and R$^{b''}$ are independently selected from the group consisting of hydrogen atoms and alkyl groups having from 1 to 3 carbon atoms; groups of formula —CONR$^{a''}$R$^{b''}$ or —OCONR$^{a''}$R$^{b''}$, where R$^{a''}$ and R$^{b''}$ are as defined above; cyano groups; sulfamoyl groups; ureido groups; sulfo groups; halogen atoms;

alkoxy groups having from 1 to 3 carbon atoms; alkoxycarbonyl groups having from 2 to 4 carbon atoms; alkanoyl groups having 2 to 3 carbon atoms; alkanoylamino groups having 2 or 3 carbon atoms; alkanoyloxy groups having 2 or 3 carbon atoms; alkylthio groups having from 1 to 3 carbon atoms; alkylsulfinyl groups having from 1 to 3 carbon atoms and alkylsulfonyl groups having from 1 to 3 carbon atoms.

(J) $R^2$ represents a hydrogen atom; and

Q represents a group of formula $-B-N^+R^8R^9R^{10}$, wherein: $R^8$, $R^9$ and $R^{10}$ are independently selected from the group consisting of alkyl groups having from 1 to 3 carbon atoms and consisting of alkyl groups which have from 1 to 3 carbon atoms and which have at least one substituent selected from the group consisting of substituents ($b^{ii}$), defined above; and B represents an alkylene or alkylidene group having from 1 to 3 carbon atoms.

(K) Q represents a heterocyclic group having from 4 to 10 ring atoms in a single or bridged ring, one of said ring atoms being a quaternary nitrogen atom of formula $>N^+R^{11}R^{12}$, wherein:

$R^{11}$ and $R^{12}$ are independently selected from the group consisting of alkyl groups having from 1 to 3 carbon atoms and substituted alkyl groups having at least one substituent selected from the group consisting of substituents ($b^{ii}$), defined above;
and having no other hetero-atoms or having one other hetero-atom selected from the group consisting of nitrogen, oxygen and sulfur hetero-atoms, the remainder being carbon atoms, said heterocyclic group being otherwise unsubstituted or having at least one substituent selected from the group consisting of substituents ($c^{ii}$), defined below;

substituents ($c^{ii}$):

hydroxy groups, carbamoyl groups, halogen atoms and alkyl groups having from 1 to 3 carbon atoms;
of which we especially prefer those wherein Q represents an azetidinio, pyrrolidinio, piperidinio, piperazinio, homopiperazinino, quinuclidininio, morpholinio or thiomorpholinio group, in which the quarternary nitrogen atom is said group of formula $>N^+R^{11}R^{12}$, wherein $R^{11}$ and $R^{12}$ are as defined above, said group being unsubstituted on its carbon atoms or having at least one substituent selected from the group consisting of substituents ($c^{ii}$), defined above.

(L) Q represents an alkyl group having from 1 to 3 carbon atoms and substituted by a heterocyclic group having from 4 to 10 ring atoms in a single or bridged ring, one of said ring atoms being a quaternary nitrogen atom of formula $>N^+R^{11}R^{12}$, wherein:

$R^{11}$ and $R^{12}$ are independently selected from the group consisting of alkyl groups having from 1 to 3 carbon atoms and substituted alkyl groups having from 1 to 3 carbon atoms and having at least one substituent selected from the group consisting of substituents ($b^{ii}$), defined above;
and having no other hetero-atoms or having one other hetero-atom selected from the group consisting of nitrogen, oxygen and sulfur hetero-atoms, the remainder being carbon atoms, said heterocyclic group being otherwise unsubstituted or having at least one substituent selected from the group consisting of substituents ($c^{ii}$), defined above;
of which we especially prefer those wherein Q represents a methyl, ethyl or propyl group substituted by an azetidinio, pyrrolidinio, piperidinio, piperazinio, homopiperazinino, quinuclidinio, morpholinio or thiomorpholinio group, in which the quarternary nitrogen atom is said group of formula $>N^+R^{11}R^{12}$, wherein $R^{11}$ and $R^{12}$ are as defined above, said group being unsubstituted on its carbon atoms or having at least one substituent selected from the group consisting of substituents ($c^{ii}$), defined above.

(M) Q represents an alkyl group having from 1 to 3 carbon atoms and substituted by an aromatic heterocyclic group having 5 or 6 ring atoms, of which one is a quaternary nitrogen atom of formula

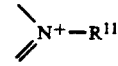

wherein $R^{11}$ represents an alkyl group having from 1 to 3 carbon atoms or a substituted alkyl group having from 1 to 3 carbon atoms and having at least one substituent selected from the group consisting of substituents ($b^{ii}$), defined above:
and having no other hetero-atoms or having one or two other hetero-atoms selected from the group consisting of nitrogen, oxygen and sulfur hetero-atoms, the remainder being carbon atoms, said heterocyclic group being otherwise unsubstituted or having at least one substituent selected from the group consisting of substituents ($c^{ii}$), defined above;

of which we especially prefer those wherein Q represents a methyl, ethyl or propyl group substituted by an imidazolio, thiazolio, thiadiazolio, pyrazolio, oxazolio, isoxazolio, triazolio, pyridinio, pyrazinio, pyrimidinio or pyridazinio group, in which the quarternary nitrogen atom is said group of formula

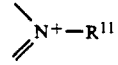

wherein $R^{11}$ is as defined above, said group being unsubstituted on its carbon atoms or having at least one substituent selected from the group consisting of methyl, ethyl and propyl substituents.

Still more preferred compounds of the invention are those compounds of formula (I) and salts and esters thereof, wherein:

(N) A represents a fully saturated heterocyclic group having 5 ring atoms, of which one is a nitrogen atom and the remainder are carbon atoms, said nitrogen atom having on its remaining valence a group or atom $R^4$. wherein:

$R^4$ represents: a hydrogen atom; a methyl group; an ethyl group; or a substituted methyl or ethyl group which has at least one substituent selected from the group consisting of hydroxy groups, carbamoyl groups and halogen atoms.

(O) $R^2$ and Q, together with the nitrogen atom to which they are attached represents a group of formula (II), as defined above, wherein:

m and n are each 2 or 3;

$R^6$ represents an alkyl group having from 1 to 4 carbon atoms or a substituted alkyl group which has from 1 to 4 carbon atoms and which has at least one substituent selected from the group consisting of hydroxy groups, carboxy groups, carbamoyl groups, cyano groups, halogen atoms and amino groups; and R[7] represents: an alkyl group having from 1 to 3 carbon atoms; or a substituted alkyl group which has from 1 to 3 carbon atoms and which has at least one substituent selected from the group consisting of substituents (b[iii]), defined below;

and the carbon atoms of said group of formula (II) are unsubstituted or they are substituted by at least one substituent selected from the group consisting of alkyl groups having from 1 to 4 carbon atoms and oxygen atoms;

substituents (b[iii]):

hydroxy groups; carboxy groups; groups of formula —NR[e]R[f], where R[e] and R[f] are independently selected from the group consisting of hydrogen atoms, methyl groups and ethyl groups; groups of formula —CONR[g]R[h], where R[g] and R[h] are independently selected from the group consisting of hydrogen atoms, alkyl groups having from 1 to 3 carbon atoms and substituted alkyl groups having from 1 to 3 carbon atoms and having at least one substituent selected from the group consisting of hydroxy, carboxy, carbamoyl and carbamoyloxy groups; groups of formula —OCONR[i]R[j], where R[i] and R[j] are independently selected from the group consisting of hydrogen atoms and alkyl groups having from 1 to 3 carbon atoms; cyano groups; sulfamoyl groups; ureido groups; sulfo groups; halogen atoms; alkoxy groups having from 1 to 3 carbon atoms; alkoxycarbonyl groups having from 2 to 4 carbon atoms; alkanoyl groups having 2 or 3 carbon atoms; alkanoylamino groups having 2 or 3 carbon atoms; alkanoyloxy groups having 2 or 3 carbon atoms; alkylthio groups having from 1 to 3 carbon atoms; alkylsulfinyl groups having from 1 or 3 carbon atoms and alkylsulfonyl groups having from 1 or 3 carbon atoms, still more preferably wherein said substituents (b[iii]) are selected from the group consisting of hydroxy groups; carboxy groups; groups of formula —NR[e]R[f], where R[e] and R[f] are independently selected from the group consisting of hydrogen atoms, methyl groups and ethyl groups; groups of formula —CONR[g]R[h], where R[g] and R[h] are independently selected from the group consisting of hydrogen atoms, alkyl groups having from 1 to 3 carbon atoms and substituted alkyl groups having from 1 to 3 carbon atoms and having at least one substituent selected from the group consisting of hydroxy, carboxy and carbamoyl groups; groups of formula —OCONR[i]R[j], where R[i] and R[j] are independently selected from the group consisting of hydrogen atoms and alkyl groups having from 1 to 3 carbon atoms; cyano groups; sulfamoyl groups; ureido groups; sulfo groups; halogen atoms; alkoxy groups having from 1 to 3 carbon atoms; alkoxycarbonyl groups having from 2 to 4 carbon atoms; alkanoyl groups having 2 or 3 carbon atoms; alkanoylamino groups having 2 or 3 carbon atoms; alkanoyloxy groups having 2 or 3 carbon atoms;; alkylthio groups having from 1 to 3 carbon atoms; alkylsulfinyl groups having from 1 to 3 carbon atoms and alkylsulfonyl groups having from 1 to 3 carbon atoms.

The most preferred compounds of the present invention are those compounds of formula (I) and salts and esters thereof, wherein A is as defined in (N) above and R[2] and Q are as defined in (O) above.

Specific examples of compounds of the present invention are given by the following formulae (I-1) to (I-6), in which the meaning of the substituent groups shown in the formulae are given in the corresponding one of the following Tables 1 to 6, i.e. Table 1 relates to formula (I-1), Table 2 relates to formula (I-2) and so on. In Table 6, the dash "-" means a direct bond in place of a "(A)". In the Tables, certain abbreviations are used, which have the following meanings:

| Ac | acetyl |
| All | allyl |
| Azt+ | azetidinyl 1-cation |
| Bu | butyl |
| Car | carbamoyl |
| Et | ethyl |
| Etc | ethoxycarbonyl |
| Imid+ | imidazolyl 3-cation |
| Me | methyl |
| Mec | methoxycarbonyl |
| Mor+ | morpholino 4-cation |
| Pip+ | piperidyl 1-cation |
| Pr | propyl |
| Prg | propargyl (= 2-propynyl) |
| Pym+ | pyrimidinyl 1-cation |
| Pyr+ | pyridyl 1-cation |
| Pyrd+ | pyrrolidinyl 1-cation |
| Pyzn+ | pyridazinyl 1-cation |
| Qnu+ | quinuclidinyl 1-cation |
| Sam | sulfamoyl |
| Sfo | sulfo |
| Thdz+ | 1,2,4-thiadiazolyl 4-cation |
| Thiz+ | thiazolyl 3-cation |
| Ur | ureido |

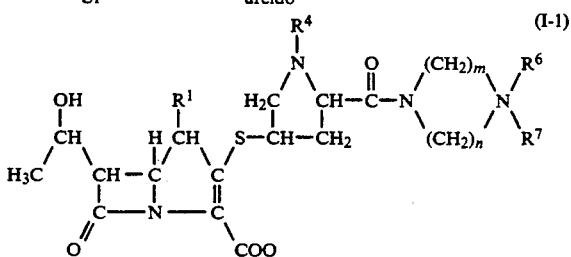

(I-1)

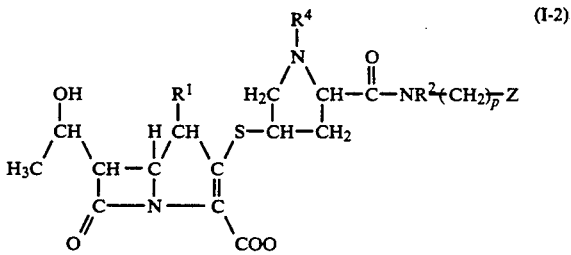

(I-2)

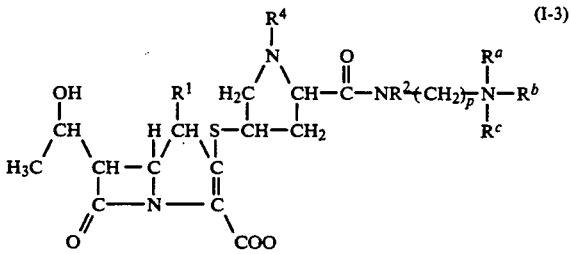

(I-3)

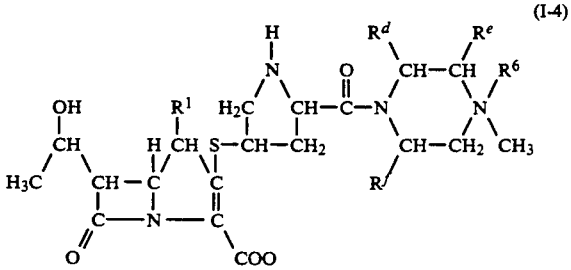

(I-4)

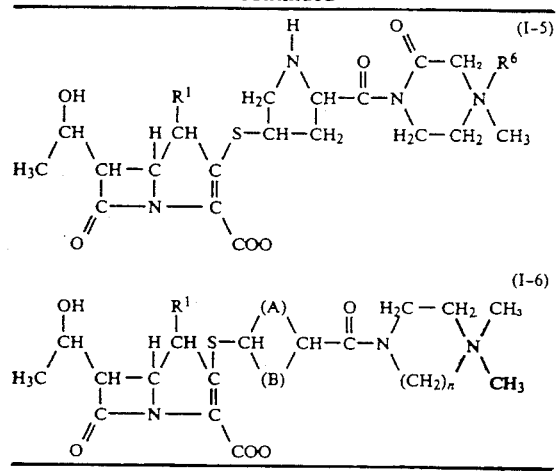

TABLE 1

| Cpd. No. | $R^1$ | $R^4$ | $R^6$ | $R^7$ | m | n |
|---|---|---|---|---|---|---|
| 1-1 | H | H | Me | Me | 2 | 2 |
| 1-2 | H | Me | Me | Me | 2 | 3 |
| 1-3 | H | H | MecCH$_2$ | Me | 2 | 2 |
| 1-4 | H | H | 2-HOEt | Me | 2 | 2 |
| 1-5 | H | H | CarCH$_2$ | Me | 2 | 2 |
| 1-6 | H | H | NCCH$_2$ | Me | 2 | 2 |
| 1-7 | H | H | HOOCCH$_2$ | Me | 2 | 2 |
| 1-8 | H | H | 2-NH$_2$Et | Me | 2 | 2 |
| 1-9 | H | H | 2-CarOEt | Me | 2 | 2 |
| 1-10 | H | H | 3-HOPr | Me | 2 | 2 |
| 1-11 | H | H | AcCH$_2$ | Me | 2 | 2 |
| 1-12 | H | H | 2-MeOEt | Me | 2 | 2 |
| 1-13 | H | H | 2-SfoEt | Me | 2 | 2 |
| 1-14 | H | H | MeSCH$_2$ | Me | 2 | 2 |
| 1-15 | H | H | MeS(O)CH$_2$ | Me | 2 | 2 |
| 1-16 | H | H | MeS(O$_2$)CH$_2$ | Me | 2 | 2 |
| 1-17 | H | Me | Me | Me | 2 | 2 |
| 1-18 | H | Et | Me | Me | 2 | 2 |
| 1-19 | H | CarCH$_2$ | Me | Me | 2 | 2 |
| 1-20 | H | 2-HOEt | Me | Me | 2 | 2 |
| 1-21 | H | 2-FEt | Me | Me | 2 | 2 |
| 1-22 | H | HOOCCH$_2$ | Me | Me | 2 | 2 |
| 1-23 | H | NCCH$_2$ | Me | Me | 2 | 2 |
| 1-24 | H | H | Et | Me | 2 | 2 |
| 1-25 | H | H | 2-FEt | Me | 2 | 2 |
| 1-26 | H | H | Et | Et | 2 | 2 |
| 1-27 | H | H | Me | 2-HOEt | 2 | 3 |
| 1-28 | H | H | Me | CarCH$_2$ | 2 | 3 |
| 1-29 | H | H | Me | HOOCCH$_2$ | 2 | 3 |
| 1-30 | H | H | Me | 2-FEt | 2 | 3 |
| 1-31 | H | H | Me | 2-NH$_2$Et | 2 | 3 |
| 1-32 | H | Me | Me | Me | 2 | 2 |
| 1-33 | H | Et | Me | Me | 2 | 3 |
| 1-34 | H | 2-HOEt | Me | Me | 2 | 3 |
| 1-35 | H | 2-FEt | Me | Me | 2 | 3 |
| 1-36 | H | HOOCCH$_2$ | Me | Me | 2 | 3 |
| 1-37 | H | CarCH$_2$ | Me | Me | 2 | 3 |
| 1-38 | H | NCCH$_2$ | Me | Me | 2 | 3 |
| 1-39 | H | H | Me | 2-SfoEt | 2 | 3 |
| 1-40 | H | H | Me | 2-SamEt | 2 | 2 |
| 1-41 | H | H | Me | 2-CarOEt | 2 | 3 |
| 1-42 | H | H | Me | 2-SamEt | 2 | 3 |
| 1-43 | H | H | Me | All | 2 | 2 |
| 1-44 | H | H | Me | Prg | 2 | 2 |
| 1-45 | H | H | Me | (MeCar)CH$_2$ | 2 | 2 |
| 1-46 | H | CH$_3$C(:NH)— | Me | Me | 2 | 2 |
| 1-47 | H | NH:CH— | Me | Me | 2 | 2 |
| 1-48 | H | All | Me | Me | 2 | 2 |
| 1-49 | H | Prg | Me | Me | 2 | 2 |
| 1-50 | H | H | Me | 2-CarEt | 2 | 2 |
| 1-51 | H | H | Me | 2-UrEt | 2 | 2 |
| 1-52 | H | H | Me | 3-HOBu | 2 | 2 |
| 1-53 | H | CH$_3$C(:NH)— | Me | Me | 2 | 3 |
| 1-54 | H | H | Me | 2-CarEt | 2 | 3 |
| 1-55 | H | NH:CH— | Me | Me | 2 | 3 |
| 1-56 | H | H | Pr | 2-CarOEt | 2 | 3 |
| 1-57 | H | H | Me | All | 2 | 3 |
| 1-58 | H | H | Me | 2-(MeCar)Et | 2 | 3 |
| 1-59 | H | H | Me | EtcCH$_2$ | 2 | 2 |
| 1-60 | H | H | Me | 2-(AcNH)Et | 2 | 2 |
| 1-61 | H | H | Me | 2-(AcO)Et | 2 | 2 |
| 1-62 | H | H | Me | (diMeCar)CH$_2$ | 2 | 2 |
| 1-63 | H | H | Me | (2-HOEtCar)CH$_2$ | 2 | 2 |
| 1-64 | H | H | Me | (HOOCCH$_2$Car)CH$_2$ | 2 | 2 |
| 1-65 | H | H | Me | (CarCH$_2$Car)CH$_2$ | 2 | 2 |
| 1-66 | H | H | Me | 2-HOOCEt | 2 | 2 |
| 1-67 | H | H | Me | (2-CarOEt)CarCH$_2$ | 2 | 2 |
| 1-68 | H | H | Me | 2-HOPr | 2 | 2 |

TABLE 1-continued

| Cpd. No. | R¹ | R⁴ | R⁶ | R⁷ | m | n |
|---|---|---|---|---|---|---|
| 1-69 | H | H | Me | 2-(diMeCarO)Et | 2 | 2 |
| 1-70 | H | H | Me | 2,3-diHOPr | 2 | 2 |
| 1-71 | H | H | Me | 3-SfoPr | 2 | 2 |
| 1-72 | H | H | Me | NCCH₂ | 2 | 3 |
| 1-73 | H | H | Me | (MeCar)CH₂ | 2 | 3 |
| 1-74 | H | H | Me | (diMeCar)CH₂ | 2 | 3 |
| 1-75 | H | H | Me | (2-HOEtCar)CH₂ | 2 | 3 |
| 1-76 | H | H | Me | AcCH₂ | 2 | 3 |
| 1-77 | H | H | Me | 2-HOPr | 2 | 3 |
| 1-78 | H | H | 2-HOEt | 2-HOEt | 2 | 3 |
| 1-79 | H | H | Me | (HOOCCH₂Car)CH₂ | 2 | 3 |
| 1-80 | H | H | Me | 2-HOOCEt | 2 | 3 |
| 1-81 | H | H | Et | 2-HOEt | 2 | 2 |
| 1-82 | H | H | Et | 2-CarOEt | 2 | 2 |
| 1-83 | H | H | Et | CarCH₂ | 2 | 2 |
| 1-84 | H | H | Et | HOOCCH₂ | 2 | 2 |
| 1-85 | H | H | Et | 2-HOEt | 2 | 3 |
| 1-86 | H | H | Et | 2-CarOEt | 2 | 3 |
| 1-87 | H | H | Et | CarCH₂ | 2 | 3 |
| 1-88 | H | H | Et | HOOCCH₂ | 2 | 3 |
| 1-89 | H | H | Me | 2-FEt | 2 | 3 |
| 1-90 | H | H | CarCH₂ | CarCH₂ | 2 | 2 |
| 1-91 | H | H | 2-HOEt | HOOCCH₂ | 2 | 2 |
| 1-92 | H | H | 2-HOEt | CarCH₂ | 2 | 2 |
| 1-93 | H | H | 2-CarOEt | 2-HOEt | 2 | 2 |
| 1-94 | H | H | 2-HOEt | 2-HOEt | 2 | 3 |
| 1-95 | H | H | 2-CarOEt | 2-HOEt | 2 | 3 |
| 1-96 | H | H | HOOCCH₂ | 2-HOEt | 2 | 3 |
| 1-97 | H | H | 2-HOEt | CarCH₂ | 2 | 3 |
| 1-98 | H | H | MecCH₂ | Me | 2 | 3 |
| 1-99 | H | H | EtcCH₂ | Me | 2 | 3 |
| 1-100 | H | H | EtcCH₂ | Me | 2 | 2 |
| 1-101 | H | H | 2-MeOEt | Me | 2 | 3 |
| 1-102 | H | H | 2-AcOEt | Me | 2 | 3 |
| 1-103 | H | 3-SfoPr | Me | Me | 2 | 2 |
| 1-104 | H | SamCH₂ | Me | Me | 2 | 2 |
| 1-105 | H | 2-NH₂Et | Me | Me | 2 | 2 |
| 1-106 | H | H | 2-HOEt | 2-NH₂Et | 2 | 2 |
| 1-107 | H | 2-(MeNH)Et | Me | Me | 2 | 2 |
| 1-108 | H | 2-(diMeN)Et | Me | Me | 2 | 2 |
| 1-109 | H | H | 2-(MeNH)Et | Me | 2 | 2 |
| 1-110 | H | H | 2-(diMeN)Et | Me | 2 | 2 |
| 1-111 | H | H | 2-(MeNH)Et | Me | 2 | 3 |
| 1-112 | H | H | 2-(diMeN)Et | Me | 2 | 3 |
| 1-113 | Me | H | Me | Me | 2 | 2 |
| 1-114 | Me | H | Me | Me | 2 | 3 |
| 1-115 | Me | H | MecCH₂ | Me | 2 | 2 |
| 1-116 | Me | H | 2-HOEt | Me | 2 | 2 |
| 1-117 | Me | H | CarCH₂ | Me | 2 | 2 |
| 1-118 | Me | H | NCCH₂ | Me | 2 | 2 |
| 1-119 | Me | H | HOOCCH₂ | Me | 2 | 2 |
| 1-120 | Me | H | 2-NH₂Et | Me | 2 | 2 |
| 1-121 | Me | H | 2-CarOEt | Me | 2 | 2 |
| 1-122 | Me | H | 3-HOPr | Me | 2 | 2 |
| 1-123 | Me | H | AcCH₂ | Me | 2 | 2 |
| 1-124 | Me | H | 2-MeOEt | Me | 2 | 2 |
| 1-125 | Me | H | 2-SfoEt | Me | 2 | 2 |
| 1-126 | Me | H | MeSCH₂ | Me | 2 | 2 |
| 1-127 | Me | H | MeS(O)CH₂ | Me | 2 | 2 |
| 1-128 | Me | H | MeS(O₂)CH₂ | Me | 2 | 2 |
| 1-129 | Me | Me | Me | Me | 2 | 2 |
| 1-130 | Me | Et | Me | Me | 2 | 2 |
| 1-131 | Me | CarCH₂ | Me | Me | 2 | 2 |
| 1-132 | Me | 2-HOEt | Me | Me | 2 | 2 |
| 1-133 | Me | 2-FEt | Me | Me | 2 | 2 |
| 1-134 | Me | HOOCCH₂ | Me | Me | 2 | 2 |
| 1-135 | Me | NCCH₂ | Et | Me | 2 | 2 |
| 1-136 | Me | H | Et | Me | 2 | 2 |
| 1-137 | Me | H | 2-FEt | Me | 2 | 2 |
| 1-138 | Me | H | Et | Et | 2 | 2 |
| 1-139 | Me | H | Me | 2-HOEt | 2 | 3 |
| 1-140 | Me | H | Me | CarCH₂ | 2 | 3 |
| 1-141 | Me | H | Me | HOOCCH₂ | 2 | 3 |
| 1-142 | Me | H | Me | 2-FEt | 2 | 3 |
| 1-143 | Me | H | Me | 2-NH₂Et | 2 | 3 |
| 1-144 | Me | Me | Me | Me | 2 | 2 |
| 1-145 | Me | Et | Me | Me | 2 | 3 |
| 1-146 | Me | 2-HOEt | Me | Me | 2 | 3 |
| 1-147 | Me | 2-FEt | Me | Me | 2 | 3 |
| 1-148 | Me | HOOCCH₂ | Me | Me | 2 | 3 |
| 1-149 | Me | CarCH₂ | Me | Me | 2 | 3 |

TABLE 1-continued

| Cpd. No. | R¹ | R⁴ | R⁶ | R⁷ | m | n |
|---|---|---|---|---|---|---|
| 1-150 | Me | NCCH$_2$ | Me | Me | 2 | 3 |
| 1-151 | Me | H | Me | 2-SfoEt | 2 | 3 |
| 1-152 | Me | H | Me | 2-SamEt | 2 | 2 |
| 1-153 | Me | H | Me | 2-CarOEt | 2 | 3 |
| 1-154 | Me | H | Me | 2-SamEt | 2 | 3 |
| 1-155 | Me | H | Me | All | 2 | 2 |
| 1-156 | Me | H | Me | Prg | 2 | 2 |
| 1-157 | Me | H | Me | (MeCar)CH$_2$ | 2 | 2 |
| 1-158 | Me | CH$_3$C(:NH)— | Me | Me | 2 | 2 |
| 1-159 | Me | NH:CH— | Me | Me | 2 | 2 |
| 1-160 | Me | All | Me | Me | 2 | 2 |
| 1-161 | Me | Prg | Me | Me | 2 | 2 |
| 1-162 | Me | H | Me | 2-CarEt | 2 | 2 |
| 1-163 | Me | H | Me | 2-UrEt | 2 | 2 |
| 1-164 | Me | H | Me | 3-HOBu | 2 | 2 |
| 1-165 | Me | CH$_3$C(:NH)— | Me | Me | 2 | 3 |
| 1-166 | Me | H | Me | 2-CarEt | 2 | 3 |
| 1-167 | Me | NH:CH— | Me | Me | 2 | 3 |
| 1-168 | Me | H | Pr | 2-CarOEt | 2 | 3 |
| 1-169 | Me | H | Me | All | 2 | 3 |
| 1-170 | Me | H | Me | 2-(MeCar)Et | 2 | 3 |
| 1-171 | Me | H | Me | EtcCH$_2$ | 2 | 2 |
| 1-172 | Me | H | Me | 2-(AcNH)Et | 2 | 2 |
| 1-173 | Me | H | Me | 2-(AcO)Et | 2 | 2 |
| 1-174 | Me | H | Me | (diMeCar)CH$_2$ | 2 | 2 |
| 1-175 | Me | H | Me | (2-HOEtCar)CH$_2$ | 2 | 2 |
| 1-176 | Me | H | Me | (HOOCCH$_2$Car)CH$_2$ | 2 | 2 |
| 1-177 | Me | H | Me | (CarCH$_2$Car)CH$_2$ | 2 | 2 |
| 1-178 | Me | H | Me | 2-HOOCEt | 2 | 2 |
| 1-179 | Me | H | Me | (2-CarOEt)CarCH$_2$ | 2 | 2 |
| 1-180 | Me | H | Me | 2-HOPr | 2 | 2 |
| 1-181 | Me | H | Me | 2-(diMeCarO)Et | 2 | 2 |
| 1-182 | Me | H | Me | 2,3-diHOPr | 2 | 2 |
| 1-183 | Me | H | Me | 3-SfoPr | 2 | 2 |
| 1-184 | Me | H | Me | NCCH$_2$ | 2 | 3 |
| 1-185 | Me | H | Me | (MeCar)CH$_2$ | 2 | 3 |
| 1-186 | Me | H | Me | (diMeCar)CH$_2$ | 2 | 3 |
| 1-187 | Me | H | Me | (2-HOEtCar)CH$_2$ | 2 | 3 |
| 1-188 | Me | H | Me | AcCH$_2$ | 2 | 3 |
| 1-189 | Me | H | Me | 2-HOPr | 2 | 3 |
| 1-190 | Me | H | 2-HOEt | 2-HOEt | 2 | 3 |
| 1-191 | Me | H | Me | (HOOCCH$_2$Car)CH$_2$ | 2 | 3 |
| 1-192 | Me | H | Me | 2-HOOCEt | 2 | 3 |
| 1-193 | Me | H | Et | 2-HOEt | 2 | 2 |
| 1-194 | Me | H | Et | 2-CarOEt | 2 | 2 |
| 1-195 | Me | H | Et | CarCH$_2$ | 2 | 2 |
| 1-196 | Me | H | Et | HOOCCH$_2$ | 2 | 2 |
| 1-197 | Me | H | Et | 2-HOEt | 2 | 3 |
| 1-198 | Me | H | Et | 2-CarOEt | 2 | 3 |
| 1-199 | Me | H | Et | CarCH$_2$ | 2 | 3 |
| 1-200 | Me | H | Et | HOOCCH$_2$ | 2 | 3 |
| 1-201 | Me | H | Me | 2-FEt | 2 | 3 |
| 1-202 | Me | H | CarCH$_2$ | CarCH$_2$ | 2 | 2 |
| 1-203 | Me | H | 2-HOEt | HOOCCH$_2$ | 2 | 2 |
| 1-204 | Me | H | 2-HOEt | CarCH$_2$ | 2 | 2 |
| 1-205 | Me | H | 2-CarOEt | 2-HOEt | 2 | 2 |
| 1-206 | Me | H | 2-HOEt | 2-HOEt | 2 | 3 |
| 1-207 | Me | H | 2-CarOEt | 2-HOEt | 2 | 3 |
| 1-208 | Me | H | HOOCCH$_2$ | 2-HOEt | 2 | 3 |
| 1-209 | Me | H | 2-HOEt | CarCH$_2$ | 2 | 3 |
| 1-210 | Me | H | MecCH$_2$ | Me | 2 | 3 |
| 1-211 | Me | H | EtcCH$_2$ | Me | 2 | 3 |
| 1-212 | Me | H | EtcCH$_2$ | Me | 2 | 3 |
| 1-213 | Me | H | 2-MeOEt | Me | 2 | 3 |
| 1-214 | Me | H | 2-AcOEt | Me | 2 | 3 |
| 1-215 | Me | 3-SfoPr | Me | Me | 2 | 2 |
| 1-216 | Me | SamCH$_2$ | Me | Me | 2 | 2 |
| 1-217 | Me | 2-NH$_2$Et | Me | Me | 2 | 2 |
| 1-218 | Me | H | 2-HOEt | 2-NH$_2$Et | 2 | 2 |
| 1-219 | Me | 2-(MeNH)Et | Me | Me | 2 | 2 |
| 1-220 | Me | 2-(diMeN)Et | Me | Me | 2 | 2 |
| 1-221 | Me | H | 2-(MeNH)Et | Me | 2 | 2 |
| 1-222 | Me | H | 2-(diMeN)Et | Me | 2 | 2 |
| 1-223 | Me | H | 2-(MeNH)Et | Me | 2 | 3 |
| 1-224 | Me | H | 2-(diMeN)Et | Me | 2 | 3 |
| 1-225 | H | H | Me | 3-SfoPr | 2 | 2 |
| 1-226 | Me | H | Me | 3-SfoPr | 2 | 3 |

TABLE 2

| Cpd No. | R¹ | R² | R⁴ | p | Z⁺ |
|---|---|---|---|---|---|
| 2-1 | H | H | H | 1 | 1-Me-4-Pyr⁺ |
| 2-2 | H | H | H | 1 | 1-Me-3-Pyr⁺ |
| 2-3 | H | H | H | 1 | 1-Me-2-Pyr⁺ |
| 2-4 | H | H | H | 2 | 1,1-diMe-2-Pyrd⁺ |
| 2-5 | H | H | H | 0 | 1-Me-3-Qnu⁺ |
| 2-6 | H | H | H | 0 | 1,1-diMe-3-Pyrd⁺ |
| 2-7 | H | H | H | 0 | 1,1-diMe-4-Pip⁺ |
| 2-8 | H | H | H | 0 | 1,1-diMe-3-Pip⁺ |
| 2-9 | H | H | H | 1 | 1,1-diMe-2-Pyrd⁺ |
| 2-10 | H | H | H | 1 | 1-Et-1-Me-2-Pyrd⁺ |
| 2-11 | H | Me | H | 0 | 1,1-diMe-4-Pip⁺ |
| 2-12 | H | H | H | 1 | 1,1-diMe-3-Azt⁺ |
| 2-13 | H | H | H | 1 | 1,3-diMe-4-Imid⁺ |
| 2-14 | H | H | H | 2 | 3,4-diMe-5-Thiz⁺ |
| 2-15 | H | H | H | 1 | 3-Me-4-Thiz⁺ |
| 2-16 | H | H | H | 1 | 1-Me-3-Pyzn⁺ |
| 2-17 | H | H | H | 1 | 1-Me-4-Pym⁺ |
| 2-18 | H | H | H | 2 | 4-Me-3-Thdz⁺ |
| 2-19 | H | H | H | 1 | 4,4-diMe-2-Mor⁺ |
| 2-20 | H | H | H | 1 | 1,1-diMe-4-Pip⁺ |
| 2-21 | H | H | H | 2 | 1,1-diMe-4-Pip⁺ |
| 2-22 | H | H | H | 2 | 1-Me-2-Pyr⁺ |
| 2-23 | H | H | H | 1 | 1,1-diMe-2-Pip⁺ |
| 2-24 | H | H | H | 0 | 1-(2-HOEt)-1-Me-3-Pyrd⁺ |
| 2-25 | H | H | H | 0 | 1-(2-CarEt)-1-Me-3-Pyrd⁺ |
| 2-26 | H | H | H | 0 | 1-(2-FEt)-1-Me-3-Pyrd⁺ |
| 2-27 | H | H | H | 0 | 1-(2-NCEt)-1-Me-3-Pyrd⁺ |
| 2-28 | H | H | H | 0 | 1-(2-CarOEt)-1-Me-3-Pyrd⁺ |
| 2-29 | H | H | H | 0 | 1-(2-SfoEt)-1-Me-3-Pyrd⁺ |
| 2-30 | H | H | H | 0 | 1,1-diMe-4-HO-3-Pyrd⁺ |
| 2-31 | H | H | H | 0 | 1,1-diMe-4-F-3-Pyrd⁺ |
| 2-32 | H | H | H | 1 | 4-Et-4-Me-2-Mor⁺ |
| 2-33 | H | H | H | 0 | 1,1-diMe-3-Azt⁺ |
| 2-34 | H | H | H | 0 | 1-(2-HOEt)-1-Me-3-Azt⁺ |
| 2-35 | H | H | H | 0 | 1-(2-FEt)-1-Me-3-Azt⁺ |
| 2-36 | H | H | H | 0 | 1-(CarCH₂)-1-Me-3-Azt⁺ |
| 2-37 | H | H | H | 0 | 1-(2-CarEt)-1-Me-3-Azt⁺ |
| 2-38 | H | H | H | 0 | 1-(2-CarOEt)-1-Me-3-Azt⁺ |
| 2-39 | H | H | H | 0 | 1-(HOOCCH₂)-1-Me-3-Azt⁺ |
| 2-40 | H | H | H | 0 | 1-All-1-Me-3-Azt⁺ |
| 2-41 | H | H | H | 0 | 1-Prg-1-Me-3-Azt⁺ |
| 2-42 | H | H | H | 0 | 1-(2-MeOEt)-1-Me-3-Azt⁺ |
| 2-43 | H | H | H | 0 | 1-(AcCH₂)-1-Me-3-Azt⁺ |
| 2-44 | H | H | H | 0 | 1-(2-NH₂Et)-1-Me-3-Azt⁺ |
| 2-45 | H | H | H | 0 | 1-(2-SfoEt)-1-Me-3-Azt⁺ |
| 2-46 | H | H | H | 0 | 1-(HOOCCH₂)-1-Me-3-Pyrd⁺ |
| 2-47 | Me | H | H | 1 | 1-Me-4-Pyr⁺ |
| 2-48 | Me | H | H | 1 | 1-Me-3-Pyr⁺ |
| 2-49 | Me | H | H | 1 | 1-Me-2-Pyr⁺ |
| 2-50 | Me | H | H | 2 | 1,1-diMe-2-Pyrd⁺ |
| 2-51 | Me | H | H | 0 | 1-Me-3-Qnu⁺ |
| 2-52 | Me | H | H | 0 | 1,1-diMe-3-Pyrd⁺ |
| 2-53 | Me | H | H | 0 | 1,1-diMe-4-Pip⁺ |
| 2-54 | Me | H | H | 0 | 1,1-diMe-3-Pip⁺ |
| 2-55 | Me | H | H | 1 | 1,1-diMe-2-Pyrd⁺ |
| 2-56 | Me | H | H | 1 | 1-Et-1-Me-2-Pyrd⁺ |
| 2-57 | Me | Me | H | 0 | 1,1-diMe-4-Pip⁺ |
| 2-58 | Me | H | H | 1 | 1,1-diMe-3-Azt⁺ |
| 2-59 | Me | H | H | 1 | 1,3-diMe-4-Imid⁺ |
| 2-60 | Me | H | H | 2 | 3,4-diMe-5-Thiz⁺ |
| 2-61 | Me | H | H | 1 | 3-Me-4-Thiz⁺ |
| 2-62 | Me | H | H | 1 | 1-Me-3-Pyzn⁺ |
| 2-63 | Me | H | H | 1 | 1-Me-4-Pym⁺ |
| 2-64 | Me | H | H | 2 | 4-Me-3-Thdz⁺ |
| 2-65 | Me | H | H | 1 | 4,4-diMe-2-Mor⁺ |
| 2-66 | Me | H | H | 1 | 1,1-diMe-4-Pip⁺ |
| 2-67 | Me | H | H | 2 | 1,1-diMe-4-Pip⁺ |
| 2-68 | Me | H | H | 2 | 1-Me-2-Pyr⁺ |
| 2-69 | Me | H | H | 1 | 1,1-diMe-2-Pip⁺ |
| 2-70 | Me | H | H | 0 | 1-(2-HOEt)-1-Me-3-Pyrd⁺ |
| 2-71 | Me | H | H | 0 | 1-(2-CarEt)-1-Me-3-Pyrd⁺ |
| 2-72 | Me | H | H | 0 | 1-(2-FEt)-1-Me-3-Pyrd⁺ |
| 2-73 | Me | H | H | 0 | 1-(2-NCEt)-1-Me-3-Pyrd⁺ |
| 2-74 | Me | H | H | 0 | 1-(2-CarOEt)-1-Me-3-Pyrd⁺ |
| 2-75 | Me | H | H | 0 | 1-(2-SfoEt)-1-Me-3-Pyrd⁺ |
| 2-76 | Me | H | H | 0 | 1,1-diMe-4-HO-3-Pyrd⁺ |
| 2-77 | Me | H | H | 0 | 1,1-diMe-4-F-3-Pyrd⁺ |
| 2-78 | Me | H | H | 1 | 4,4-diMe-2-Mor⁺ |
| 2-79 | Me | H | H | 0 | 1,1-diMe-3-Azt⁺ |
| 2-80 | Me | H | H | 0 | 1-(2-HOEt)-1-Me-3-Azt⁺ |
| 2-81 | Me | H | H | 0 | 1-(2-FEt)-1-Me-3-Azt⁺ |
| 2-82 | Me | H | H | 0 | 1-(CarCH₂)-1-Me-3-Azt⁺ |
| 2-83 | Me | H | H | 0 | 1-(2-CarEt)-1-Me-3-Azt⁺ |
| 2-84 | Me | H | H | 0 | 1-(2-CarOEt)-1-Me-3-Azt⁺ |
| 2-85 | Me | H | H | 0 | 1-(HOOCCH₂)-1-Me-3-Azt⁺ |
| 2-86 | Me | H | H | 0 | 1-All-1-Me-3-Azt⁺ |
| 2-87 | Me | H | H | 0 | 1-Prg-1-Me-3-Azt⁺ |
| 2-88 | Me | H | H | 0 | 1-(2-MeOEt)-1-Me-3-Azt⁺ |
| 2-89 | Me | H | H | 0 | 1-(AcCH₂)-1-Me-3-Azt⁺ |
| 2-90 | Me | H | H | 0 | 1-(2-NH₂Et)-1-Me-3-Azt⁺ |
| 2-91 | Me | H | H | 0 | 1-(2-SfoEt)-1-Me-3-Azt⁺ |
| 2-92 | Me | H | H | 0 | 1-(HOOCCH₂)-1-Me-3-Pyrd⁺ |

TABLE 3

| Cpd. No. | R¹ | R² | R⁴ | p | Rᵃ | Rᵇ | Rᶜ |
|---|---|---|---|---|---|---|---|
| 3-1 | H | H | H | 2 | Me | Me | Me |
| 3-2 | H | H | H | 2 | Me | Me | 2-HOEt |
| 3-3 | H | H | H | 3 | Me | Me | Me |
| 3-4 | H | H | H | 2 | Me | Me | HOOCCH₂ |
| 3-5 | H | H | H | 2 | Me | Me | CarCH₂ |
| 3-6 | H | H | Me | 2 | Me | Me | Me |
| 3-7 | H | H | 2-HOEt | 2 | Me | Me | Me |
| 3-8 | H | H | HOOCCH₂ | 2 | Me | Me | Me |
| 3-9 | H | H | CarCH₂ | 2 | Me | Me | Me |
| 3-10 | Me | H | H | 2 | Me | Me | Me |
| 3-11 | Me | H | H | 2 | Me | Me | 2-HOEt |
| 3-12 | Me | H | H | 3 | Me | Me | Me |
| 3-13 | Me | H | H | 2 | Me | Me | HOOCCH₂ |
| 3-14 | Me | H | H | 2 | Me | Me | CarCH₂ |
| 3-15 | Me | H | Me | 2 | Me | Me | Me |
| 3-16 | Me | H | 2-HOEt | 2 | Me | Me | Me |
| 3-17 | Me | H | HOOCCH₂ | 2 | Me | Me | Me |
| 3-18 | Me | H | CarCH₂ | 2 | Me | Me | Me |

TABLE 4

| Cpd No. | R¹ | Rᵈ | Rᵉ | Rᶠ | R⁶ |
|---|---|---|---|---|---|
| 4-1 | H | H | Me | H | Me |
| 4-2 | H | Me | H | H | Me |
| 4-3 | H | Me | H | Me | Me |
| 4-4 | H | H | Me | H | 2-HOEt |
| 4-5 | H | H | Me | H | 2-CarOEt |
| 4-6 | H | H | Me | H | HOOCCH₂ |
| 4-7 | H | H | Me | H | CarCH₂ |
| 4-8 | H | H | Me | H | 2-MeOEt |
| 4-9 | Me | H | Me | H | Me |
| 4-10 | Me | Me | H | H | Me |
| 4-11 | Me | Me | H | Me | Me |
| 4-12 | Me | H | Me | H | 2-HOEt |
| 4-13 | Me | H | Me | H | 2-CarOEt |
| 4-14 | Me | H | Me | H | HOOCCH₂ |
| 4-15 | Me | H | Me | H | CarCH₂ |
| 4-16 | Me | H | Me | H | 2-MeOEt |

TABLE 5

| Cpd. No. | R¹ | R⁶ |
|---|---|---|
| 5-1 | H | Me |
| 5-2 | H | 2-HOEt |
| 5-3 | H | CarCH₂ |
| 5-4 | H | 2-CarOEt |
| 5-5 | H | HOOCCH₂ |
| 5-6 | Me | Me |
| 5-7 | Me | 2-HOEt |
| 5-8 | Me | CarCH₂ |
| 5-9 | Me | 2-CarOEt |
| 5-10 | Me | HOOCCH₂ |

TABLE 6

| Cpd. No. | R¹ | (A) | (B) | n |
|---|---|---|---|---|
| 6-1 | H | — | —CH₂—NH— | 2 |
| 6-2 | H | —CH₂CH₂— | —CH₂—NH— | 2 |
| 6-3 | H | —CH₂— | —NH— | 3 |
| 6-4 | H | — | —CH₂—NH— | 3 |

TABLE 6-continued

| Cpd. No. | R¹ | (A) | (B) | n |
|---|---|---|---|---|
| 6-5 | Me | — | —CH₂—NH— | 2 |
| 6-6 | Me | —CH₂CH₂— | —CH₂—NH— | 2 |
| 6-7 | Me | —CH₂— | —NH— | 3 |
| 6-8 | Me | — | —CH₂—NH— | 3 |

Of the compounds listed above, the most preferred ones are Compounds No.:

1-113. 2-[2-(4,4-Dimethyl-1-piperaziniocarbonyl)-pyrrolidin-4-ylthio]-6-(1-hydroxyethyl)-1-methyl-1-carbapen-2-em-3-carboxylate, especially the (1R,5S,6S)-2-[(2S,4S)-2-(4,4-dimethyl-1-piperaziniocarbonyl)-pyrrolidin-4-ylthio]-6-[(1R)-1-hydroxyethyl]-1-methyl-1-carbapen-2-em-3-carboxylate isomer, and its fluorosulfonate, hemisulfate and hydrochloride;

1-114. 2-[2-(4,4-Dimethyl-1-homopiperaziniocarbonyl)-pyrrolidin-4-ylthio]-6-(1-hydroxyethyl)-1-methyl-1-carbapen-2-em-3-carboxylate, especially the (1R,5S,6S)-2-[(2S,4S)-2-(4,4-dimethyl-1-homopiperaziniocarbonyl)-pyrrolidin-4-ylthio]-6-[(1R)-1-hydroxyethyl]-1-methyl-1-carbapen-2-em-3-carboxylate isomer, and its hemisulfate and hydrochloride;

1-116. 2-{2-[4-(2-Hydroxyethyl)-4-methyl-1-piperaziniocarbonyl]pyrrolidin-4-ylthio}-6-(1-hydroxyethyl)-1-methyl-1-carbapen-2-em-3-carboxylate, especially the (1R,5S,6S)-2-{(2S,4S)-2-[4-(2-hydroxyethyl)-4-methyl-1-piperaziniocarbonyl]pyrrolidin-4-ylthio}-6-[(1R)-1-hydroxyethyl]-1-methyl-1-carbapen-2-em-3-carboxylate isomer, and its fluorosulfate, hemisulfate and hydrochloride;

1-117. 2-[2-(4-Carbamoylmethyl-4-methyl-1-piperaziniocarbonyl)pyrrolidin-4-ylthio]-6-(1-hydroxyethyl)-1-methyl-1-carbapen-2-em-3-carboxylate, especially its (1R,5S,6S)-2-[(2S,4S)-2-(4-carbamoylmethyl-4-methyl-1-piperaziniocarbonyl)pyrrolidin-4-ylthio]-6-[(1R)-1-hydroxyethyl]-1-methyl-1-carbapen-2-em-3-carboxylate isomer, and its hemisulfate and hydrochloride;

1-119. 2-[2-(4-Carbamoylmethyl-4-methyl-1-piperaziniocarbonyl)pyrrolidin- 4-ylthio]-6-(1-hydroxyethyl)-1-methyl-1-carbapen-2-em-3-carboxylate, especially its (1R,5S,6S)-2-[(2S,4S)-2-(4-carbamoymethyl-4-methyl-1-piperaziniocarbonyl)pyrrolidin-4-ylthio]-6-[(1R)-1-hydroxyethyl]-1-methyl-1-carbapen-2-em-3-carboxylate isomer;

1-121. 2-{2-[4-(2-Carbamoyloxyethyl-4-methyl-1-piperaziniocarbonyl]pyrrolidin-4-ylthio}-6-(1-hydroxyethyl)-1-methyl-1-carbapen-2-em-3-carboxylate, especially its (1R,5S,6S)-2-{(2S,4S)-2-[4-(2-carbamoyloxyethyl)-4-methyl-1-piperaziniocarbonyl]pyrrolidin-4-ylthio}-6-[(1R)-1-hydroxyethyl]-1-methyl-1-carbapen-2-em-3-carboxylate isomer, and its fluorosulfonate, hemisulfate and hydrochloride;

1-139. 2-{2-[4-(2-Hydroxyethyl)-4-methyl-1-homopiperaziniocarbonyl]pyrrolidin-4-ylthio}-6-(1-hydroxyethyl)-1-methyl-1-carbapen-2-em-3-carboxylate, especially its (1R,5S,6S)-2-{(2S,4S)-2-[4-(2-hydroxyethyl)-4-methyl-1-homopiperaziniocarbonyl]pyrrolidin-4-ylthio}-6-[(1R)-1-hydroxyethyl]-1-methyl-1-carbapen-2-em-3-carboxylate isomer, and its hemisulfate and hydrochloride;

1-140. 2-[2-(4-Carbamoylmethyl-4-methyl-1-homopiperaziniocarbonyl)pyrrolidin-4-ylthio]-6-(1-hydroxyethyl)-1-methyl-1-carbapen-2-em-3-carboxylate, especially its (1R,5S,6S)-2-[(2S,4S)-2-(4-carbamoylmethyl-4-methyl-4-methyl-1-homopiperaziniocarbonyl)pyrrolidin-4-ylthio]-6-[(1R)-1-hydroxyethyl]-1-methyl-1-carbapen-2-em-3-carboxylate isomer, and its hemisulfate and hydrochloride;

1-141. 2-[2-(4-Carboxymethyl-4-methyl-1-homopiperaziniocarbonyl)pyrrolidin-4-ylthio]-6-(1-hydroxyethyl)-1-methyl-1-carbapen-2-em-3-carboxylate, especially its (1R,5S,6S)-2-[(2S,4S)-2-(4-carbamoymethyl-4-methyl-1-homopiperaziniocarbonyl)pyrrolidin-4-ylthio]-6-[(1R)-1-hydroxyethyl]-1-methyl-1-carbapen-2-em-3-carboxylate isomer;

1-153. 2-{2-[4-(2-Carbamoyloxyethyl)-4-methyl-1-homopiperaziniocarbonyl]pyrrolidin-4-ylthio}-6-(1-hydroxyethyl)-1-methyl-1-carbapen-2-em-3-carboxylate, especially its (1R,5S,6S)-2-{(2S,4S)-2-[4-(2-carbamoyloxyethyl)-4-methyl-1-homopiperaziniocarbonyl]pyrrolidin-4-ylthio}-6-[(1R)-1-hydroxyethyl]-1-methyl-1-carbapen-2-em-3-carboxylate isomer, and its hemisulfate and hydrochloride;

1-183. 6-(1-Hydroxyethyl)-1-methyl-2-{2-[4-methyl-4-(3-sulfopropyl)-1-piperaziniocarbonyl]pyrrolidin-4-ylthio}-1-carbapen-2-em-3-carboxylate, especially its (1R,5S,6S)-6-[(1R)-1-hydroxyethyl]-1-methyl-2-{(2S,4S)-2-[4-methyl-4-(3-sulfopropyl)-1-piperaziniocarbonyl]pyrrolidin-4-ylthio}-1-carbapen-2-em-3-carboxylate isomer; and 4-9. 6-(1-Hydroxyethyl)-1-methyl-2-[2-(3,4,4-trimethyl-1-piperaziniocarbonyl)pyrrolidin-4-ylthio]-1-carbapen-2-em-3-carboxylate, especially its (1R,5S,6S)-6-[(1R)-1-hydroxyethyl]-1-methyl-2-[(2S,4S)-2-(3,4,4-trimethyl-1-piperaziniocarbonyl)pyrrolidin-4-ylthio]-1-carbapen-2-em-3-carboxylate isomer, and its hydrochloride.

The compounds of the present invention may be prepared by a variety of methods well known in the art for the preparation of compounds of this type. For example, they may be prepared by reacting a compound of formula (IV):

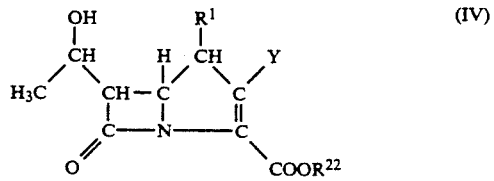

(in which: R¹ is as defined above; Y represents a group of formula —OR²¹ or —SO—R²³; R²¹ represents an alkylsulfonyl group, an arylsulfonyl group, a dialkylphosphoryl group or a diarylphosphoryl group; R²² represents a carboxy-protecting group; and R²³ represents an alkyl group having from 1 to 4 carbon atoms, a halogenated alkyl group having from 1 to 4 carbon atoms; a 2-acetamidoethyl group; a 2-acetamidovinyl group; an aryl group which has from 6 to 10 ring carbon atoms and which is unsubstituted or has at least one substituent selected from the group consisting of halogen atoms, C₁–C₃ alkyl groups, C₁–C₃ alkoxy groups, C₂–C₅ alkoxycarbonyl groups, nitro groups, carbamoyl groups, mono(C₁–C₃ alkyl)-carbamoyl groups, di(C₁–C₃ alkyl)carbamoyl groups, hydroxy groups and cyano groups; or an aromatic heterocyclic group having 5 or 6 ring atoms, of which 1 is a hetero-atom selected from the group consisting of nitrogen, oxygen and sulfur hetero-atoms and 0 or 1 is an additional nitrogen atom, said heterocyclic group being unsubstituted or being substituted by at least one substituent selected from the group consisting of halogen atoms and $C_1$–$C_3$ alkyl groups) with a compound of formula (V):

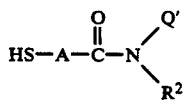

(In which: A and $R^2$ are as defined above; and Q' represents any of the groups represented by Q or any such group in which the quaternary nitrogen atom is replaced by an unquaternized nitrogen atom and in which, where Q' represents a group containing a quaternary nitrogen atom, the compound also includes a balancing anion). That is Q' may represent any of the groups represented by Q together with a balancing anion or it may represent:

(i') a group of formula —B—$NR^8R^9$, wherein: B, $R^8$ and $R^9$ are as defined above;

(ii') a heterocyclic group having from 4 to 10 ring atoms in a single or bridged ring, one of said ring atoms being a substituted nitrogen atom of formula >$NR^{11}$, wherein $R^{11}$ is as defined above; and 0, 1 or 2 of said ring atoms being selected from the group consisting of nitrogen, oxygen and sulfur hetero-atoms, the remainder being carbon atoms, said heterocyclic group being otherwise unsubstituted or having at least one substituent selected from the group consisting of substituents (c), defined above;

(iii') an alkyl group having from 1 to 6 carbon atoms and substituted by a heterocyclic group as defined in (ii') above; or (iv') an alkyl group having from 1 to 6 carbon atoms and substituted by an aromatic heterocyclic group having from 5 to 8 ring atoms, one of said ring atoms being a nitrogen atom;

$R^2$ and Q', together with the nitrogen atom to which they are attached, represent a group of formula (II'):

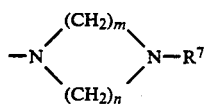

wherein m, n and $R^7$ are as defined above;

and the carbon atoms of said group of formula (II') are unsubstituted or they are substituted by at least one substituent selected from the group consisting of alkyl groups having from 1 to 6 carbon atoms and oxygen atoms (to form an oxo group).

This reaction gives a compound of formula (I'):

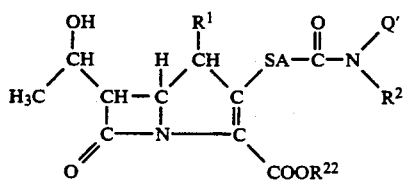

in which $R^1$, $R^2$, $R^3$, A and Q' are as defined above in which, where Q' represents a group containing a quaternary nitrogen atom, the compound also includes a balancing anion. Where Q' represents one of the groups represented by Q, this is a compound of the present invention. Where Q' represents a group containing an unquaternized nitrogen atom, then this nitrogen atom is quaternized in a further step. If required, the balancing anion and the carboxy-protecting group may be removed to give a compound of formula (I) in which $R^3$ represents a negative charge, i.e. a compound of formula (I''):

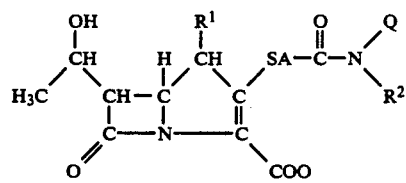

in which $R^1$, $R^2$ and Q are as defined above.

In one embodiment of this process, the first step comprises reacting a compound of formula (IVa):

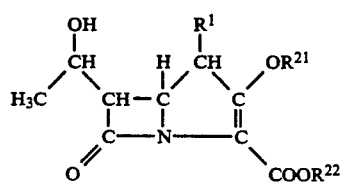

(in which: $R^1$, $R^2{}_1$ and $R^{22}$ are as defined above) with the compound of formula (V), to give the compound of formula (I').

The compound of formula (IVa) used as a starting material in these reactions may be prepared by reacting a compound of formula (VI):

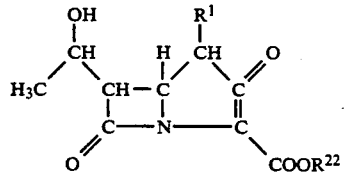

(in which: $R^1$ $R^{22}$ are as defined above) with an alkylsulfonic acid, an arylsulfonic acid, a dialkylphosphoric acid or a diarylphosphoric acid or with a reactive derivative thereof, especially an alkylsulfonic acid anhydride, an arylsulfonic acid anhydride, a dialkylphosphoryl halide or a diarylphosphoryl halide, preferably in the presence of a base. The next step in the reaction [the reaction of the resulting compound of formula (IVa) with the mercapto compound of formula (V)] is preferably effected without intermediate isolation of the compound of formula (IVa) and is carried out in the same reaction medium.

Suitable acid derivatives for use in the reaction preparing the compound of formula (IVa) from the compound of formula (VI) include: alkanesulfonic acid anhydrides, such as methanesulfonic acid anhydride, trifluoromethanesulfonic acid anhydride or ethanesulfonic acid anhydride; arylsulfonic acid anhydrides, such as benzenesulfonic acid anhydride or p-toluenesulfonic acid anhydride; dialkylphosphoryl halides, such as dimethylphosphoryl chloride or diethylphosphoryl chloride; and diarylphosphoryl halides, such as diphenylphosphoryl chloride or dipenylphosphoryl bromide. Of these, p-toluenesulfonic acid anhydride or diphenylphosphoryl chloride are particularly preferred.

The reaction is normally and preferably effected in a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as 1,2-dichloroethane or chloroform; nitriles, such as acetonitrile; and amides, especially fatty acid amides, such as N,N-dimethylformamide or N,N-dimethylacetamide. There is likewise no particular restriction on the nature of the base employed in the reaction, provided that it does not affect any other part of the compound, in particular the β-lactam ring, and examples of suitable bases include: organic bases, especially tertiary amines, such as triethylamine, diisopropylethylamine or 4-dimethylaminopyridine.

The reaction can take place over a wide range of temperatures, and the precise reaction temperature is not critical to the invention. However, in order to prevent any side reactions, it is desirable for the reaction to be carried out at a relatively low temperature. In general, we find it convenient to carry out the reaction at a temperature of from −20° C. to +40° C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

The compound of formula (IVa) thus obtained does not need to be separated from the reaction mixture; instead, the entire reaction mixture can be treated with the mercapto compound of formula (V) in the presence of a base. As with the previous step, there is no particular restriction on the nature of the base employed in the reaction, provided that it does not affect any other part of the compound, in particular the β-lactam ring, and examples of suitable bases include: organic bases, such as triethylamine or diisopropylamine; and inorganic bases, especially alkali metal carbonates, such as potassium carbonate or sodium carbonate.

The reaction can take place over a wide range of temperatures, and the precise reaction temperature is not critical to the invention. In general, we find it convenient to carry out the reaction at a temperature of from −20° C. to room temperature. The time required for the reaction may also vary widely, depending on many factors, notably the reaction temperature and the nature of the reagents. However, provided that the reaction is effected under the preferred conditions outlined above, a period of from 30 minutes to 5 days will usually suffice.

After completion of the reaction, the desired compound of formula (I') can be recovered from the reaction mixture by conventional means. For example, by removing the reaction medium or solvent and then purifying the compound by such conventional techniques as recrystallization, reprecipitation or the various chromatography techniques, e.g. column chromatography or preparative thin layer chromatography. Alternatively, it can be purified by direct reprecipitation of the desired compound from the reaction mixture.

If desired, the reaction mixture can be subjected to the subsequent step of removing the carboxy-protecting group without intermediate separation of the compound of formula (I'), or the removal of the protecting group may be accomplished after separation of the compound, as desired. The reaction employed to remove the protecting group will, of course, depend on the nature of the protecting group and may be carried out using methods well known in the art for the removal of carboxy-protecting groups from compounds of this type.

For example, where the carboxy-protecting group, $R^{22}$, is a group capable of removal by reduction, the reaction is preferably effected by contacting the compound of formula (I') wherein $R^{22}$ represents such a carboxy-protecting group with a reducing agent. Examples of carboxy-protecting groups which may be removed in this way include the haloalkyl, aralkyl (including benzhydryl) groups. Examples of preferred reducing agents which may be employed in this reaction include: zinc and acetic acid, if the carboxy-protecting group is a haloalkyl group, such as the 2,2-dibromoethyl or 2,2,2-trichloroethyl group; or a catalytic reagent (such as hydrogen and palladium-on-carbon) or an alkali metal sulfide (such as sodium sulfide or potassium sulfide), if the carboxy-protecting group is an aralkyl group or a benzhydryl group. The reaction is normally and preferably carried out in the presence of a solvent, the nature of which is not critical, provided that it has no adverse effect upon the reaction and that is can dissolve the reagents, at least to some extent. Examples of suitable solvents include: alcohols, such as methanol or ethanol; ethers, such as tetrahydrofuran or dioxan; fatty acids, such as acetic acid; or a mixture of any one of more of these organic solvents with water.

The reaction will take place over a wide range of temperatures, and the precise reaction temperature chosen is not critical to the invention. In general, we find it convenient to carry out the reaction at a temperature in the range of from 0° C. to about room temperature. The time required for the reaction may likewise vary widely, depending on many factors, notably the reaction temperature and the nature of the reagents. However, in most cases, a period of from 5 minutes to 12 hours will normally suffice.

After completion of the reaction, the resulting compound can be recovered from the reaction mixture by conventional means. For example, any impurities separated from the reaction mixture may be removed by filtration, after which the solvent may be removed by distillation, to obtain the desired compound.

The compound thus obtained can, if necessary, be further purified by conventional means such as recrystallization or the various chromatography techniques, notably preparative thin layer chromatography or column chromatography.

If desired, the carboxy group contained in the compound obtained after removal of the carboxy-protecting group can be converted by known methods into an ester group which is capable of being hydrolyzed under physiological conditions. If $R^3$ is an ester group which can be hydrolyzed physiologically, for example, an alkanoyloxyalkyl group (such as a pivaloyloxymethyl or acetoxymethyl group), an alkoxycarbonyloxyalkyl group [such as a 1-(ethoxycarbonyloxy)ethyl or 1-(isopropoxycarbonyloxy)ethyl group], the phthalidyl group, the indanyl group, the methoxymethyl group or the 2-oxo-5-methyl-1,3-dioxolen-4-ylmethyl group, the compound of formula (I) can be hydrolyzed in vivo under physiological condition and, therefore, it can be directly administered to patients without any need for deprotection.

Where Q' in the above formulae represents an unquaternized nitrogen atom, it is necessary at some stage to quaternize it. This is preferably effected after the reaction of the compound of formula (IVa) with the mercapto compound of formula (V) to give the compound of formula (I'), but before removal of any carboxy-protecting group. Quaternization may be effected under conventional conditions by reacting the compound of formula (I') in which Q represents an unquaternized nitrogen atom with a compound of formula RX, in which R represents any one of the groups $R^6$, $R^{10}$ or $R^{12}$, defined above and X represents a halogen atom (for example a chlorine atom, a bromine atom or an iodine atom), an alkanesulfonyloxy, arylsulfonyloxy, halosulfonyloxy or alkoxysulfonyloxy group (for example a methanesulfonyloxy group, a toluenesulfonyloxy group, a trifluoromethanesulfonyloxy group, a fluorosulfonyloxy or a methoxysulfonyloxy group). The reaction may be carried out in the presence or absence of a solvent. Where a solvent is employed, its nature is not critical, provided that it has no adverse effect upon the reaction and that it can dissolve the reagents, at least to some extent. Examples of suitable solvents include: halogenated hydrocarbons, especially halogenated aliphatic hydrocarbons, such as methylene chloride, 1,2-dichloroethane or chloroform; nitriles, such as acetonitrile; ethers, such as tetrahydrofuran; esters, such as ethyl acetate; and amides, especially fatty acid amides, such as N,N-dimethylformamide or N,N-dimethylacetamide. The reaction will take place over a wide range of temperatures, and the precise reaction temperature chosen is not critical to the invention. In general, we find it convenient to carry out the reaction at a temperature in the range of from $-20°$ C. to $100°$ C. The time required for the reaction may likewise vary widely, depending on many factors, notably the reaction temperature and the nature of the reagents.

After completion of the reaction, the desired compound of formula (I') can be obtained from the reaction mixture by the conventional means. For example, the reaction solution or the solvent of the reaction mixture may simply be distilled off; the compound thus obtained can, if necessary, be purified by conventional means such as recrystallization, reprecipitation or the various chromatography techniques, notably column chromatography or preparative thin layer chromatography. Alternatively, it can be purified by precipitating it directly from the reaction solution. If desired, the reaction solution can be used, without intermediate separation of the compound of formula (I'), for the succeeding deprotection of the carboxy-protecting group, as described above.

In an alternative embodiment of the process of the present invention, a compound of formula (IVb):

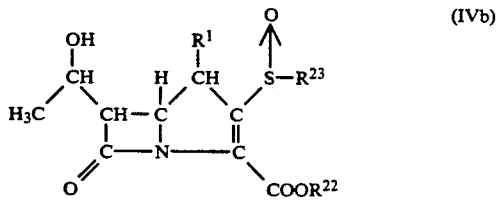

(IVb)

(in which $R^1$, $R^{22}$ and $R^{23}$ are as defined above) is reacted with said compound of formula (V), to give the compound of formula (I').

In the compound of formula (IVb), where $R^{23}$ represents an alkyl group, this may be a straight or branched chain alkyl group having from 1 to 4, preferably from 1 to 3, carbon atoms, for example a methyl, ethyl, propyl or isopropyl group. Where it represents a halogenated alkyl group, the alkyl part may be any of the alkyl groups defined and exemplified above which is substituted by at least one, and preferably from 1 to 3, halogen atoms; examples of such groups include the various fluoromethyl, chloromethyl, fluoroethyl, chloroethyl, fluoropropyl, difluoromethyl, difluoroethyl, dichloroethyl, trifluoromethyl and trifluoroethyl groups. Where it is an optionally substituted aryl group, the aryl group itself may be, for example, a phenyl or naphthyl group, and it may be unsubstituted or it may have at least one, and preferably from 1 to 3 substituents, such as: halogen atoms, e.g. the fluorine, chlorine or bromine atoms; alkyl groups, e.g. the methyl, ethyl, propyl or isopropyl groups; alkoxy groups, e.g. the methoxy, ethoxy, propoxy or isopropoxy groups; alkoxycarbonyl groups, e.g. the methoxycarbonyl, ethoxycarbonyl or t-butoxycarbonyl groups; or the nitro, carbamoyl, methylcarbamoyl, ethylcarbamoyl, dimethylcarbamoyl, diethylcarbamoyl, hydroxy or cyano groups. Where it is an optionally substituted aromatic heterocyclic group, this is preferably a pyridyl or pyrimidinyl group, and the heterocyclic group may be unsubstituted or it may be substituted by at least one, and preferably from 1 to 3, substituents, such as: halogen atoms, e.g. the fluorine, chlorine or bromine atoms; or alkyl groups, e.g. the methyl, ethyl, propyl or isopropyl. In the case of the substituted aryl and aromatic heterocyclic groups, where there are two or more substituents, these may be the same or different.

The compound of formula (IVb), which is a starting material in this embodiment of the process, can be synthesized by the procedure which has been claimed in Japanese Patent Application Kokai No. Sho 62-30781.

The reaction of the compound of formula (IVb) with the mercapto compound of formula (V) to prepare the compound of formula (I') is effected in the presence of a base and normally and preferably in a suitable solvent, the nature of which is not critical, provided that it has no adverse effect upon the reaction and that it can dissolve the reagents, at least to some extent. Examples of suitable solvents include: ethers, such as tetrahydrofuran; nitriles, such as acetonitrile; amides, such as dimethylformamide; sulfoxides, such as dimethyl sulfoxide; water; or a mixture of any two or more of these solvents. There is no particular limitation on the nature of the base employed, provided that it does not affect any other parts of the compounds, in particular the $\beta$-lactam ring; suitable bases include: organic bases, such as diisopropylethylamine, triethylamine, N-methylpyridine or 4-dimethylaminopyridine; and inorganic bases, especially alkali metal carbonates and hydrogencarbonates, such as potassium carbonate or sodium hydrogencarbonate. The reaction will take place over a wide range of temperatures, and the precise reaction temperature chosen is not critical to the invention. However, in order to prevent any side reactions, it is recommended that the reaction should be carried out at a relatively low temperature. In general, we find it convenient to carry out the reaction at a temperature in the range of from $-20°$ C. to $40°$ C. The time required for the reaction may likewise vary widely, depending on many factors, notably the reaction temperature and the nature of the reagents. However, in most cases, a period of from 5 minutes to 5 days will normally suffice.

After completion of the reaction, the desired compound of formula (I') can be obtained by conventional means.

If necessary, the compound of formula (I') can be then be subjected to deprotection as previously described.

The mercapto compounds of formula (V), the starting materials, can be prepared by the procedure described in Japanese Patent Application Kokai No. Hei 2-28180 and Japanese Patent Application Kokai No. Hei 2-3687.

BIOLOGICAL ACTIVITY

The compounds of the present invention exhibit excellent antibacterial activity with a broad antibacterial spectrum, and have the ability to inhibit the activity of β-lactamase, unlike most thienamycin-type compounds, which are liable to be metabolized in a mammalian body. The derivatives of the present invention, in addition, exhibit excellent stability against dehydropeptidase I, which is also known to catalyze the inactivation of compounds of the thienamycin type. Furthermore, the derivatives of the present invention have an excellent urinary recovery. The derivatives of the present invention shown strong antibacterial activity against a wide range of pathogenic bacteria including Gram-positive ones such as *Staphylococcus aureus* and *Bacillus subtilis*, Gram-negative ones such as *Escherichia coli*, Shigella species, *Streptococcus pneumoniae*, Proteus species, Serratia species, Enterobacter species and Pseudomonas species, and anaerobic bacteria such as *Bacteroides fragilis*.

The antibacterial activity was determined by the agar plate dilution method, and the minimal inhibitory concentrations of the compounds of the present invention against a variety of common pathogenic bacteria are shown in the following Table 7. In the Table, the compounds of the invention are identified by reference to the one of the following Examples which illustrates their preparation; in the case of the compound of Example 18, 18A refers to Isomer A, and 18B refers to Isomer B. The microorganisms used are identified as follows:
A: *Staphylococcus aureus* 209P;
B: *Escherichia coli* NIHJ;
C: *Klebsiella pneumoniae* 846;
D: *Pseudomonas aeruginosa* 1001.

TABLE 7

| Compound of Example No. | Microorganism | | | |
|---|---|---|---|---|
| | A | B | C | D |
| 2 | ≦0.01 | ≦0.01 | ≦0.01 | 0.2 |
| 4 | ≦0.01 | ≦0.01 | ≦0.01 | 0.2 |
| 5 | ≦0.01 | ≦0.01 | ≦0.01 | 0.2 |
| 7 | ≦0.01 | ≦0.01 | ≦0.01 | 0.2 |
| 12 | 0.02 | 0.02 | ≦0.01 | 0.2 |
| 14 | ≦0.01 | ≦0.01 | ≦0.01 | 0.4 |
| 16 | ≦0.01 | 0.02 | ≦0.01 | 0.2 |
| 18A | 0.1 | 0.02 | ≦0.01 | 0.1 |
| 18B | 0.1 | 0.02 | 0.02 | 0.2 |
| 20 | ≦0.01 | 0.02 | ≦0.01 | 0.2 |
| imipenem | ≦0.01 | 0.05 | 0.1 | 3.1 |

The results above demonstrate that the compounds of the present invention have activities which are, in general, better than that of imipenem; moreover, they are, unlike imipenem, resistant to dehydropeptidase I and β-lactamase.

The carbapenem-3-carboxylic acid derivatives of the present invention, therefore, are useful as therapeutic agents for the treatment and prophylaxis of infections with these pathogenic bacteria. The compounds may be administered in any conventional form for this purpose, and the exact formulation used will depend on the disease to be treated, the age and condition of the patient and other factors, which are well known in the art. For example, for oral administration, the compounds may be formulated as tablets, capsules, granules, powders or syrups; and for parenteral administration, they may be formulated for intravenous injection or intramuscular injection. The dosage will vary widely, depending upon the age, body weight, symptoms and condition of the patient, as well as the mode of administration and administration times; however, for an adult human patient, a daily dosage of from about 100 mg to 3000 mg is recommended, and this may be administered as a single dose or in divided doses.

The preparation of various of the compounds of the present invention is further illustrated by the following Examples, whilst the preparation of certain of the starting materials used in these Examples is shown in the subsequent Preparations. In these Examples and Preparations, all mesh sizes are in accordance with the Tyler standard. Except where otherwise specified, when the nuclear magnetic resonance spectra were measured in deuterium oxide, tetramethylsilane was used as an external standard; and in other solvents, tetramethylsilane was used as an internal standard.

EXAMPLE 1

(1R,5S,6S)-2-[(2S,4S)-2-(4,4-Dimethyl-1-piperazini-ocarbonyl)pyrrolidin-4-ylthio]-6-[(1R)-1-hydroxyethyl]-1-methyl-1-carbapen-2-em-3-carboxylate fluorosulfonate 1(1)
(2S,4S)-4-Mercapto-2-(4-methyl-1-piperazinylcarbonyl)-1-(4-nitrobenzyloxycarbonyl)pyrrolidine trifluoromethanesulfonate 305 mg of (2S,4S)-4-(4-methoxybenzylthio)-2-(4-methyl-1-piperazinylcarbonyl)-1-(4-nitrobenzyloxycarbonyl)pyrrolidine (prepared as described in Preparation 1) were suspended in 627 μl of anisole, and then the suspension was placed over an ice bath. 3.14 ml of trifluoroacetic acid and 56 μl of trifluoromethanesulfonic acid were then added to the suspension, and the resulting mixture was stirred for 1 hour at room temperature. At the end of this time, the solvent was removed by distillation under reduced pressure. The residue was washed with diethyl ether by repeated decantation, after which it was dried under reduced pressure to obtain 318 mg of the title compound.

Infrared Absorption Spectrum (KBr), $\nu_{max}$ cm$^{-1}$: 1786, 1706, 1666, 1608, 1524, 1441, 1408, 1348, 1279, 1247, 1224, 1165.

Nuclear Magnetic Resonance Spectrum (D$_2$O, 270 MHz), δ ppm: 1.58–1.67 (1H, multiplet); 2.58–3.46 (12H, multiplet); 3.83–4.12 (2H, multiplet); 4.22–4.39 (1H, multiplet); 4.57–4.80 (1H, multiplet); 4.88–5.13 (2H, multiplet); 7.31–7.43 (2H, multiplet); 8.05–8.12 (2H, multiplet).

1(2) 4-Nitrobenzyl (1R, 5S, 6S)-6-[(1R)-1-hydroxyethyl]-1-methyl-2-[(2S, 4S)-2-(4-methyl-1-piperazinylcarbonyl)-1-(4-nitrobenzyloxycarbonyl)pyrrolidin-4-ylthio]-1-carbapen-2-em-3-carboxylate 169 mg of 4-nitrobenzyl (1R, 5R, 6S)-6-[(1R)-hydroxyethyl]-1-methyl-2-oxo-1-carbapenam-3-carboxylate were dissolved in 2.2 ml of anhydrous acetonitrile, and the solution was placed over an ice bath, where 102 μl of diphenylphosphoryl chloride and 87 μl of diisopropylethylamine were added dropwise to it. It was then stirred for 1 hour at this ice-cooled temperature. Whilst still maintaining the mixture over an ice bath, 196 μl of diisopropylethylamine and 1.8 ml of an anhydrous acetonitrile solution containing 312 mg of (2S, 4S)-4-mercapto-2-(4-methyl-1-piperazinylcarbonyl)-1-(4-nitrobenzyloxycarbonyl)pyrrolidine trifluoromethanesulfonate [prepared as described in step (1) above] were added dropwise to the reaction mixture. The mixture was then stirred for 5 hours at this ice-cooled temperature. At the end of this time, the reaction mixture was allowed to stand in a refrigerator overnight, after which the solvent was removed by distillation under reduced pressure. An aqueous solution of sodium hydrogencarbonate was then added to the residue, which was then extracted with ethyl acetate, and dried over anhydrous magnesium sulfate. The solvent was then removed by distillation under reduced pressure, and the residue was purified by column chromatography through silica gel, using a 5:1 by volume mixture of ethyl acetate and methanol as the eluent, to afford 247 mg of the title compound.

Infrared Absorption Spectrum (KBr), $\nu_{max}$ cm$^{-1}$: 1773, 1711, 1654, 1606, 1521, 1345.

Ultraviolet Absorption Spectrum (methanol), $\lambda_{max}$ nm: 267, 318.

Nuclear Magnetic Resonance Spectrum (hexadeuterated dimethyl sulfoxide, 270 MHz), δ ppm: 1.15 (3H, doublet, J=6.35 Hz); 1.16 (3H, doublet, J=7.32 Hz); 1.57-1.66 (1H, multiplet); 2.05-2.38 (5H, multiplet); 2.12-2.20 (3H, two singlets); 2.18-2.89 (1H, multiplet); 3.11-3.63 (7H, multiplet); 3.79-4.28 (4H, multiplet); 4.76, 4.85 (together 1H, two triplets, J=.81 Hz); 5.05-5.48 (4H, multiplet); 7.55, 7.65 (together 2H, two doublets, J=8.79 Hz); 7.72 (2H, doublet, J=8.79 Hz); 8.22, 8.23 (together 4H, two doublets, J=8.79 Hz). 1(3) (1R, 5S, 6S)-2-[(2S, 4S)-2-(4,4-Dimethyl-1-piperaziniocarbonyl)pyrrolidin-4-ylthio]-6-[(1R)-1-hydroxyethyl]-1-methyl-1-carbapen-2-em-3-carboxylate fluorosulfonate 1.36 g of 4-nitrobenzyl (1R, 5S, 6S)-6-[(1R)-1-hydroxyethyl]-1-methyl-2-[(2S, 4S)-2-(4-methyl-1-piperazinylcarbonyl)-1-(4-nitrobenzyloxycarbonyl)pyrrolidin-4-ylthio]-1-carbapen-2-em-3-carboxylate [prepared as described in step (2) above] was dissolved in 13 ml of anhydrous methylene chloride. 282 μl of methyl fluorosulfonate were added to the resulting solution, which was then stirred for 1 hour at room temperature. At the end of this time, the solvent was removed by distillation under reduced pressure, and the powdery product obtained as the residue was dissolved in 60 ml of a 1:1 by volume mixture of tetrahydrofuran and water. Hydrogen gas at room temperature was then passed through the mixture for 3 hours in the presence of 1.2 g of a 10% w/w palladium-on-carbon catalyst. At the end of this time, the catalyst was filtered off. The filtrate was extracted with 100 ml of diethyl ether. The aqueous layer was collected and condensed by evaporation under reduced pressure to 20 ml. This was then lyophilized, to give 920 mg of the crude product as a powder.

70 mg of this crude product were subjected to Lobar column chromatography (Merck, LiChroprep RP-8, Size A), eluted with 5% v/v aqueous methanol. The fractions containing the target compound were collected, condensed by evaporation under reduced pressure, and lyophilized to obtain 45 mg of the title compound as a colorless powder.

Infrared Absorption Spectrum (KBr), $\nu_{max}$ cm$^{-1}$: 1758, 1660, 1603, 1469, 1377, 1273.

Ultraviolet Absorption Spectrum (H$_2$O), $\lambda_{max}$ nm (ε): 298 (9204).

Nuclear Magnetic Resonance Spectrum (D$_2$O, 270 MHz), δ ppm: 1.02 (3H, doublet, J=7.3 Hz); 1.09 (3H, doublet, J=6.3 Hz); 1.73-1.83 (1H, multiplet); 2.78-2.90 (1H, multiplet); 3.08 (3H, singlet); 3.09 (3H, singlet); 3.14-3.29 (3H, multiplet); 3.37-3.42 (4H, multiplet); 3.53 (1H, doublet of doublets, J=12.2 & 6.3 Hz); 3.71-3.91 (5H, multiplet); 4.01-4.08 (2H, multiplet); 4.60 (1H, doublet of doublets, J=7.3 & 9.3 Hz).

EXAMPLE 2

(1R, 5S, 6S)-2-[(2S, 4S)-2-(4,4-Dimethyl-1-piperaziniocarbonyl)pyrrolidin-4-ylthio]-6-[(1R)-1-hydroxyethyl]-1-methyl-1-carbapen-2-em-3-carboxylate 224 mg of 4-nitrobenzyl (1R, 5S, 6S)-6-[(1R)-1-hydroxyethyl]-1-methyl-2-[(2S, 4S)-2-(4-methyl-1-piperazinylcarbonyl)-1-(4-nitrobenzyloxycarbonyl)-pyrrolidin-4-ylthio]-1-carbapen-2-em-3-carboxylate [prepared as described in Example 1(2)] were dissolved in 4.5 ml of methylene chloride, and the mixture was placed on an ice bath. 28 μl of methyl fluorosulfonate were added to the solution, which was the stirred for 1 hour at room temperature. AT the end of this time, the solvent was removed by distillation under reduced pressure. The crude product thus obtained was dissolved in a mixture of 10 ml of tetrahydrofuran and 10 ml of water, and then hydrogen gas was passed for 2 hours at room temperature through the solution, in the presence of 200 mg of a 10% w/w palladium-on-carbon catalyst. The catalyst was then removed by filtration, and then the filtrate was extracted with diethyl ether. The aqueous layer was condensed by evaporation under reduced pressure, and the resulting residue was subjected to Lobar column chromatography (Merck, LiChroprep RP-8), eluted with 20% v/v aqueous methanol. Those fractions containing the title compound were collected, condensed and lyophilized to obtain 28 mg of the title compound.

Infrared Absorption Spectrum (KBr), $\nu_{max}$ cm$^{-1}$: 1753, 1648, 1597, 1467, 1378, 1261.

Ultraviolet Absorption Spectrum (H$_2$O), $\lambda_{max}$ nm (ε): 300 (8817).

Nuclear Magnetic Resonance Spectrum (D$_2$O, 270 MHz), δ ppm: 1.02 (3H, doublet, J=7.32 Hz); 1.10 (3H, doublet, J=6.34 Hz); 1.39-1.50 (1H, multiplet); 2.47-2.59 (1H, multiplet); 2.82-3.00 (2H, multiplet); 3.07 (6H, singlet); 3.17-3.24 (2H, multiplet); 3.32-3.44 (4H, multiplet); 3.56-3.65 (1H, multiplet); 3.66-3.88 (4H, multiplet); 3.89-4.07 (3H, multiplet).

EXAMPLE 3

(1R, 5S, 6S)-2-[(2S, 4S)-2-(4,4-Dimethyl-1-piperaziniocarbonyl)pyrrolidin-4-ylthio]-6-[(1R)-1-hydroxyethyl]-1-methyl-1-carbapen-2-em-3-carboxylate 22 mg of (1R, 5S, 6S)-2-[(2S, 4S)-2-(4,4-dimethyl-1-piperaziniocarbonyl)pyrrolidin-4-ylthio]-6-[(1R)-1-hydroxyethyl]-1-methyl-1-carbapen-2-em-3-carboxylate fluorosulfonate [prepared as described in Example 1(3)] were dissolved in 1 ml of water. The resulting solution was subjected to ion-exchange chromatography through 3 ml of a basic ion-exchange resin [Amberlite IRA-68, (CH$_3$)$_3$ N-type, a product of Organo Co.].

The resin was eluted with water, and those fractions containing the title compound were collected and lyophilized to obtain 18 mg of the title compound. The infrared, ultraviolet and nuclear magnetic resonance spectra of the resulting compound were in full agreement with those of the product of Example 2.

EXAMPLE 4

(1R, 5S, 6S)-2-[(2S, 4S)-2-(4,4-Dimethyl-1-piperaziniocarbonyl)pyrrolidin-4-ylthio]-6-[(1R)-1-hydroxyethyl]-1-methyl-1-carbapen-2-em-3-carboxylate hydrochloride 98 mg of the crude product obtained as described in Example 1(3) were subjected to ion-exchange chromatography through 100 ml of an ion-exchange resin (Dowes 1-x4, 50–100 mesh, Cl$^-$ type) and eluted with water. Those fractions containing the title compound were collected and lyophilized. The powder thus obtained was subjected to Lobar column chromatography (RP-8, Size A), eluted with 5% v/v aqueous methanol. Those fractions containing the title compound were collected, condensed and lyophilized to give 50 mg of the title compound as a colorless powder.

Infrared Absorption Spectrum (KBr), $\nu_{max}$ cm$^{-1}$: 1757, 1660, 1061, 1470, 1375, 1263.

Ultraviolet Absorption Spectrum (H$_2$O), $\lambda_{max}$ nm ($\epsilon$): 297 (8386).

Nuclear Magnetic Resonance Spectrum (D$_2$O, 270 MHz), $\delta$ ppm: 1.02 (3H, doublet, J=7.3 Hz); 1.09 (3H, doublet, J=6.3 Hz); 1.77–1.87 (1H, multiplet); 2.81–2.93 (1H, multiplet); 3.08 (3H, singlet); 3.09 (3H, singlet); 3.13–3.23 (1H, multiplet); 3.26–3.43 (6H, multiplet); 3.59 (1H, doublet of doublets, J=12.2 & 6.5 Hz); 3.71–3.92 (5H, multiplet); 4.01–4.10 (2H, multiplet); 4.68 (1H, doublet of doublets, J=9.3 & 7.8 Hz).

EXAMPLE 5

(1R, 5S, 6S)-2-[(2S, 4S)-2-(4,4-Dimethyl-1-piperaziniocarbonyl)pyrrolidin-4-ylthio]-6-[(1R)-1-hydroxyethyl]-1-methyl-1-carbapen-2-em-3-carboxylate hemisulate 600 mg of the crude product obtained as described in Example 1(3) were subjected to ion-exchange chromatography through 300 ml of an ion-exchange resin (Dowex 1-x4, 50–100 mesh, SO$_4{}^{2-}$ type) and eluted with water. Those fractions containing the title compound were collected and lyophilized. The powder thus obtained was subjected to Lobar column chromatography (RP-8, Size B), eluted with 5% v/v aqueous methanol. The fractions containing the title compound were collected, condensed by evaporation under reduced pressure and lyophilized, to give 354 mg of the title compound as a colorless powder.

Infrared Absorption spectrum (KBr), $\nu_{max}$ cm$^{-1}$: 1757, 1658, 1602, 1469, 1376, 1263.

Nuclear Magnetic Resonance spectrum (D$_2$O, 270 MHz), $\delta$ ppm: 1.02 (3H, doublet, J=7.3 Hz); 1.09 (3H, doublet, J=6.3 Hz); 1.77–1.87 (1H, multiplet); 2.82–2.94 (1H, multiplet); 3.091 (3H, singlet); 3.094 (3H, singlet); 3.12–3.23 (1H, multiplet); 3.20–3.43 (6H, multiplet); 3.59 (1H, doublet of doublets, J=12.2 & 6.4 Hz); 3.71–3.79 (3H, multiplet); 3.83–3.93 (2H, multiplet); 4.02–4.12 (2H, multiplet); 4.70 (1H, doublet of doublets, J=9.3 & 7.8 Hz).

EXAMPLE 6

(1R, 5S, 6S)-2-[(2S, 4S)-2-(1,1-Dimethyl-2-pyrrolidinioethylcarbamoyl)pyrrolidin-4-ylthio]-6-[(1R)-1-hydroxyethyl]-1-methyl-1-carbapen-2-em-3-carboxylate fluorosulfonate 6(1) (2S, 4S)-4-Mercapto-2-(1-methyl-2-pyrrolidinylethylcarbamoyl)-1-(4-nitrobenzyloxycarbonyl)pyrrolidine bis(trifluoromethanesulfonate)

369 mg of (2S, 4S)-4-(4-methoxybenzylthio)-2-(1-methyl-2-pyrrolidinylethylcarbamoyl)-1-(4-nitrobenzyloxycarbonyl)pyrrolidine (prepared as described in Preparation 2) were suspended in 720 $\mu$l of anisole, and the suspension was placed on an ice bath. Maintaining the suspension on the ice bath, 3.6 ml of trifluoroacetic acid and 128 $\mu$l of trifluoromethanesulfonic acid were added to it, and it was then stirred for 1 hour at room temperature. At the end of this time, the solvent was removed by distillation under reduced pressure. The residue was washed with diethyl ether by repeated decantation and dried under reduced pressure, to give 440 mg of the title compound.

Infrared Absorption Spectrum (KBr), $\nu_{max}$ cm$^{-1}$: 1706, 1524, 1431, 1403, 1347, 1285, 1250, 1227, 1168.

Nuclear Magnetic Resonance Spectrum (D$_2$O, 270 MHz), $\delta$ ppm: 1.38–2.25 (7H, multiplet); 2.55–3.47 (11H, multiplet); 3.80–3.97 (1H, multiplet); 4.11–4.26 (1H, two triplets, J=7.81 Hz); 4.97–5.14 (2H, multiplet); 7.37, 7.43 (together 2H, two doublets, J=8.30 Hz); 8.09 (2H, doublet, J=8.30 Hz).

6(2) 4-Nitrobenzyl (1R, 5S, 6S)-6-[(1R)-1-hydroxyethyl]-1-methyl-1-[(2S, 4S)-2-(1methyl-2pyrrolidinylcarbamoyl)-1-(4-nitrobenzyloxycarbonyl)pyrrolidin-4-ylthio]-1-carbapen-2-em-3-carboxylate 180 mg of 4-nitrobenzyl (1R, 5R, 6S)-6-[(1R)-1-hydroxyethyl]-1-methyl-2-oxo-1-carbapenam-3-carboxylate were dissolved in 2.3 ml of anhydrous acetonitrile, and the solution was placed on an ice bath. Maintaining the solution on the ice bath, 109 $\mu$l of diphenylphosphoryl chloride and 92 $\mu$l of diisopropylethylamine were added dropwise to the solution. The resulting mixture was then stirred for 1 hour at this ice-cooled temperature, after which, whilst still maintaining the reaction mixture on the ice bath, 313 $\mu$of diisopropylethylamine and 1.9 ml of an anhydrous acetonitrile solution containing 440 mg of (2S, 4S)-4-mercapto-2-(1-methyl-2-pyrrolidinylethylcarbamoyl)-1-(4-nitrobenzyloxycarbonyl)pyrrolidine bis(trifluoromethanesulfonate) [prepared as described in step (1) above] were added dropwise to the mixture. The mixture was then stirred at this ice-cooled temperature for 5 hours and allowed to stand for 2 days in a refrigerator. At the end of this time, the solvent was removed by distillation under reduced pressure. An aqueous solution of sodium hydrogencarbonate was added to the residue, which was then extracted with ethyl acetate. The organic layer was dried over anhydrous magnesium sulfate. The solvent was removed by distillation under reduced pressure, and the resulting residue was subjected to Lobar column chromatography (Merck, LiChroprep Si60). From fractions eluted with a 1:2 by volume mixture of acetonitrile and methanol were obtained 65 mg of the title compound.

Infrared Absorption Spectrum (KBr), $\nu_{max}$ cm$^{-1}$: 1773, 1712, 1600.

Ultraviolet Absorption Spectrum (methanol), $\lambda_{max}$ nm: 319, 268.

Nuclear Magnetic Resonance Spectrum (CDC$_3$, 270 MHz), δ ppm: 1.10, 1.27 (together 3H, two doublets, J=7.32 Hz); 1.21, 1.37 (together 3H, two doublets, J=6.35 Hz); 1.42–4.39 (26H, multiplet); 5.15–5.62 (4H, multiplet); 7.50–7.67 (4H, multiplet); 8.23 (1H, two doublets, J=8.79 Hz).

6(3) (1R, 5S, 6S)-2-[(2S, 4S)-2-(1,1-Dimethyl-2-pyrrolidinioethylcarbamoyl)pyrrolidin-4-ylthio]-6-[(1R)-1-hydroxyethyl]-1-methyl-1-carbapen-2-em-3-carboxylate fluorosulfonate 62 mg of 4-nitrobenzyl (1R, 5S, 6S)-6-[(1R)-1-hydroxyethyl]-1-methyl-2-[(2S, 4S)-2-(1-methyl-2-pyrrolidinylcarbamoyl)-1-(4-nitrobenzyloxycarbonyl)pyrrolidin-4-ylthio]-1-carbapen-2-em-3-carboxylate [prepared as described in Example 6(2)] were dissolved in 1.2 ml of methylene chloride, and the solution was placed on an ice bath. Maintaining the solution on the ice bath, 7.5 μl of methyl fluorosulfonate were added, and the resulting mixture was stirred for 1 hour at room temperature. At the end of this time, the solvent was removed by distillation under reduced pressure, and the resulting crude product was dissolved in a mixture of 3 ml of tetrahydrofuran and 3 ml of water. Gaseous hydrogen was then passed through the solution for 1.5 hours at room temperature, in the presence of 100 mg of a 10% w/w palladium-on-carbon catalyst. The catalyst was removed by filtration, and then the filtrate was extracted with diethyl ether. The aqueous layer was condensed by evaporation under reduced pressure, and the residue was subjected to column chromatography through Sephadex (trade mark) G-10 (a product of Pharmacia, 40–120 μm), eluted with water. Those fractions containing the title compound were collected and lyophilized to obtain 21 mg of the title compound.

Infrared Absorption Spectrum (KBr), $\nu_{max}$ cm$^{-1}$: 1740, 1672, 1600, 1312, 1273.

Ultraviolet Absorption Spectrum (H$_2$O), $\lambda_{max}$ nm: 296.

Nuclear Magnetic Resonance Spectrum (D$_2$O, 270 MHz), δ ppm: 1.20 (3H, doublet, 7.32 Hz); 1.10 (3H, doublet, J=6.34 Hz); 1.57–2.37 (6H, multiplet); 2.69 (3H, singlet); 2.96 (3H, singlet); 2.57–4.28 (15H, multiplet).

EXAMPLE 7

(1R, 5S, 6S)-2-[(2S, 4S)-2-(4,4-Dimethyl-1-homopiperaziniocarbonyl)pyrrolidin-4-ylthio]-6-[(1R)-1-hydroxyethyl]-1-methyl-1-carbapen-2-em-3-carboxylate fluorosulfonate

7(1) (2S, 4S)-4-Mercapto-2-(4-methyl-1-homopiperazinylcarbonyl)-1-(4-nitrobenzyloxycarbonyl)pyrrolidine bis(trifluromethanesulfonate)

620 mg of (2S, 4S)-4-(4-methoxybenzylthio)-2-(4-methyl-1-homopiperazinylcarbonyl)-1-(4-nitrobenzyloxycarbonyl)pyrrolidine (prepared as described in Preparation 5) were suspended in 1.23 ml of anisole, and the suspension was placed on an ice bath. Whilst the suspension was still on the ice bath, 6.2 ml of trifluoroacetic acid and 200 μl of trifluoromethanesulfonic acid were added to it, and the resulting mixture was stirred for 1 hour at room temperature. At the end of this time, the mixture was treated in a similar manner to that described in Example 1(1), to give 640 mg of the title compound.

Infrared Absorption Spectrum (liquid film), $\nu_{max}$ cm$^{-1}$: 1701, 1608, 1524, 1347, 1286, 1246, 1228, 1173, 1029.

Nuclear Magnetic Resonance Spectrum (hexadeuterated dimethyl sulfoxide, 270 MHz), δ ppm: 1.66–1.78 (1H, multiplet); 1.96–2.13 (2H, multiplet); 2.67–2.86 (5H, multiplet); 2.99–4.07 (12H, multiplet); 4.64–4.83 (1H, multiplet); 5.02–5.26 (2H, multiplet); 7.49–7.65 (2H, multiplet); 8.23 (2H, doublet).

7(2) 4-Nitrobenzyl (1R, 5S, 6S)-6-[(1R)-1-hydroxyethyl]-1-methyl-2-[(2S, 4S)-2-(4-methyl-1-homopiperazinylcarbonyl)-1-(4-nitrobenzyloxycarbonyl)pyrrolidin-4-ylthio]-1-carbapen-2-em-3-carboxylate 340 mg of 4-nitrobenzyl (1R, 5R, 6S)-6[(1R)-1-hydroxyethyl]-1-methyl-2-oxo-1-carbapenam-3-carboxylate were dissolved in 3.5 ml of anhydrous acetonitrile, and the solution was placed on an ice bath. Whilst the solution was still on the ice bath, 210 μl of diphenylphosphoryl chloride and 180 μl of diisopropylethylamine were added dropwise to it, and the resulting mixture was stirred for 1 hour at this ice-cooled temperature. 580 μl of diisopropylethylamine and 5 ml of an anhydrous acetonitrile solution containing 640 mg of (2S, 4S)-4-mercapto-2-(4-methyl-1-homopiperazinylcarbonyl)-1-(4-nitrobenzyloxycarbonyl)pyrrolidine bis(trifluoromethanesulfonate) [prepared as described in step (1) above] were then added dropwise to the reaction mixture, still on an ice bath, and the resulting mixture was stirred overnight at this ice-cooled temperature. At the end of this time, the mixture was treated and purified by means similar to those described in Example 1(2), to give 316 mg of the title compound.

Infrared Absorption Spectrum (KBr), $\nu_{max}$ cm$^{-1}$: 1773, 1710, 1648, 1606, 1521.

Ultraviolet Absorption Spectrum (methanol). $\lambda_{max}$ nm: 277, 318.

Nuclear Magnetic Resonance Spectrum (CDCl$_3$, 270 MHz), δ ppm: 1.29 (3H, doublet, J=7.32 Hz); 1.37 (3H, doublet, J=5.86 Hz); 1.48–2.17 (4H, multiplet); 2.29 (1H, singlet); 2.43, 2.45 (together 3H, two singlets); 2.58–2.97 (4H, multiplet); 3.25–3.86 (9H, multiplet); 4.01–4.28 (2H, multiplet); 4.68–4.76 (1H, multiplet); 5.06–5.52 (2H, multiplet); 7.46 (1H, doublet, J=8.30 Hz); 7.51 (1H, doublet, J=8.79 Hz); 7.65 (2H, doublet, J=8.30 Hz); 8.23 (4H, two doublets, J=8.79 & 8.30 Hz).

7(3) (1R, 5S, 6S)-2-[(2S, 4S)-2-(4,4-Dimethyl-1-homopiperaziniocarbonyl)pyrrolidin-4-ylthio]-6-[(1R)-1-hydroxyethyl]-1-methyl-1-carbapen-2-em-3-carboxylate fluorosulfonate 290 mg of 4-nitrobenzyl (1R, 5S, 6S)-6-[(1R)-1-hydroxyethyl]-1-methyl-2-[(2S, 4S)-2-(4-methyl-1-homopiperazinylcarbonyl)-1-(4-nitrobenzyloxycarbonyl)pyrrolidin-4-ylthio]-1-carbapen-2-em-3-carboxylate [prepared as described in step (2) above] were dissolved in 6 ml of methylene chloride, and the solution was placed on an ice bath. Whilst the solution was still on the ice bath, 60 μl of methyl fluorosulfonate were added, and the resulting mixture was stirred for 30 minutes at this ice-cooled temperature and then for 1 hour at room temperature. At the end of this time, the solvent was removed by distillation under reduced pressure, and the resulting crude product was subjected to hydrogenation, treated, purified and lyophilized using similar procedures to those described in Example 1(3) to obtain 110 mg of the title compound.

Infrared Absorption Spectrum (KBr), $\nu_{max}$ cm$^{-1}$: 1760, 1653, 1603, 1467, 1379, 1279.

Ultraviolet Absorption Spectrum (H$_2$O), $\lambda_{max}$ nm: 297 (8340).

Nuclear Magnetic Resonance Spectrum (D$_2$O, 270 MHz), δ ppm: 1.02 (3H, doublet, J=7.33 Hz); 1.10 (3H, doublet, J=5.86 Hz); 1.80–1.86 (1H, multiplet); 2.14 (2H, broad singlet); 2.76–3.05 (1H, multiplet); 3.02, 303 (together 6H, two singlets); 3.14–3.33 (3H, multiplet); 3.41–3.90 (10H, multiplet); 4.03–4.08 (2H, multiplet); 4.63–4.70 (1H, multiplet).

EXAMPLE 8

(1R, 5S, 6S)-6-[(1R)-1-Hydroxyethyl]-1-methyl-2-[(2S, 4S)-2-(1-methyl-4-pyridiniomethylcarbamoyl)pyrrolidin-4-ylthio]-1-carbapen-2-em-3-carboxylate 8(1) (2S, 4S)-4-Mercapto-2-(1-methyl-4-pyridiniomethylcarbamoyl)-1-(4-nitrobenzyloxycarbonyl)pyrrolidine trifluoromethanesulfonate 395 mg of (2S, 4S)-4-(4-methoxybenzylthio)-2-(1-methyl-4-pyridiniomethylcarbamoyl)-1-(4-nitrobenzyloxycarbonyl)pyrrolidine fluorosulfonate (prepared as described in Preparation 8) were suspended in 660 μl of anisole, and the suspension was placed on an ice bath. Whilst the suspension was still on the ice bath, 3.3 ml of trifluoroacetic acid and 59 μl of trifluoromethanesulfonic acid were added to the suspension, and the resulting mixture was stirred for 1 hour at room temperature. At the end of this time, the solvent was removed by distillation under reduced pressure, and the residue was washed with diethyl ether by repeated decantation and dried under reduced pressure to obtain 352 mg of the title compound, as an oily substance.

Infrared Absorption Spectrum (liquid film), $\nu_{max}$ cm$^{-1}$: 1784, 1700, 1647, 1607, 1581, 1522, 1346, 1294, 1243, 1226, 1171.

8(2) 4-Nitrobenzyl (1R, 5S, 6S)-6-[(1R)-1-hydroxyethyl]-1-methyl-2-[(2S, 4S)-2-(1-methyl-4-pyridiniomethylcarbamoyl)-1-(4-nitrobenzyloxycarbonyl)pyrrolidin-4-ylthio]-1-carbapen-2-em-3-carboxylate trifluoromethanesulfonate 183 mg of 4-nitrobenzyl (1R, 5R, 6S)-6-[(1R)-1-hydrozyethyl]-1-methyl-2-oxo-1-carbapenam-3-carboxylate were dissolved in 2.5 ml of anhydrous acetonitrile, and the solution was placed on an ice bath. Whilst the solution was still on the ice bath, 110 μl of diphenylphosphoryl chloride and 94 μl of diisopropylethylamine were added, and the resulting mixture was stirred for 1 hour at this ice-cooled temperature. 145 μl of diisopropylethylamine and 1.5 ml of an anhydrous acetonitrile solution containing 352 mg of (2S, 4S)-4-mercapto-2-(1-methyl-4-pyridiniomethylcarbamoyl)-1-(4-nitrobenzyloxy carbonyl)pyrrolidine trifluoromethanesulfonate [prepared as described in step (1) above] were then added to the reaction mixture, still on an ice bath, and the resulting mixture was stirred for 1 hour at room temperature. The reaction mixture was then allowed to stand in a refrigerator for 5 days. At the end of this time, the solvent was removed by distillation under reduced pressure, and the resulting residue was subjected to Lobar column chromatography (Merck, LiChroprep Si60). Those fractions eluted with a 10:1 by volume mixture of acetonitrile and water gave 98 mg of the title compound.

Nuclear Magnetic Resonance Spectrum (hexadeuterated dimethyl sulfoxide, 270 MHz), δ ppm: 1.24, 1.27 (together 3H, two doublets, J=7.32 Hz); 1.26, 1.37 (together 3H, two doublets, J=6.35 Hz); 1.75–2.07 (1H, multiplet); 2.68–2.74 (1H, multiplet); 3.07–3.78 (5H, multiplet); 3.90–4.45 (3H, multiplet); 4.25–4.28 (together 3H, two singlets); 4.53 (2H, singlet); 5.20–5.32 (2H, multiplet); 6.91–7.23 (3H, multiplet); 7.56–7.96 (4H, multiplet); 8.19–8.25 (2H, multiplet); 8.78–8.96 (3H, multiplet).

8(3) (1R, 5S, 6S)-6-[(1R)-1-Hydroxyethyl]-1-methyl-2-[(2S, 4S)-2-(1-Methyl-4-pyridiniomethylcarbamoyl)pyrrolidin-4-ylthio]-1-carbapen-2-em-3-carboxylate 97 mg of 4-nitrobenzyl (1R, 5S, 6S)-6-[(1R)-1-hydroxyethyl]-1-methyl-2-[(2S, 4S)-2-(1-methyl-4-pyridiniomethylcarbamoyl)-1-(4-nitrobenzyloxycarbonyl)pyrrolidin-4-ylthio]-1-carbapen-2-em-3-carboxylate trifluormethanesulfonate [prepared as described in step (2) above] were dissolved in a mixture of 5 ml of tetrahydrofuran and 5 ml of a 0.1M phosphate buffer (pH 7.0). Hydrogen was passed through the solution at room temperature for 2 hours in the presence of 100 mg of a 10% w/w palladium-on-carbon catalyst. The resulting mixture was then subjected to similar treatment and purification to those described in Example 2(1), to give 10 mg of the title compound.

Ultraviolet Absorption Spectrum (H$_2$O), $\lambda_{max}$ nm: 298, 258.

Nuclear Magnetic Resonance Spectrum (D$_2$O, 270 MHz), δ ppm: 1.01 (3H, doublet, J=7.33 Hz); 1.10 (3H, doublet, J=6.23 Hz); 1.60–2.12 (2H, multiplet); 2.44–4.26 (10H, multiplet); 4.16 (3H, singlet); 7.73 (2H, doublet, J=6.42 Hz); 8.51 (2H, doublet, J=6.42 Hz).

EXAMPLE 9

(1R, 5S, 6S)-6-[(1R)-1-Hydroxyethyl]-1-methyl-2-[(2S, 4S)-2-(2-trimethylammonioethylcarbamoyl)pyrrolidin-4-ylthio]-1-carbapen-2-em-3-carboxylate fluorosulfonate 9(1) (2S, 4S)-2-(2-Dimethylaminoethylcabamoyl)-4-mercapto-1-(4-nitrobenzyloxycarbonyyl)pyrrolidine trifluormethanesulfonate 335 mg of (2S, 4S)-2-(2-dimethylaminoethylcarbamoyl)-4-(4-methoxybenzylthio)-1-(4-nitrobenzyloxycarbonyl)pyrrolidine (prepared as described in Preparation 4) were dissolved in 1 ml of anisole, and the solution was placed on an ice bath. Whilst the solution was still on the ice bath, 4 ml of trifluoroacetic acid and 120 μl of trifluoromethanesulfonic acid were added to it. The resulting mixture was then stirred for 2 hours at room temperature. At the end of this time, the solvent was removed by distillation under reduced pressure, and the residue was washed with diethyl ether and dried under reduced pressure to give 530 mg of the title compound.

Infrared Absorption Spectrum (KBr), $\nu_{max}$ cm$^{-1}$: 1702, 1524, 1347, 1289, 1227, 1172, 1029, 638, Nuclear Magnetic Resonance Spectrum (hexadeuterated dimethyl sulfoxide+D$_2$O, 270 MHz), δ ppm: 1.72–1.86 (1H, multiplet); 2.56–2.72 (1H, multiplet); 2.76 (3H, singlet); 2.80 (3H, singlet); 3.02–3.27 (3H, multiplet); 3.34–3.44 (3H, multiplet); 3.90–4.04

(1H, multiplet); 4.14, 4.26 (together 1H, two triplets, J=7.8 Hz); 5.09-5.28 (2H, multiplet); 7.55, 7.63 (together 2H, two doublets, J=8.8 Hz); 8.24 (2H, doublet, J=8.8 Hz).

9(2) 4-Nitrobenzyl (1R, 5S, 6S)-6-[(1R)-1-hydroxyethyl]-1-methyl-2-[(2S, 4S)-2-(2-trimethylammonioethylcarbamoyl)-1-(4-nitrobenzyloxycarbonyl)pyrrolidin-4-ylthio]-1-carbapen-2-em-3-carboxylate 220 mg of 4-nitrobenzyl (1R, 5R, 6S)-6-[(1R)-1-hydroxyethyl]-1-methyl-2-oxo-1-carbapenam-3-carboxylate were dissolved in 5 ml of anhydrous acetonitrile, and the solution was placed on an ice bath. Whilst the solution was still on the ice bath, 130 μl of diphenylphosphoryl chloride and 110 μl of diisopropylethylamine were added dropwise, and the resulting mixture was stirred for 30 minutes at this ice-cooled temperature. At the end of this time, 250 μl of diisopropylethylamine and 5 ml of an anhydrous acetonitrile solution containing 530 mg of (2S, 4S)-2-(2-dimethylaminoethylcarbamoyl)-4-mercapto-1-(4-nitrobenzyloxycarbonyl)pyrrolidine trifluoromethanesulfonate [prepared as described in step (1) above] were added dropwise to the reaction mixture, still on an ice bath, and the resulting mixture was stirred for 2 hours at this ice-cooled temperature. The reaction mixture was then allowed to stand overnight in a refrigerator (at 4° C.). At the end of this time, the solvent was removed by distillation under reduced pressure, and the residue was subjected to silica gel Lobar column chromatography (Merck, LiChroprep Si60). Elution using a 7:2:1 by volume mixture of ethyl acetate, ethanol and water afford 310 mg of the title compound, as a powder.

Infrared Absorption Spectrum (KBr), $v_{max}$ cm$^{-1}$: 1772, 1707, 1522, 1346, 1280, 1030, 638.

Nuclear Magnetic Resonance Spectrum (CDCl$_3$, 270 MHz), δ ppm: 1.28 (3H, doublet, J=7.3 Hz); 1.37 (3H, doublet, J=6.4 Hz); 1.82-2.26 (1H, multiplet); 2.63-2.73 (1H, multiplet); 2.88, 2.90 (together 3H, two singlets); 2.96, 2.98 (together 3H, two singlets); 3.26-4.08 (10H, multiplet); 4.23-4.32 (2H, multiplet); 4.43 (1H, t, J=7.3 Hz); 5.15-5.53 (4H, multiplet); 7.53 (2H, doublet, J=8.8 Hz); 7.66 (2H, doublet, J=8.8 Hz); 8.22, 8.23 (together 4H, two doublets, J=8.8 Hz); 8.69 (1H, broad).

9(3) (1R,5S,6S)-6-[(1R)-1-Hydroxyethyl]-1-methyl-2-[(2S, 4S)-2-(2-trimethylammonioethylcarbamoyl)pyrrolidin-4-ylthio]-1-carbapen-2-em-3-carboxylate fluorosulfonate 90 mg of 4-nitrobenzyl (1R,5S,6S)-6-[(1R)-1-hydroxyethyl]-1-methyl-2-[(2S,4S)-2-(2-trimethylammonioethylcarbamoyl)-1-(4-nitrobenzyloxycarbonyl)pyrrolidin-4-ylthio]-1-carbapen-2-em-3-carboxylate [prepared as described in step (2) above] were dissolved in 2 ml of anhydrous methylene chloride, and the solution was placed on an ice bath. Whilst the solution was still on the ice bath, 20 μl of methyl fluorosulfonate were added, and the resulting mixture was stirred for 30 minutes at room temperature. At the end of this time, the solvent was removed by distillation under reduced pressure, and the resulting crude product was dissolved in 5 ml of a 1:1 by volume mixture of tetrahydrofuran and water. Hydrogen was passed through the resulting solution for 2 hours at room temperature in the presence of 90 mg of a 10% w/w palladium-on-carbon catalyst. At the end of this time, the catalyst was removed by filtration. The filtrate was condensed by evaporation under reduced pressure, and 5 ml of water were added to the residue. The soluble fraction was subjected to column chromatography through a Sephadex G-10 (Pharmacia, 40-120 μm) column, eluted with water. Those fractions containing the title compound were collected and lyophilized to give 53 mg of the title compound.

Infrared Absorption Spectrum (KBr), $v_{max}$ cm$^{-1}$: 1757, 1685, 1602, 1565, 1388, 1280.

Ultraviolet Absorption Spectrum (H$_2$O), $\lambda_{max}$ nm: 296.

Nuclear Magnetic Resonance Spectrum (D$_2$O, 270 MHz), δ ppm: 1.01 (3H, doublet, J=7.3 Hz); 1.09 (3H, doublet, J=6.4 Hz); 1.87-1.97 (1H, multiplet); 2.68-2.80 (1H, multiplet); 3.01 (9H, singlet); 3.03-3.72 (11H, multiplet); 3.82-3.90 (1H, multiplet); 4.00-4.11 (2H, multiplet); 4.28-4.34 (1H, multiplet).

EXAMPLE 10

(1R,5S,6S)-6-[(1R)-1-Hydroxyethyl]-1-methyl-2-[(2S,4S)-2-(2-trimethylammonioethylcarbamoyl)pyrrolidin-4-ylthio]-1-carbapen-2-em-3-carboxylate hydrochloride 28 mg of (1R,5S,6S)-6-[(1R)-1-hydroxyethyl]-1-methyl-2-[(2S,4S)-2-(2-trimethylammonioethylcarbamoyl)-pyrrolidin-4-ylthio]-1-carbapen-2-em-3-carboxylate fluorosulfonate [prepared as described in Example 9(3)] were dissolved in 3 ml of water. The solution was then subjected to ion-exchange column chromatography through 10 ml of an ion-exchange resin (Dowex 1-x4, 50-100 mesh, Cl$^-$ type) and eluted with water. Those fractions containing the title compound were collected and lyophilized to obtain 14 mg of the title compound as a powder.

Nuclear Magnetic Resonance Spectrum (D$_2$O, 270 MHz), δ ppm: 1.01 (3H, doublet, J=7.3 Hz); 1.09 (3H, doublet, J=6.4 Hz); 1.85-1.95 (1H, multiplet); 2.65-2.78 (1H, multiplet); 3.01 (9H, singlet); 3.05-3.69 (11H, multiplet); 3.78-3.88 (1H, multiplet); 4.01-4.10 (2H, multiplet); 4.23-4.29 (1H, multiplet).

EXAMPLE 11

(1R,5S,6S)-6-[(1R)-1-Hydroxyethyl]-1-methyl-2-[(4S)-2-[(1-methyl-3-quinuclidinio)carbamoyl]pyrrolidin-4-ylthio]-1-carbapen-2-em-3-carboxylate fluorosulfonate

11(1) (4S)-4-Mercapto-1-(4-nitrobenzyloxycarbonyl)-2-[(3-quinuclidinyl)carbamoyl]pyrrolidine bis(trifluoromethanesulfonate)

770 mg of (4S)-4-(4-methoxybenzylthio)-2-[(3-quinuclidinyl)carbamoyl]-1-(4-nitrobenzyloxycarbonyl)pyrrolidine (prepared as described in Preparation 6) were suspended in 1.5 ml of anisole, and the suspension was placed on an ice bath. Whilst the suspension was still on the ice bath, 6.5 ml of trifluoroacetic acid and 246 μl of trifluoromethanesulfonic acid were added to it, and the resulting mixture was stirred for 1.5 hours at room temperature. At the end of this time, the solvent was removed by distillation under reduced pressure, and the resulting residue was washed with hexane; the produce was then precipitated by the addition of diethyl ether, and the mixture was filtered, to give 813 mg of the title compound.

Nuclear Magnetic Resonance Spectrum (hexadeuterated dimethyl sulfoxide, 270 MHz), δ ppm: 1.37-2.10 (6H, multiplet); 2.54-3.70 (9H, multiplet);

3.79–4.37 (3H, multiplet); 5.08–5.30 (2H, multiplet); 7.50–7.73 (2H, multiplet); 8.17–8.43 (2H, multiplet).

11(2) 4-Nitrobenzyl (1R,5S,6S)-6-[(1R)-1-hydroxyethyl]-1-methyl-2-{(4S)-1-(4-nitrobenzyloxycarbonyl)-2-[(3-quinuclidinyl)carbamoyl]pyrrolidin-4-ylthio}-1-carbapen-2-em-3-carboxylate 388 mg of 4-nitrobenzyl (1R,5R,6S)-6-[(1R)-1-hydroxyethyl]-1-methyl-2-oxo-1-carbapenam-3-carboxylate were dissolved in 4 ml of anhydrous acetonitrile, and the solution was placed on an ice bath. Whilst the solution was still on the ice bath, 302 mg of diphenylphosphoryl chloride and 145 mg of diisopropylethylamine were added dropwise to it, and the resulting mixture was stirred for 30 minutes at this ice-cooled temperature. At the end of this time, 504 mg of diisopropylethylamine and 4 ml of an anhydrous acetonitrile solution containing 813 mg of (4S)-4-mercapto-1-(4-nitrobenzyloxycarbonyl)-2-[(3-quinuclidinyl)carbamoyl]pyrrolidine bis(trifluoromethanesulfonate) [prepared as described in step (1) above], were added to the reaction mixture, still on an ice bath, and the mixture was stirred for 3 hours at this ice-cooled temperature. It was then allowed to stand on an ice bath overnight. At the end of this time, the solvent was removed by distillation under reduced pressure, and an aqueous solution of sodium hydrogencarbonate was added; the mixture was then extracted with ethyl acetate. The extract was dried over anhydrous magnesium sulfate, and then the solvent was removed by distillation under reduced pressure. The residue was subjected to Lobar column chromatography (Merck, LiChroprep RP-8). Elution with 60–80% by volume aqueous methanol gave 160 mg of the title compound.

Nuclear Magnetic Resonance Spectrum (CDCl$_3$, 270 MHz), δ ppm: 1.11, 1.27 (together 3H, two doublets, J=7.0 Hz); 1.21, 1.37 (together 3H, two doublets, J=6.4 Hz); 1.55–2.20 (5H, multiplet); 2.35–3.10 (9H, multiplet); 3.15–4.15 (6H, multiplet); 4.15–4.50 (2H, multiplet); 5.24 (2H, singlet); 5.20–5.51 (2H, multiplet); 7.00 (1H, broad); 7.45–7.67 (4H, multiplet); 8.20–8.30 (4H, multiplet).

11(3) (1R,5S,6S)-6-[(1R)-1-Hydroxyethyl]-1-methyl-2-[(4S)-2-[(1-methyl-3-quinuclidinio)carbamoyl]pyrrolidin-4-ylthio]-1-carbapen-2-em-3-carboxylate fluorosulfonate 160 mg of 4-nitrophenyl (1R,5S,6S)-6-[(1R)-1-hydroxyethyl]-1-methyl-2-{(4S)-1-(4-nitrobenzyloxycarbonyl)-2-[(3-quinuclidinyl)carbamoyl]pyrrolidin-4-ylthio}-1-carbapen-2-em-3-carboxylate [prepared as described in step (2) above] were dissolved in 2 ml of methylene chloride, and the solution was placed on an ice bath. Whilst the solution was still on the ice bath, 46.9 mg of methyl fluorosulfonate were added to the solution, and the resulting mixture was stirred for 3 hours at room temperature. At the end of this time, the solvent was removed by distillation under reduced pressure, and the resulting residue was dissolved in a mixture of 4 ml of tetrahydrofuran and 4 ml of water. Hydrogen was then passed through the solution for 2 hours at room temperature in the presence of a 10% w/w palladium-on-carbon catalyst. The catalyst was then removed by filtration. The filtrate was washed with diethyl ether, subjected to Lobar column chromatography (Merck, LiChroprep RP-8) and eluted with 7% v/v aqueous acetonitrile. Those fractions containing the title compound were collected, condensed by evaporation under reduced pressure and lyophilized to obtain 53 mg of the title compound.

Infrared Absorption Spectrum (KBr), $v_{max}$ cm$^{-1}$: 1759, 1681, 1559, 1470, 1379, 1289, 1070.

Ultraviolet Absorption Spectrum (H$_2$O), λ$_{max}$ nm: 297.

Nuclear Magnetic Resonance Spectrum (D$_2$O, 270 MHz), δ ppm: 1.02 (3H, doublet, J=6.84 Hz); 1.10 (3H, doublet, J=6.34 Hz); 1.75–2.30 (5H, multiplet); 2.82, 2.84 (together 3H, two singlets); 2.65–4.90 (17H, multiplet).

EXAMPLE 12

(1R,5S,6S)-2-[(2S,4S)-2-[4-(2-Hydroxyethyl)-4-methyl-1-piperaziniocarbonyl]pyrrolidin-4-ylthio]-6-[(1R)-1-hydroxyethyl]-1-methyl-1-carbapen-2-em-3-carboxylate fluorosulfonate 12(1) (2S,4S)-2-[4-(2-Hydroxyethyl)piperazinylcarbonyl]-4-mercapto-1-(4-nitrobenzyloxycarbonyl)pyrrolidine bis(trifluoromethanesulfonate)

288 mg of (2S,4S)-2-[4-(2-hydroxyethyl)piperazinylcarbonyl]-4-(4-methoxybenzylthio)-1-(4-nitrobenzyloxycarbonyl)pyrrolidine (prepared as described in Preparation 7) were dissolved in 560 μl of anisole, and the solution was placed on an ice bath. 2.8 ml of trifluoroacetic acid and 91 μl of trifluoromethanesulfonic acid were added to the solution, still on the ice bath, and the resulting mixture was stirred for 1 hour at room temperature. At the end of this time, the solvent was removed by distillation under reduced pressure. The resulting residue was washed with diethyl ether by repeated decantation, and then dried under reduced pressure, to give 380 mg of the title compound.

Infrared Absorption Spectrum (KBr), $v_{max}$ cm$^{-1}$: 1795, 1705, 1666, 1609, 1525, 1442, 1408, 1348, 1281, 1226, 1169.

Nuclear Magnetic Resonance Spectrum (D$_2$O, 270 MHz), δ ppm: 1.54–1.63 (1H, multiplet); 2.61–2.72 (1H, multiplet); 2.90–4.46 (14H, multiplet); 4.64–4.96 (2H, multiplet); 5.08 (2H, singlet); 7.42 (2H, doublet, J=8.79 Hz); 8.08, 8.10 (together 2H, two doublets, J=8.79 Hz).

12(2) 4-Nitrobenzyl (1R,5S,6S)-6[(1R)-1-hydroxyethyl]-2-[(2S,4S)-2-[4-(2-hydroxyethyl)-4-methyl-1-piperazinylcarbonyl]-1-(4-nitrobenzyloxycarbonyl)pyrrolidin-4-ylthio]-1-methyl-1-carbapen-2-em-3-carboxylate 148 mg of 4-nitrobenzyl (1R,5R,6S)-6-[(1R)-1-hydroxyethyl]-1-methyl-2-oxo-1-carbapenam-3-carboxylate were dissolved in 1.9 ml of anhydrous acetonitrile, and the solution was placed on an ice bath. 90 μl of diphenylphosphorylchloride and 76 μl of diisopropylethylamine, were added dropwise to the solution, still on the ice bath, and the resulting mixture was stirred for 1 hour at this ice-cooled temperature. At the end of this time, 257 μl of diisopropylethylamine and 1.6 ml of an anhydrous acetonitrile solution containing 361 mg of (2S,4S)-2-[4-(2-hydroxyethyl)piperazinylcarbonyl]-4-mercapto-1-(4-nitrobenzyloxycarbonyl)pyrrolidine bis(trifluoromethanesulfonate) [prepared as described in step (1) above] were added dropwise to the reaction mixture, still on the ice bath, and the mixture was stirred for 6 hours at this ice-cooled temperature; it was then allowed to stand overnight in a refrigerator. The reaction mixture was then treated in a similar manner to that described in Example 1(2), after which it was subjected to Lobar column chromatography (Merck, Lichroprep Si60). Those fractions eluted with a 5:1 by volume mixture of acetonitrile and methanol yielded 220 mg of the title compound.

Ultraviolet Absorption Spectrum (methanol), $\lambda_{max}$ nm: 268, 315.

Thin layer chromatography: Kieselgel L60F$_{254}$ (Merck); (Developing solvent: a 5:1 by volume mixture of acetonitrile and methanol): Rf=0.33.

Infrared Absorption Spectrum (KBr), $v_{max}$ cm$^{-1}$: 1772, 1710, 1652, 1606, 1521, 1489, 1440, 1405, 1345, 1280, 1207.

Nuclear Magnetic Resonance Spectrum (CDCl$_3$, 270 MHz), δ ppm: 1.27, 1.28 (together 3H, two doublets, J=7.33 Hz); 1.37 (3H, doublet, J=6.35 Hz); 1.82–2.00 (1H, multiplet); 2.33–2.78 (8H, multiplet); 3.25–3.29 (1H, multiplet); 3.32–3.82 (9H, multiplet); 4.00–4.30 (3H, multiplet); 4.69, 4.74 (together 1H, two triplets, J=7.81 Hz); 5.05–5.52 (5H, multiplet); 7.44, 7.51 (together 2H, two doublets, J=8.79 Hz); 7.64 (2H, doublet, J=8.79 Hz); 8.23 (4H, doublet, J=8.79 Hz).

12(3)

(1R,5S,6S)-6-[(1R)-1-Hydroxyethyl]-2-[(2S,4S)-2-[4-(2-hydroxyethyl)-4-methyl-1-piperaziniocarbonyl]pyrrolidin-4-ylthio]-1-methyl-1-carbapen-2-em-3-carboxylate fluorosulfonate 200 mg of 4-nitrobenzyl (1R,5S,6S)-6-[(1R)-1-hydroxyethyl]-2-[(2S,4S)-2-[4-(2-hydroxyethyl)-4-methyl-1-piperazinylcarbonyl]-1-(4-nitrobenzyloxycarbonyl)-pyrrolidin-4-ylthio]-1-methyl-1-carbapen-2-em-3-carboxylate [prepared as described in step (2) above] were dissolved in 4 ml of methylene chloride, and the solution was placed on an ice bath. 40 μl of methyl fluorosulfonate were added to the solution, still on the ice bath, and the resulting mixture was stirred for 1 hour at room temperature. At the end of this time, the solvent was removed by distillation under reduced pressure. The crude product thus obtained was then dissolved in a mixture of 10 ml of tetrahydrofuran and 10 ml of water, and hydrogen gas was passed through the solution for 2 hours at room temperature in the presence of 200 mg of a 10% w/w palladium-on-carbon catalyst. The product was then treated, purified and lyophilized in a similar manner to that described in Example 1(3), to give 94 mg of the title compound.

Ultraviolet Absorption Spectrum (H$_2$O), $\lambda_{max}$ nm: 297.

High performance liquid chromatography:
Column: YMC ODS A-312;
Solvent: an 85:15 by volume mixture of 0.2% aqueous ammonium acetate and methanol;
Flow rate: 1.0 ml/min.;
Retention time: 15.15 min.

Infrared Absorption Spectrum (KBr), $v_{max}$ cm$^{-1}$: 1759, 1662, 1602, 1460, 1380, 1282.

Nuclear Magnetic Resonance Spectrum (D$_2$O, 270 MHz), δ ppm: 1.02 (3H, doublet, J=7.33 Hz); 1.10 (3H, doublet, J=6.34 Hz); 1.74–1.86 (1H, multiplet); 2.78–2.93 (1H, multiplet); 3.12, 3.13 (together 3H, two singlets); 3.12–3.34 (3H, multiplet); 3.37–3.98 (14H, multiplet); 4.00–4.12 (2H, multiplet); 4.57–4.66 (1H, multiplet).

EXAMPLE 13

(1R,5S,6S)-2-{(2S,4S)-2-[4-(2-Carbamoyloxyethyl)-4-methyl-1-piperaziniocarbonyl]pyrrolidin-4-ylthio}-6-[(1R)-1-hydroxyethyl]-1-methyl-1-carbapen-2-em-3-carboxylate fluorosulfonate

13(1)

(2S,4S)-2-[4-(2-Carbamoyloxyethyl)-1-piperazinylcarbonyl]-4-mercapto-1-(4-nitrobenzyloxycarbonyl)pyrrolidine trifluoromethanesulfonate 2.67 ml of trifluoroacetic acid and 122 μl of trifluoromethanesulfonic acid were added, whilst ice-cooling, to a solution of 417 mg of (2S,4S)-2-[4-(2-carbamoyloxyethyl)-1-piperazinylcarbonyl]-4-(4-methoxybenzylthio)-1-(4-nitrobenzyloxycarbonyl)pyrrolidine (prepared as described in Preparation 9) in 753 μl of anisole, and the resulting mixture was stirred at the same temperature for 1 hour. At the end of this time, the solvent was removed by distillation under reduced pressure, and the resulting residue was washed with diethyl ether by repeated decantation and dried under reduced pressure to give 325 mg of the title compound, as a powder.

Infrared Absorption Spectrum (KBr), $v_{max}$ cm$^{-1}$: 1707, 1608, 1524, 1438, 1347, 1280, 1169, 1030.

Nuclear Magnetic Resonance Spectrum (hexadeuterated dimethyl sulfoxide+D$_2$O, 270 MHz), δ ppm: 1.60–1.84 (1H, multiplet); 2.65–2.90 (1H, multiplet); 2.85–4.60 (14H, multiplet); 4.63–5.30 (4H, multiplet); 7.52, 7.64 (together 2H, two doublets, J=8.79 Hz); 8.23, 8.24 (together 2H, two doublets, J=8.79 Hz).

13(2) 4-Nitrobenzyl (1R,5S,6S)-2-{(2S,4S)-2-[4-(2-carbamoyloxyethyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 91 μl of diphenyl phosphorochloridate and 77 μl of diisopropylethylamine were added dropwise, whilst ice-cooling, to a solution of 152 mg of 4-nitrobenzyl (1R,5R,6S)-6-[(1R)-1-hydroxyethyl]-1-methyl-2-oxo-1-carbapenam-3-carboxylate in 2.0 ml of anhydrous acetonitrile, and the resulting mixture was stirred at the same temperature for 1 hour. At the end of this time, 176 μl of diisopropylethylamine and a solution of 318 mg of (2S,4S)-2-[4-(2-carbamoyloxyethyl)-1-piperazinylcarbonyl]-4-mercapto-1-(4-nitrobenzyloxycarbonyl)pyrrolidine trifluoromethanesulfonate [prepared as described in step (1) above] in 2.0 ml of anhydrous acetonitrile were then added dropwise to the mixture, whilst ice-cooling, and the mixture was stirred at the same temperature for 2 hours. At the end of this time, the reaction mixture was allowed to stand overnight in a refrigerator, after which it was freed from the solvent by distillation under reduced pressure. The resulting residue was mixed with an aqueous solution of sodium hydrogencarbonate and then extracted with ethyl acetate. The extract was dried over anhydrous magnesium sulfate, and the solvent was removed by distillation under reduced pressure. The resulting residue was purified by chromatography through a Lobar column (a product of Merk & Co., Inc., LiChroprep Si60, size B). Those fractions eluted with a 5:1 by volume mixture of ethyl acetate and methanol were collected and concentrated by evaporation under reduced pressure, to give 99 mg of the title compound as a powder.

Infrared Absorption Spectrum (KBr), $v_{max}$ cm$^{-1}$: 1773, 1711, 1650, 1521, 1345.

Nuclear Magnetic Resonance Spectrum (hexadeuterated dimethyl sulfoxide, 270 MHz), δ ppm: 1.15 (3H, doublet, J=6.35 Hz); 1.16 (3H, doublet, J=7.32 Hz); 1.51–1.72 (1H, multiplet); 2.10–2.57 (6H, multiplet); 2.72–2.93 (1H, multiplet); 3.06–4.30 (13H, multiplet); 4.76, 4.85 (together 1H, two triplets, J=7.81 Hz); 5.03–5.27 (3H, multiplet); 5.30, 5.46 (2H, AB-quartet, J=14.16 Hz); 6.46 (2H, broad singlet); 7.55, 7.65 (together 2H, two doublets, J=8.79 Hz); 7.72 (2H, doublet, J=8.79 Hz); 8.22, 8.23 (together 4H, two doublets, J=8.79 Hz).

13(3)

(1R,5S,6S)-2-{(2S,4S)-2-[4-(2-Carbamoyloxyethyl)-4-methyl-1-piperaziniocarbonyl]pyrrolidin-4-ylthio}-6-[(1R)-1-hydroxyethyl]-1-methyl-1-carbapen-2-em-3-carboxylate fluorosulfonate 20 μl of methyl fluorosulfonate were added to a solution of 94 mg of 4-nitrobenzyl (1R,5S,6S)-2-{(2S,4S)-2-[4-(2-carbamoyloxyethyl)-1-piperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (2) above] in 2.0 ml of anhydrous methylene chloride, and the resulting mixture was stirred at room temperature for 2 hours. At the end of this time, the solvent was removed by distillation under reduced pressure, and the resulting powdery residue was dissolved in 10 ml of a 1:1 by volume mixture of tetrahydrofuran and water, and hydrogenated at room temperature for 2 hours in the presence of 80 mg of a 10% w/w palladium-on-charcoal catalyst. The catalyst was then removed by filtration, and the filtrate was extracted twice with diethyl ether. The aqueous layer was concentrated by evaporation under reduced pressure and then lyophilized to give 70 mg of a powdery crude product. This crude product was subjected to column chromatography using a Lobar column (a product of Merck & Co., Inc., LiChroprep RP-8, size A) and the column was eluted with water. Those fractions containing the desired compound were collected and concentrated by evaporation under reduced pressure. The residue was lyophilized, to give 37 mg of the title compound as a colorless powder.

Infrared Absorption Spectrum (KBr), $v_{max}$ cm$^{-1}$: 1736, 1662, 1604, 1389, 1276, 1259, 1161.

Nuclear Magnetic Resonance Spectrum (D$_2$O, 270 MHz), δ ppm: 1.02 (3H, doublet, J=7.32 Hz); 1.09 (3H, doublet, J=6.35 Hz); 1.69–1.83 (1H, multiplet); 2.73–2.88 (1H, multiplet); 3.12, 3.13 (3H, two singlets); 3.15–3.30 (3H, multiplet); 3.41–3.62 (6H, multiplet); 3.65–3.91 (6H, multiplet); 3.97–4.12 (2H, multiplet); 4.34–4.42 (2H, multiplet); 4.49–4.64 (1H, multiplet).

EXAMPLE 14

(1R,5S,6S)-2-{(2S,4S)-2-[4-(2-Carbamoyloxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride 685 mg of the crude produce which was obtained as described in Example 13(3) were subjected to column chromatography using 280 ml of an ion-exchange resin (a product of Japan Organo Co., Ltd., Amberlite IRA-68, (CH$_3$)$_3$N$^-$ type) and the column was eluted with water. 1.1 ml of 1N aqueous hydrochloric acid was added to the combined fractions containing the desired compound, and the resulting mixture was concentrated by evaporation under reduced pressure and then lyophilized to give 573 mg of a powdery crude product. The whole of this crude product was subjected to column chromatography through a Lobar column (a product of Merck & Co., Inc., LiChroprep RP-8, size B) and the column was eluted with water containing 3% by volume methanol. The combined fractions containing the desired compound were collected and concentrated by evaporation under reduced pressure. The residue was lyophilized, to give 377 mg of the title compound as a colorless powder.

Infrared Absorption Spectrum (KBr), $v_{max}$ cm$^{-1}$: 1728, 1659, 1602, 1463, 1386, 1331, 1261.

Ultraviolet Absorption Spectrum (H$_2$O), $\lambda_{max}$ nm (ε): 295.6 (8,794).

Nuclear Magnetic Resonance Spectrum (D$_2$O, 270 MHz), δ ppm: 1.02 (3H, doublet, J=7.32 Hz); 1.09 (3H, doublet, J=6.35 Hz); 1.70–1.90 (1H, multiplet); 2.78–2.96 (1H, multiplet); 3.12, 3.14 (together 3H, two singlets); 3.11–3.32 (3H, multiplet); 3.40–3.95 (12H, multiplet); 3.98–4.13 (2H, multiplet); 4.32–4.44 (2H, multiplet); 4.60–4.77 (1H, multiplet).

EXAMPLE 15

(1R,5S,6S)-2-{(2S,4S)-2-[4-(2-Carbamoyloxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride 30 mg of the crude product which was obtained as described in Example 13(3) were subjected to column chromatography through 100 ml of an ion-exchange resin (Dowex 1-x4, 50–100 mesh, Cl$^-$ type) and the column was eluted with water. The combined fractions containing the title compound were concentrated by evaporation under reduced pressure, and the residue was lyophilized to give 16 mg of the title compound as a colorless powder. The infra-red and nuclear magnetic resonance spectra of the compound were precisely the same as those of the compound obtained as described in Example 14.

EXAMPLE 16

(1R,5S,6S)-2-[(2S,4S)-2-(4-Carbamoylmethyl-4-methyl-1-piperaziniocarbonyl)pyrrolidin-4-ylthio]-6-[(1R)-1-hydroxyethyl]-1-methyl-1-carbapen-2-em-3-carboxylate hydrochloride

16(1)

(2S,4S)-2-(4-Carbamoylmethyl-1-piperazinylcarbonyl)-4-mercapto-1-(4-nitrobenzyloxycarbonyl)pyrrolidine trifluoromethanesulfonate 2.88 ml of trifluoroacetic acid and 94 μl of trifluoromethanesulfonic acid were added to a suspension of 305 mg of (2S,4S)-2-(4-carbamoylmethyl-1-piperazinylcarbonyl)-4-(4-methoxybenzylthio)-1-(4-nitrobenzyloxycarbonyl)pyrrolidine (prepared as described in Preparation 10) in 577 μl of anisole, whilst ice-cooling, and then the resulting mixture was stirred at room temperature for 1 hour. It was then treated in a similar manner to that described in Example 13(1), to give 316 mg of the title compound as a powder.

Infrared Absorption Spectrum (KBr), $v_{max}$ cm$^{-1}$: 1700, 1608, 1523, 1440, 1409, 1348, 1278, 1255, 1227, 1170, 1030.

Nuclear Magnetic Resonance Spectrum (D$_2$O, 270 MHz), δ ppm: 1.56–1.72, 2.11–2.20 (together 1H, two multiplets); 2.62–2.72 (0.5H, multiplet); 2.90–4.02

(12.5H, multiplet); 3.82, 3.92 (together 2H, two singlets); 4.62–5.13 (3H, multiplet); 7.35 (1H, doublet, J=8.30 Hz); 7.42 (1H, doublet, J=8.79 Hz); 8.08 (1H, doublet, J=8.79 Hz); 8.10 (1H, doublet, J=8.30 Hz).

16(2) 4-Nitrobenzyl (1R,5S,6S)-2-[(2S,4S)-2-(4-carbamoylmethyl-1-piperazinylcarbonyl)pyrrolidin-4-ylthio]-6-[(1R)-1-hydroxyethyl]-1-methyl-1-carbapen-2-em-3-carboxylate 94 μl of diphenyl phosphorochloridate and 79 μl of diisopropylethylamine were added dropwise to a solution of 154 mg of 4-nitrophenyl (1R,5R,6S)-6-[(1R)-1-hydroxyethyl]-1-methyl-2-oxo-1-carbapenam-3-carboxylate in 1.7 ml of anhydrous acetonitrile, whilst ice-cooling, and the resulting mixture was stirred at the same temperature for 1 hour. 212 μl of diisopropylethylamine and a solution of 306 mg of (2S,4S)-2-(4-carbamoylmethyl-1-piperazinylcarbonyl)-4-mercapto-1-(4-nitrobenzyloxycarbonyl)pyrrolidine trifluoromethanesulfonate [prepared as described in step (1) above] in 2 ml of anhydrous acetonitrile were then added dropwise to the mixture, whilst ice-cooling, after which the mixture was stirred overnight at the same temperature. The mixture was then treated by a similar procedure to that described in Example 13(2), to give 125 mg of the title compound as a powder.

Infrared Absorption Spectrum (KBr), $\nu_{max}$ cm$^{-1}$: 1772, 1708, 1606, 1520, 1440, 1404, 1345.

Nuclear Magnetic Resonance Spectrum (CDCl$_3$, 270 MHz), δ ppm: 1.27, 1.28 (together 3H, two doublets, J=7.33 Hz); 1.37 (3H, doublet, J=6.34 Hz); 1.86–1.98 (1H, multiplet); 2.42–2.76 (5H, multiplet); 3.01, 3.07 (together 2H, two singlets); 3.23 (1H, doublet of doublets, J=6.83, 2.44 Hz); 3.31–4.30 (10H, multiplet); 4.73, 4.76 (together 1H, two triplets, J=7.81 Hz); 5.05–5.52 (6H, multiplet); 6.72, 6.87 (together 1H, two broad singlets); 7.37, 7.51 (together 2H, two doublets, J=8.79 Hz); 7.65 (2H, doublet, J=8.79 Hz); 8.20, 8.23 (together 4H, two doublets, J=8.79 Hz).

16(3) (1R,5S,6S)-2-[(2S,4S)-2-(4-Carbamoylmethyl-4-methyl-1-piperaziniocarbonyl)pyrrolidin-4-ylthio]-6-[(1R)-1-hydroxyethyl]-1-methyl-1-carbapen-2-em-3-carboxylate hydrochloride 24 μl of methyl fluorosulfonate were added to a solution of 123 mg of 4-nitrobenzyl (1R,5S,6S)-2-[(2S,4S)-2-(4-carbamoylmethyl-1-piperazinylcarbonyl)pyrrolidin-4-ylthio]-6-[(1R)-1-hydroxyethyl]-1-methyl-1-carbapen-2-em-3-carboxylate [prepared as described in step (2) above] in 2.3 ml of methylene chloride, whilst ice-cooling, and the resulting mixture was stirred at room temperature for 1 hour. At the end of this time, the solvent was removed by distillation under reduced pressure, and the residue was hydrogenated, separated and lyophlized following similar procedures to those described in Example 13(3). The resulting crude product was subjected to column chromatography using 100 ml of an ion-exchange resin (Dowex 1-x4, 50–100 mesh, Cl− type) and water as the eluent. Those fractions containing the title compound were collected, concentrated by evaporation under reduced pressure and lyophilized. The resulting powder was subjected to column chromatography through a Lobar column (LiChroprep RP-8, size A) using water as the eluent. Those fractions containing the title compound were collected, concentrated by evaporation under reduced pressure and lyophilized to give 34 mg of the title compound as a colorless powder.

Infrared Absorption Spectrum (KBr), $\nu_{max}$ cm$^{-1}$: 1754, 1694, 1660, 1600, 1453, 1386, 1259.

Ultraviolet Absorption Spectrum (H$_2$O), $\lambda_{max}$ nm: 297.5.

Nuclear Magnetic Resonance Spectrum (D$_2$O, 270 MHz), δ ppm: 1.02 (3H, doublet, J=7.32 Hz); 1.10 (3H, doublet, J=6.35 Hz); 1.72–1.83 (1H, multiplet); 2.76–2.88 (1H, multiplet); 3.13–3.30 (2H, multiplet); 3.26 (3H, singlet); 3.43–3.88 (11H, multiplet); 4.02–4.15 (4H, multiplet); 4.51–4.58 (1H, multiplet).

EXAMPLE 17
(1R,5S,6S)-2-[(2S,4S)-2-(4-Carboxymethyl-4-methyl-1-piperaziniocarbonyl)pyrrolidin-4-ylthio]-6-[(1R)-1-hydroxyethyl]-1-methyl-1-carbapen-2-em-3-carboxylate

17(1) (2S,4S)-4-Mercapto-2-[4-(4-nitrobenzyloxycarbonylmethyl)-1-piperazinylcarbonyl]pyrrolidine bis(trifluoromethanesulfonate)

8.0 ml of trifluoroacetic acid and 160 μl of trifluoromethanesulfonic acid were added, whilst ice-cooling, to a suspension of 1120 mg of (2S,4S)-4-(4-methoxybenzylthio)-2-[4-(4-nitrobenzyloxycarbonylmethyl)-1-piperazinylcarbonyl]-1-(4-nitrobenzyloxycarbonyl)pyrrolidine (prepared as described in Preparation 11) in 1.75 ml of anisole, and the resulting mixture was stirred at room temperature for 1.5 hours. At the end of this time, it was treated by a similar procedure to that described in Example 13(1), to give 1.58 g of the title compound as a powder.

Infrared Absorption Spectrum (KBr), $\nu_{max}$ cm$^{-1}$: 1756, 1704, 1667, 1523, 1441, 1348.

Nuclear Magnetic Resonance Spectrum (hexadeuterated dimethyl sulfoxide, 270 MHz), δ ppm: 1.60–1.76 (1H, multiplet); 2.70–2.85 (1H, multiplet); 3.08–3.42 (9H, multiplet); 3.65–3.83 (3H, multiplet); 3.94, 4.05 (together 1H, two doubled doublets, J=9.8 & 6.8 Hz); 4.72, 4.81 (together 1H, two triplets, J=8.1 Hz); 5.05–5.26 (2H, multiplet); 5.42, 5.43 (together 2H, two singlets); 7.52, 7.64, 7.69, 7.69, 7.70 (together 4H, four doublets, J=8.8 Hz); 8.23, 8.24, 8.28 (together 4H, three doublets, J=8.8 Hz).

17(2) 4-Nitrobenzyl (1R,5S,6S)-6-[(4R)-1hydroxyethyl]-1-methyl-2-{(2S,4S)-4-[4-(4-nitrobenzyloxycarbonylmethyl)-1-piperazinylcarbonyl]pyrrolidone-4-ylthio}-1-carbapen-2-em-3-carboxylate 290 μl of diphenyl phorphorochloridate and 245 μl of diisopropylethylamine were added dropwise, whilst ice-cooling, to a solution of 500 mg of 4-nitrobenzyl (1R,5R,6S)-6-[(1R)-1-hydroxyethyl-1-methyl-2-oxo-1-carbapenam-3-carboxylate in 5 ml of anhydrous acetonitrile, and the resulting mixture was stirred at the same temperature for 1 hour. At the end of this time, 520 μl of diisopropylethylamine an a solution of 1.57 g of (2S,4S)-4-mercapto-2-[4-(4-nitrobenzyloxycarbonylmethyl)-1-piperazinylcarbonyl)pyrrolidone bis(trifluoromethanesulfonate) [prepared as described in step (1)] in 5 ml of anhydrous acetonitrile were added to the mixture. The resulting mixture was then stirred overnight at the same temperature, after which the reaction mixture was treated and purified by a procedure similar to that described in Example 13(2), to give 706 mg of the title compound as a powder.

Infrared Absorption Spectrum (KBr), $v_{max}$ cm$^{-1}$: 1772, 1710, 1654, 1521, 1346.

Nuclear Magnetic Resonance Spectrum (CDCl$_3$, 270 MHz), δppm: 1.27 (3H, doublet, J=7.3 Hz); 1.37 (3H, doublet, J=5.9 Hz); 1.85–2.06 (2H, multiplet); 2.53–2.77 (5H, multiplet); 3.25–3.76 (10H, multiplet); 4.03–4.28 (3H, multiplet); 4.67–4.79 (1H, multiplet); 5.06–5.52 (6H, multiplet); 7.43–7.66 (6H, multiplet); 8.20–8.25 (6H, multiplet).

17(3)
(1R,5S,6S)-2-[(2S,4S)-2-(4-Carboxymethyl-4-methyl-1-piperaziniocarbonyl)pyrrolidin-4-ylthio]-6-[(1R)-1-hydroxyethyl]-1-methyl-1-carbapen-2-em-3-carboxylate 90 μl of methyl fluorosulfonate were added, whilst ice-cooling, to a solution of 700 mg of 4-nitrobenzyl (1R,5S,6S)-6-[(1R)-1-hydroxyethyl]-2-{(2S,4S)-2-[4-(4-nitrobenzyloxycarbonylmethyl)-1-piperazinylcarbonyl]-pyrrolidine-4-ylthio}-1-methyl-1-carbapen-2-em-3-carboxylate [prepared as described in step (1) above] in 20 ml of anhydrous methylene chloride, and the resulting mixture was stirred at room temperature for 1 hour. At the end of this time, the solvent was removed by distillation under reduced pressure, and the resulting residue was dissolved in a 1:1 by volume mixture of tetrahydrofuran and water and hydrogenated at room temperature for 3 hours in the presence of 1.4 g of a 10% w/w palladium-on-charcoal catalyst. The catalyst was then removed by filtration, and the filtrate was extracted with 100 ml of diethyl ether. The aqueous layer was then concentrated by evaporation under reduced pressure to a volume of 20 ml and lyophilized to afford 410 mg of a crude product as a powder. The whole of this crude product was then subjected to column chromatography through two Lobar columns (RP-8, size B) using, first, 300 ml of water and, subsequently, 200 ml of water containing 2% by volume of methanol as the eluents. Those fractions containing the title compound were collected, concentrated by evaporation under reduced pressure and lyophilized, to give 200 mg of the title compound as a colorless powder.

Infrared Absorption Spectrum (KBr), $v_{max}$ cm$^{-1}$: 1756, 1634, 1386, 1259.

Ultraviolet Absorption Spectrum (H$_2$O), $\lambda_{max}$ nm: 296.6.

Nuclear Magnetic Resonance Spectrum (D$_2$O, 270 MHz), δppm: 1.02 (3H, doublet, J=7.3 Hz); 1.10 (3H, doublet, J=6.3 Hz); 1.74–1.84 (1H, multiplet); 2.80–2.91 (1H, multiplet); 3.21, 3.22 (together 3H, two singlets); 3.12–3.29 (4H, multiplet); 3.44–4.10 (16H, multiplet); 4.57–4.67 (1H, multiplet).

EXAMPLE 18
(1R,5S,6S)-2-[(2S,4S)-2-(4-Carboxymethyl-4-methyl-1-homopiperaziniocarbonyl)pyrrolidin-4-ylthio]-6-[(1R)-1-hydroxyethyl]-1-methyl-1-carbapen-2-em-3-carboxylate

18(1)
(2S,4S)-4-Mercapto-2-[4-(4-nitrobenzyloxycarbonylmethyl)-1-homopiperazinylcarbonyl]-1-(4-nitrobenzyloxycarbonyl)pyrrolidine bis(trifluoromethanesulfonate)

15 ml of trifluoroacetic acid and 0.36 ml of trifluoromethanesulfonic acid were added to a solution of 1.47 g of (2S,4S)-4-(4-methoxybenzylthio)-2-[4-(4-nitrobenzyloxycarbonylmethyl)-1-homopiperazinylcarbonyl]-1-(4-nitrobenzyloxycarbonyl)pyrrolidine (prepared as described in Preparation 12) in 2.2 ml of anisole, and the resulting mixture was stirred at room temperature for 1 hour. At the end of this time, the reaction mixture was treated by a procedure similar to that described in Example 13(1), to give 1.8 g of the title compound as a powder.

Infrared Absorption Spectrum (KBr), $v_{max}$ cm$^{-1}$: 1757, 1700, 1608, 1523, 1441, 1408, 1348.

Nuclear Magnetic Resonance Spectrum (hexadeuterated dimethyl sulfoxide, 270 MHz), δppm: 1.61–1.80 (1H, multiplet); 2.00–2.28 (2H, multiplet); 2.65–2.86 (1H, multiplet); 3.08–4.24 (13H, multiplet); 4.31–4.48 (2H, multiplet); 5.02–5.37 (2H, multiplet); 5.42 (2H, singlet); 7.52, 7.62 (together 2H, two doublets, J=8.30 Hz); 7.69 (2H, doublet, J=8.79 Hz); 8.23 (2H, doublet, J=8.79 Hz); 8.27 (2H, doublet, J=8.30 Hz).

18(2) 4-Nitrobenzyl (1R,5S,6S)-6-[(1R)-1-hydroxyethyl]-1-methyl-2-{(2S,4S)-2-[4-(4-nitrobenzyloxycarbonylmethyl)-1-homopiperazinylcarbonyl]-1-(4-nitrobenzyloxycarbonyl)pyrrolidin-4-ylthio}-1-carbapen-2-em-3-carboxylate 0.37 ml of diphenyl phosphorochloridate and 0.31 ml of diisopropylethylamine were added dropwise, whilst ice-cooling, to a solution of 580 mg of 4-nitrobenzyl (1R,5R,6S)-6-[(1R)-1-hydroxyethyl]-1-methyl-2-oxo-1-carbapenam-3-carboxylate in 10 ml of anhydrous acetonitrile, and the resulting mixture was stirred at the same temperature for 1 hour. At the end of this time, 0.99 ml of diisopropylethylamine and a solution of 1.43 g of (2S,4S)-4-mercapto-2-[4-(4-nitrobenzyloxycarbonylmethyl)-1-homopiperazinylcarbonyl]-1-(4-nitrobenzyloxycarbonyl)pyrrolidine bis(trifluoromethanesulfonate) [prepared as described in step (1) above] in 10 ml of anhydrous acetonitrile were added to the mixture, whilst ice-cooling, and the mixture was then stirred overnight at the same temperature. The reaction mixture was then treated and purified by procedures similar to those described in Example 13(2), to give 1.1 g of the title compound as a powder.

Infrared Absorption Spectrum (KBr), $v_{max}$ cm$^{-1}$: 1771, 1709, 1647, 1606, 1521, 1346.

Nuclear Magnetic Resonance Spectrum (CDCl$_3$, 270 MHz), δppm: 1.28 (3H, doublet, J=6.84 Hz); 1.37 (3H, doublet, J=6.35 Hz); 1.74–2.04 (4H, multiplet); 2.62–2.96 (6H, multiplet); 3.27 (1H, doublet of doublets, J=6.83 & 2.44 Hz); 3.34–3.79 (9H, multiplet); 4.19–4.27 (2H, multiplet); 4.66–4.77 (1H, multiplet); 5.06–5.52 (6H, multiplet); 7.45–7.52 (4H, multiplet); 7.65 (2H, doublet, J=8.79 Hz); 8.23 (6H, doublet, J=8.79 Hz).

18(3)
(1R,5S,6S)-2-[(2S,4S)-2-(4-Carboxymethyl-4-methyl-1-homopiperaziniocarbonyl)pyrrolidin-4-ylthiol]-6-[(1R)-1-hydroxyethyl]-1-methyl-1-carabapen-2-em-3-carboxylate 0.17 ml of methyl fluorosulfonate was added, whilst ice-cooling, to a solution of 1.05 g of 4-nitrobenzyl (1R,5S,6S)-6-[(1R)-1-hydroxyethyl]-1-methyl-2-{(2S,4S)- 2-[4-(4-nitrobenzyloxycarbonylmethyl)-1-homopiperazinylcarbonyl]-1-(4-nitrobenzyloxycarbonyl)pyrrolidin-4-ylthio}-1-carbapen-2-em-3-carboxylate [prepared as described in step (2) above] in 20 ml of anhydrous methylene chloride, and the resulting mixture was stirred at room temperature for 1 hour. At the end of this time, the solvent was removed by distillation under reduced pressure, and the resulting residue was hydrogenated, treated and lyophilized using similar procedures to those described in Example 17(3). The resulting crude product was then subjected to column chromatography using a Lobar column (RP-8, size B) and water containing 1% by volume methanol as the eluent. The chromatography separated the crude product into two isomers of the title compound, isomers A and B. Each fraction was concentrated by evaporation under reduced pressure and lyophilized to give 32.4 mg of isomer A and 43.0 mg of isomer B, respectively, both as colorless powders.

Isomer A:

High performance liquid chromatography:
column: YMC ODS AQ-312,
solvent: 0.2% aqueous ammonium acetate/methanol (90:10 by volume),
flow rate: 1.0 ml/min,
retention time: 7.76 min.

Infrared Absorption Spectrum (KBr), $\nu_{max}$ cm$^{-1}$: 1761, 1660, 1455, 1382, 1258.

Ultraviolet Absorption Spectrum (H$_2$O), $\lambda_{max}$ nm:

Nuclear Magnetic Resonance Spectrum (D$_2$, 270 MHz), δppm: 1.22 (3H, doublet, J=7.32 Hz); 1.29 (3H, doublet, J=6.35 Hz); 1.97-2.08 (1H, multiplet); 2.20-2.45 (2H, multiplet); 3.02-3.14 (1H, multiplet); 3.30-3.58 (3H, multiplet); 3.32, 3.36 (together 3H, two singlets); 3.61-4.09 (12H, multiplet); 4.21-4.30 (2H, multiplet); 4.70-4.89 (1H, multiplet).

Isomer B:

High performance liquid chromatography:
column: YMC ODC AQ-312,
solvent: 0.2% aqueous ammonium acetate/methanol (90:10 by volume),
flow rate: 1.0 ml/min,
retention time: 8.18 min.

Infrared Absorption Spectrum (KBr), $\nu_{max}$ cm$^{-1}$: 1752, 1634, 1464, 1386, 1290.

Ultraviolet Absorption Spectrum (H$_2$O), $\lambda_{max}$ nm: 296.8.

Nuclear Magnetic Resonance Spectrum (D$_2$O, 270 MHz), δppm: 1.22 (3H, doublet, J=7.33 Hz); 1.30 (3H, doublet, J=6.34 Hz); 1.96-2.06 (1H, multiplet); 2.27-2.50 (2H, multiplet); 2.96-3.12 (1H, multiplet); 3.28-3.56 (3H, multiplet); 3.33, 3.35 (together 3H, two singlets); 3.59-4.14 (12H, multiplet); 4.21-4.30 (2H, multiplet); 4.72-4.89 (1H, multiplet).

EXAMPLE 19

(1R,5S,6S)-6-[(1R)-1-Hydroxyethyl]-1-methyl-2-[(2S,4S)-2-(3,4,4-trimethyl-1-piperaziniocarbonyl)pyrrolidin-4-ylthio]-1-carbapen-2-em-3-carboxylate hydrochloride

19(1)

(2S,4S)-2-(3,4-Dimethyl-1-piperazinylcarbonyl)-4-mercapto-1-(4-nitrobenzyloxycarbonyl)pyrrolidine bis(trifluoromethanesulfonate)

9.4 ml of trifluoroacetic acid and 0.31 ml of trifluoromethanesulfonic acid were added, whilst ice-cooling, to a solution of 940 mg of (2S,4S)-2-(3,4-dimethyl-1-piperazinylcarbonyl)-4-(4-methoxybenzylthio)-1-(4-nitrobenzyloxycarbonyl)pyrrolidine (prepared as described in Preparation 13) in 1.88 ml of anisole, and the resulting mixture was stirred at room temperature for 1 hour. At the end of this time, the reaction mixture was treated in a similar manner to that described in Example 13(1), to give 1.2 g of the title compound as a powder.

Infrared Absorption Spectrum (liquid film), $\nu_{max}$ cm$^{-1}$: 1705, 1665, 1608, 1524, 1462, 1440, 1407, 1348.

Nuclear Magnetic Resonance Spectrum (hexadeuterated dimethyl sulfoxide, 270 MHz), δppm: 1.25, 1.28 (together 3H, two doublets, J=6.59 Hz); 1.62-1.73 (1H, multiplet); 2.68-3.70 (9H, multiplet); 2.84 (3H, singlet); 3.90-4.44 (4H, multiplet); 4.70-5.27 (2H, multiplet); 7.50, 7.63 (together 2H, two doublets, J=8.79 Hz); 8.24 (2H, doublet, J=8.79 Hz).

19(2) 4-Nitrobenzyl (1R,5S,6S)-2-[(2S,4S)-2-(3,4-dimethyl-1-piperazinylcarbonyl)-1-(4-nitrobenzyloxycarbonyl)pyrrolidin-4-ylthio]-6-[(1R)-1-hydroxyethyl]-1-methyl-1-carbapen-2-em-3-carboxylate 0.30 ml of diphenyl phosphorochloridate and 0.25 ml of diisopropylethylamine were added, whilst ice-cooling, to a solution of 470 mg of 4-nitrobenzyl (1R,5R,6S)-6-[(1R)-1-hydroxyethyl]-1-methyl-2-oxo-1-carbapenam-3-carboxylate in 9 ml of anhydrous acetonitrile, and the resulting mixture was stirred at the same temperature for 1 hour. At the end of this time, 0.88 ml of diisopropylethylamine and a solution of 970 mg of (2S,4S)-2-(3,4-dimethyl-1-piperazinylcarbonyl)-4-mercapto-1-(4-nitrobenzyloxycarbonyl)pyrrolidine bis(trifluoromethanesulfonate) [prepared as described in step (1) above] in 8 ml of anhydrous acetonitrile were then added dropwise to the mixture, and the resulting mixture was stirred overnight at the same temperature. The reaction mixture was then treated and purified in a similar manner to that described in Example 13(2), to give 620 mg of the title compound as a powder.

Infrared Absorption Spectrum (KBr), $\nu_{max}$ cm$^{-1}$: 1773, 1711, 1652, 1606, 1521, 1440, 1404, 1345.

Nuclear Magnetic Resonance Spectrum (CDCl$_3$, 270 MHz), δppm: 1.08 (3H, doublet, J=6.35 Hz); 1.28 (3H, doublet, J=6.84 Hz); 1.37 (3H, doublet, J=6.35 Hz); 1.80-2.18 (4H, multiplet); 2.30 (3H, singlet); 2.58-3.10 (4H, multiplet); 3.27 (1H, doublet of doublets, J=6.83 & 2.44 Hz); 3.31-3.76 (5H, multiplet); 4.02-4.35 (3H, multiplet); 4.68-4.78 (1H, multiplet); 5.21-5.52 (4H, multiplet); 7.42, 7.52 (together 2H, two doublets, J=8.79 Hz); 7.65 (2H, doublet, J=8.79 Hz); 8.19, 8.23 (together 4H, two doublets, J=8.79 Hz).

19(3)

(1R,5S,6S)-6-[(1R)-1-Hydroxyethyl]-1-methyl-2-[(2S,4S)-2-(3,4,4-trimethyl-1-piperaziniocarbonyl)pyrrolidin-4-ylthio]-1-carbapen-2-em-3-carboxylate hydrochloride 0.13 ml of methyl fluorosulfonate was added, whilst ice-cooling, to a solution of 620 mg of 4-nitrobenzyl (1R,5S,6S)-2-[(2S,4S)-2-(3,4-dimethyl-1-piperazinylcarbonyl)-1-(4-nitrobenzyloxycarbonyl)pyrrolidin-4-yl-3-carboxylate [prepared as described in step (2) above] in 12 ml of anhydrous methylene chloride, and the resulting mixture was stirred at room temperature for 1 hour. At the end of this time, the solvent was removed by distillation under reduced pressure, and the resulting residue was hydrogenated, treated and lyophilized in a similar manner to that described in Example 13(3). The resulting crude product was subjected to column chromatography using 300 ml of an ion-exchange resin (Dowex 1-x4, 50 mesh, Cl$^-$ type) and the column was eluted with water. Those fractions containing the title compound were collected and lyophilized. The powder thus obtained was injected into a Lobar column (RP-8, size B) and the column was eluted with water containing 2% by volume methanol. The combined fractions containing the title compound were concentrated by evaporation under reduced pressure and lyophilized to afford 150 mg of the title compound as a colorless powder.

Infrared Absorption Spectrum (H$_2$O), $\nu_{max}$ cm$^{-1}$: 1757, 1660, 1597, 1465, 1382, 1267.

Ultraviolet Absorption Spectrum (H$_2$O), $\lambda_{max}$ nm: 295.9.

Nuclear Magnetic Resonance Spectrum (D$_2$O, 270 MHz), δppm: 1.03 (3H, doublet, J=7.33 Hz); 1.10 (3H, doublet, J=6.35 Hz); 1.25, 1.27 (together 3H, two doublets, J=6.35 Hz); 1.80–1.85 (1H, multiplet); 2.85–2.97 (1H, multiplet); 2.94 (3H, singlet); 3.06, 3.07 (together 3H, two singlets); 3.11–3.85 (10H, multiplet); 3.72–3.92 (1H, multiplet); 4.04–4.46 (3H, multiplet); 4.63–4.75 (1H, multiplet).

EXAMPLE 20

(1R,5S,6S)-2-{(2S,4S)-2-[4-(2-Hydroxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride 407 mg of (1R,5S,6S)-2-[(2S,4S)-2-[4-(2-hydroxyethyl)-4-methyl-1-piperaziniocarbonyl]pyrrolidin-4-ylthio]-6-[(1R)-1-hydroxy-ethyl]-1-methyl-1-carbapen-2-em-3-carboxylate fluorosulfonate [prepared as described in Example 12(3)] were subjected to column chromatography through 200 ml of an ion-exchange resin (Dowex 1-x4, 50–100 mesh, Cl$^-$ type) using water as the eluent. Those fractions containing the title compound were collected and lyophilized. The powder thus obtained was injected in to a Lobar column (RP-8, size B) and the column was eluted with water containing 2% by volume of methanol. The combined fractions containing the title compound were concentrated by evaporation under reduced pressure and lyophilized to afford 108 mg of the title compound as a colorless powder.

Infrared Absorption Spectrum (KBr), $\nu_{max}$ cm$^{-1}$: 1762, 1661, 1608, 1554, 1464, 1378, 1263.

Ultraviolet Absorption Spectrum (H$_2$O), $\lambda_{max}$ nm (ε): 296.5 (8,226).

Nuclear Magnetic Resonance Spectrum (D$_2$O, 270 MHz), δppm: 1.02 (3H, doublet, J=7.32 Hz); 1.07 (3H, doublet, J=6.34 Hz); 1.77–1.90 (1H, multiplet); 2.82–2.94 (1H, multiplet); 3.12, 3.13 (together 3H, two singlets); 3.12–3.24 (1H, multiplet); 3.27–3.37 (2H, multiplet); 3.38–4.00 (14H, multiplet); 4.01–4.11 (2H, multiplet); 4.66–4.75 (1H, multiplet).

EXAMPLE 21

(1R,5S,6S)-2-{(2S,4S)-6-[(1R)-1-Hydroxyethyl]-2-[4-(2-hydroxyethyl)-4-methyl-1-piperaziniocarbonyl]-pyrrolidin-4-ylthio}-1-methyl-1-carbapen-2-em-3-carboxylate hydrochloride

21(1)

(2S,4S)-4-Mercapto-2-{4-[2-(4-nitrobenzyloxycarbonyl)oxyethyl]-1-piperazinylcarbonyl}-1-(4-nitrobenzyloxycarbonyl)pyrrolidine bis(trifluoromethanesulfonate)

135.75 mg of trifluoroacetic acid and 6.18 ml of trifluoromethanesulfonic acid were added, whilst ice-cooling, to a solution of 26.00 g of (2S,4S)-4-(4-methoxybenzylthio)-2-{4-[2-(4-nitrobenzyloxycarbonyl)oxyethyl]-1-piperazinylcarbonyl}-1-(4-nitrobenzyloxycarbonyl)pyrrolidine (prepared as described in Preparation 14) in 38.8 ml of anisole, and the resulting mixture was stirred at the same temperature for 1.5 hours. At the end of this time, the solvent was removed by distillation under reduced pressure, and the resulting residue was washed with diethyl ether by repeated decantation and dried under reduced pressure to give 32.5 g of the title compound as a powder.

21(2) 4-Nitrobenzyl (1R,5S,6S)-6-[(1R)-1-hydroxyethyl]-1-methyl-2-{(2S,4S)-2-[4-(2-4'-nitrobenzyloxycarbonyloxyethyl)-1-piperazinylcarbonyl]-1-(4-nitrobenzyloxycarbonyl)pyrrolidin-4-ylthio}-1-carbapen-2-em-3-carboxylate 6.38 ml of diphenyl phosphorochloridate and 5.37 ml of diisopropylethylamine were added dropwise, whilst ice-cooling, to a solution of 10.63 g of 4-nitrobenzyl (1R,5R,6S)-6-[(1R)-1-hydroxyethyl]-1-methyl-2-oxo-1-carbapenam-3-carboxylate in 75 ml of anhydrous acetonitrile, and the resulting mixture was stirred at the same temperature for 1 hour. At the end of this time, 16.26 ml of diisopropylethylamine and a solution of 32.5 g of (2S,4S)-4-mercapto-4-(4-methoxybenzylthio)-2-{4-[2-(4-nitrobenzyloxycarbonyl)oxyethyl]-1-piperazinylcarbonyl}-1-(4-nitrobenzyloxycarbonyl)pyrrolidine bis(trifluoromethanesulfonate) [prepared as described in step (1) above] in 65 ml of anhydrous acetonitrile were added dropwise to the mixture, whilst ice-cooling, and the temperature for 1 hour, after which it was allowed to stand at room temperature overnight. At the end of this time, the solvent was removed by distillation under reduced pressure, and the resulting residue was mixed with an aqueous solution of sodium hydrogencarbonate and extracted with ethyl acetate. The extract was dried over anhydrous magnesium sulfate and freed from the solvent by distillation. The residue was subjected to column chromatography through silica gel. Those fractions eluted with an 18:1 by volume mixture of ethyl acetate and methanol were collected and concentrated by evaporation under reduced pressure, to give 19.75 g of the title compound as a powder.

Infrared Absorption Spectrum (KBr), $\nu_{max}$ cm$^{-1}$: 1769, 1751, 1710, 1653, 1607, 1521, 1443, 1347.

Nuclear Magnetic Resonance Spectrum (CDCl$_3$, 270 MHz), δppm: 1.27, 1.28 (together 3H, two doublets, J=7.33 Hz); 1.37 (3H, doublet, J=6.35 Hz); 1.78–1.98 (1H, multiplet); 2.31–2.80 (7H, multiplet); 3.27 (1H, doublet of doublets, J=6.83 & 2.44 Hz); 3.31—3.76 (8H, multiplet); 4.01–4.33 (5H, multiplet); 4.68, 4.74 (together 1H, two triplets, J=7.81 Hz); 5.04–5.52 (6H, multiplet); 7.44, 7.51 (together 2H, two doublets, J=8.79 Hz); 7.55, 7.65 (together 4H, two doublets, J=8.79 Hz); 8.17–8.25 (6H, multiplet).

21(3)

(1R,5S,6S)-6-[(1R)-1-hydroxyethyl]-2-{(2S,4S)-2-[4-(2-Hydroxyethyl)-4-methyl-1-piperaziniocarbonyl]pyrrolidin-4-ylthio}-1-methyl-1-carbapen-2-em-3-carboxylate hydrochloride 0.584 g of methyl fluorosulfonate was added, whilst ice-cooling, to a solution of 4.47 g of 4-nitrobenzyl (1R,5S,6S)-6-[(1R)-1-hydroxyethyl]-1-methyl-2-{(2S,4S)-2-[4-(2-4'-nitrobenzyloxycarbonyloxyethyl)-1-piperazinylcarbonyl]-1-(4-nitrobenzyloxycarbonyl)pyrrolidin-4-ylthio}-1-carbapen-2-em-3-carboxylate [prepared as described in step (2) above] in 45 ml of anhydrous acetonitrile, and the resulting mixture was stirred at the same temperature for 1 hour. At the end of this time, the solvent was removed by distillation under reduced pressure, and the resulting residue was hydrogenated, treated and lyophilized according to the procedure described in Example 13(3). The resulting crude product was then subjected to column chromatography through 200 ml of an ion-exchange resin (Dowex 1-x4, 100–200 mesh, Cl⁻ type), using water as the eluent. The combined fractions containing the title compound were lyophilized, and the powder thus obtained was purified by reverse phase column chromatography through silica gel (a product of Merck & Co., Inc., LiChroprep Rp-8, 30 ml), using water containing 1.5% by volume of methanol as the eluent. Those fractions containing the title compound were collected, concentrated by evaporation under reduced pressure and lyophilized, to give 1.73 g of the title compound as a colorless powder. The spectral data (infra-red absorption, ultra-violet absorption and nuclear magnetic resonance spectra) of the product were identical to those of the compound prepared as described in Example 20.

EXAMPLE 22

(1R,5S,6S)-2-{(2S,4S)-6-[(1R)-1-Hydroxyethyl]-2-[4-(2-hydroxyethyl)-4-methyl-1-piperaziniocarbonyl]-pyrrolidin-4-ylthio}-1-methyl-1-carbapen-2-em-3-carboxylate hydrochloride

22(1)

(1R,5S,6)-2-{(2S,4S)-6-[(1R)-1R)-1-Hydroxyethyl]-2-[4-(2-hydroxyethyl)-4-methyl-1-piperaziniocarbonyl]-pyrrolidin-4-ylthio}-1-methyl-1-carbapen-2-em-3-carboxylate hydrochloride 1.95 ml of methyl fluorosulfonate were added dropwise, whilst ice-cooling, to a solution of 21.8 g of 4-nitrobenzyl (1R,5S,6S)-6-[(1R)-1-hydroxyethyl]-1-methyl-2-{(2S,4S)-2-[4-(2-4'-nitrobenzyloxycarbonyloxyethyl)-1-piperazinylcarbonyl]-1-(4-nitrobenzyloxycarbonyl)pyrrolidin-4-ylthio}-1-carbapen-2-em-3-carboxylate [prepared as described in Example 21(2)], dissolved in 200 ml of anhydrous acetonitrile, and the resulting mixture was stirred under the same conditions for 1 hour, after which it was concentrated by evaporation under reduced pressure. The powdery residue (24.9 g) thus obtained was dissolved in 400 ml of a 1:1 by volume mixture of tetrahydrofuran and water and hydrogenated in the presence of 20 g of a 10% w/w palladium-on-carbon catalyst for 2.5 hours on a water bath which was kept at about 20° C. At the end of this time, the catalyst was removed by filtration and the filtrate was extracted three times, each time with 300 ml of diethyl ether. The aqueous layer was then concentrated by evaporation under reduced pressure to a volume of about 100 ml and was then subjected to column chromatography through 500 ml of an ion exchange resin (Dowex 1 -x4, 50–100 mesh, Cl⁻ type) using water as an eluent. The eluent containing the desired compound was concentrated by evaporation under reduced pressure to a volume of about 110 ml and the concentrate was purified by chromatography through a reverse phase column (LiChrocrep RP-8; 200 ml) using water as the eluent. Those fractions containing the desired compound were collected and concentrated by evaporation under reduced pressure to a volume of about 20 ml. The concentrate was diluted with 50 ml of methanol, and the resulting solution was added dropwise to 800 ml of acetone to afford a powdery precipitate, which was collected by filtration, washed with 100 ml of acetone and dried to afford 8.2 g of the desired compound as a colorless powder. The spectral data (infra-red absorption, ultra-violet absorption and nuclear magnetic resonance spectra) of the product were identical to those of the compound prepared as described in Example 20.

EXAMPLE 23

The following steps (23(1) and 23(2)) provide an alternative method of preparing the compound which is also prepared in Example 21(2) and which is used as a starting material in steps 22(1) and in 21(3). The product may be used in those steps to prepare a compound of the present invention.

23(1)

(2S,4S)-4-Mercapto-2-{4-[2-(p-nitrobenzyloxycarbonyl)oxyethyl]-1-piperazinylcarbonyl}-1-(p-nitrobenzyloxycarbonyl)pyrrolidine 600 ml of a methanolic solution containing 10% w/v hydrogen chloride were added to a solution of 140 g of (2S,4S)-4-acetylthio-2-{4-[2-(4-nitrobenzyloxycarbonyl)oxyethyl] -1-piperazinylcarbonyl)-1-(4-nitrobenzyloxycarbonyl)pyrrolidine dissolved in 150 ml of dioxane, and the resulting mixture was stirred at 50° C. for 1 hour. At the end of this time, the mixture was concentrated by evaporation under reduced pressure, and the concentrate was diluted with 1500 ml of ethyl acetate, after which it was neutralized with a saturated aqueous solution of sodium hydrogencarbonate. The mixture was then washed with 300 ml of water and with 300 ml of an aqueous solution of sodium chloride, after which it was freed from the solvent by distillation under reduced pressure. The residue thus obtained was subjected to column chromatography through silica gel using mixtures of ethyl acetate and methanol ranging from 30:1 to 20:1 by volume as the eluent. Those fractions containing the desired compound were collected and concentrated to afford 96.44 g of the title compound as a colorless powder.

Infrared Absorption Spectrum (KBr), $\nu_{max}$ cm⁻¹: 2530, 1742, 1710, 1653, 1521, 1347.

Nuclear Magnetic Resonance Spectrum (CDCl₃, 270 MHz), δppm: 1.83 (1H, multiplet); 2.44–2.79 (7H, multiplet); 3.22–3.64 (6H, multiplet); 4.06–4.17 (1H, multiplet); 4.26–4.36 (2H, multiplet); 4.60–4.71 (1H, multiplet); 5.02–5.33 (4H, multiplet); 7.42–7.58 (4H, multiplet); 8.17–8.26 (4H, multiplet).

23(2) 4-Nitrobenzyl (1R,5S,6)-6-[(1R)-1-hydroxyethyl]-2-{(2S,4S)-[4-(2-p'-nitrobenzyloxycarbonyloxyethyl)-1-piperazinylcarbonyl]-1-(p-nitrobenzyloxycarbonyl)pyrrolidin-4-ylthio}-1-methyl-1-carbapen-2-em-3-carboxylate 675 μl of diphenyl chlorophosphate and 567 μl of diisopropylethylamine were added dropwise, whilst ice-cooling, to a solution of 1.12 g of 4-nitrobenzyl (1R,5R,6S)-6-[(1R)-1-hydroxyethyl]-1-methyl-2-oxo-1-carbapenam-3-carboxylate dissolved in 10 ml of anhydrous acetonitrile, and the resulting mixture was stirred at the same temperature for 1 hour. At the end of this time, a solution of 2.30 g of (2S,4S)-4-mercapto-2-{4-[2-(p-nitrobenzyloxycarbonyl)oxyethyl]-1-piperazinylcarbonyl}-1-(p-nitrobenzyloxycarbonyl)pyrrolidine [prepared as described in step (2) above] in 5 ml of anhydrous acetonitrile was added dropwise to the mixture, and the resulting mixture was stirred at the same temperature for 1 hour. The reaction mixture was then treated and purified according to the same procedure as described in Example 21(2), to give 2.70 g of the title compound as a powder. The infra-red absorption spectrum and nuclear magnetic resonance spectrum of the product were identical with those of the compound obtained as described in Example 21(2).

The following steps 23(3) and 23(4) provide two further alternative methods of preparing the compound which is also prepared in Example 21(2) and which is used as a starting material in Example 21(3) and in Example 22(1). The product may be used in those Examples to prepare a compound of the present invention.

23(3) 4-Nitrobenzyl
(1R,5S,6S)-6-[(1R)-1-hydroxyethyl]-2-{(2S,4S)-[4-(2-p'-nitrobenzyloxycarbonyloxyethyl)-1-piperazinylcarbonyl]-1-(p-nitrobenzyloxycarbonyl)pyrrolidin-4-ylthio}-1-methyl-1-carbapen-2-em-3-carboxylate A solution of 28.3 mg of 4-nitrobenzyl (1R,5S,6S)-6-[(1R)-1-hydroxyethyl]-1-methyl-2-phenylsulfinyl-1-carbapen-2-em-3-carboxylate and 7.8 mg of diisopropylethylamine in 1 ml of anhydrous acetonitrile was added dropwise to a solution of 112 mg of (2S,4S)-{4-[2-(4-nitrobenzyloxycarbonyl)oxyethyl]-1-piperazinylcarbonyl}-5-mercapto-1-(4-nitrobenzyloxycarbonyl)pyrrolidine in 0.5 ml of anhydrous acetonitrile, whilst ice-cooling, and the resulting mixture was stirred at the same temperature for 1 hour. At the end of this time, the solvent was removed by distillation under reduced pressure, and the resulting residue was purified by column chromatography through silica gel using a 20:1 by volume mixture of ethyl acetate and methanol as the eluent, to afford 14 mg of the title compound as a powder. The infra-red absorption spectrum and nuclear magnetic resonance spectrum of the product were identical with those of the compound obtained as described in Example 21(2).

23(4) 4-Nitrobenzyl
(1R,5S,6S)-6-[(1R)-1-hydroxyethyl]-2-{(2S,4S)-[4-(2-p'-nitrobenzyloxycarbonyloxyethyl)-1-piperazinylcarbonyl]-1-(p-nitrobenzyloxycarbonyl)pyrrolidin-4-ylthio}-1-methyl-1-carbapen-2-em-3-carboxylate A solution of 50 mg of 4-nitrobenzyl (1R,5S,6S)-2-(4-chlorophenyl)sulfinyl-6-[(1R)-1-hydroxyethyl]-1-methyl-1-carbapen-2-em-3-carboxylate and 19.4 mg of diisopropylethylamine in 0.5 ml of anhydrous acetonitrile was added dropwise to a solution of 93 mg of (2S,4S)-{4-[2-(4-nitrobenzyloxycarbonyl)oxyethyl]-1-piperazinylcarbonyl}-4-mercapto -1-(4-nitrobenzyloxycarbonyl)pyrrolidine in 0.5 ml of anhydrous acetonitrile, whilst ice-cooling, and the resulting mixture was stirred at the same temperature for 1 hour. At the end of this time, the solvent was removed by distillation under reduced pressure, and the resulting residue was treated by the same procedure as described in the step (1), above, to afford 13 mg of the title compound as a powder. The spectral data (infra-red absorption spectrum and nuclear magnetic resonance spectrum) of the product were completely identical with those of the compound obtained as described in Example 21(2).

EXAMPLE 24

(1R, 5S, 6S)-2-{(2S,4S)-2-[4-(2-Hydroxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride A solution of 1.0 g of 4-nitrobenzyl (1R,5S,6S)-2[(2S,4)-2-(4-methyl-1-piperazinylcarbonyl)-1-(4-nitrobenzyloxycarbonyl)pyrrolidin-4-ylthio]-6-[(1R)-1-hydroxyethyl]-1methyl-1-carbapen-2-em-3-carboxylate dissolved in 5 ml of 2-iodoethanol was stirred at 50° C. for 10 hours. At the end of this time, the reaction mixture was poured into 50 ml of diethyl ether, and the precipitate which deposited was collected by filtration and then washed three times, each time with 50 ml of diethyl ether, after which it was dried. The powder (1.28 g) thus obtained was dissolved in 50 ml of a 1:1 by volume mixture of tetrahydrofuran and water and was hydrogenated at room temperature for 2 hours in the presence of 1.0 g of a 10% w/w palladium-on-carbon catalyst. At the end of this time, the catalyst was removed by filtration. The reaction mixture was then extracted twice, each time with 50 ml of diethyl ether, and the aqueous layer was concentrated by evaporation under reduced pressure to a volume of 10 ml. The concentrate was then subjected to column chromatography through 100 ml of an ion exchange resin (Dowex 1 - x4, 50–100 mesh, cl − type). Those fractions containing the desired compound were collected and concentrated by evaporation under reduced pressure, to a volume of 20 ml. The concentrate was purified by chromatography through a reverse phase column (LiChroprep RP-8), using 2% by volume aqueous methanol as the eluent. Those fractions containing the desired compound were collected and concentrated by evaporation under reduced pressure, to afford 290 mg of the desired compound as a colorless powder. The infra-red and ultra-violet absorption spectra and nuclear magnetic resonance spectrum of the product were completely identical with those of the compound obtained as described in Example 20.

EXAMPLE 25

(1R,5S,6S)-2-{(2S,4S)-2-[4-(2-Hydroxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride 45 μl of methyl trifluoromethanesulfonate were added dropwise to a solution of 320 mg of (2S,4S)-4-mercapto-2-{4-[2-(p-nitrobenzyloxycarbonyl) oxyethyl]-1-piperazinylcarbonyl}1-(p-nitrobenzyloxycarbonyl)pyrrolidine [prepared as described in Example 23(2)] dissolved in 3.2 ml of anhydrous acetonitrile, whilst ice-cooling, and the resulting mixture was stirred for 1 hour. At the end of this time, the solvent was removed by distillation under reduced pressure, and the residue thus obtained was hydrogenated using the same procedure as described in Example 21(3). The crude product thus obtained was then purified by column chromatography using an ion exchange resin and reverse phase chromatography to afford 80 mg of the title compound as a colorless powder. The spectral data (infra-red and ultra-violet absorption spectra and nuclear magnetic resonance spectrum) of the product were identical with those of the compound obtained as described in in Example 20.

EXAMPLE 26

(1R,5S,6)-2-{(2S,4S)-2-[4-(2-Hydroxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride 31 μl of dimethyl sulfate were added dropwise to a solution of 289 mg of (2S,4S)-4-mercapto-2-{4-[2-(p-nitrobenzyloxycarbonyl)oxyethyl]-1-piperazinylcarbonyl}-1-(p-nitrobenzyloxycarbonyl) pyrrolidine [prepared as described in Example 21(2)] in 3 ml of acetone, whilst ice-cooling, and the resulting mixture was stirred at room temperature for 1 hour. At the end of this time, the solvent was removed by distillation under reduced pressure, and the resulting residue was hydrogenated using the same procedure as described in Example 21(3). The crude product thus obtained was purified by column chromatography using anion exchange resin and reverse phase chromatography to afford 45 mg of the title compound as a colorless powder.

The spectral data (infra-red and ultra-violet absorption spectra and nuclear magnetic resonance spectrum) of the product were identical with those of the compound obtained as described in Example 20.

EXAMPLE 27

(1R,5S,6S)-2-{(2S,4S)-2-[4-(2-Hydroxyethyl)-4-methyl-1-piperaziniocarbonyl]pyrrolidin-4-ylthio}-6-[(1R)-1-hydroxyethyl]-1-methyl-1-carbapen-2-em-3carboxylate hydrochloride A mixture of 300 mg of (2S,4S)-4-mercapto-2-{4-[2-(p-nitrobenzyloxycarbonyl)oxyethyl]-1-piperazinylcarbonyl}-1-(p-nitrobenzyloxycarbonyl)pyrrolidine [prepared as described in Example 21(2)] and 2 ml of methyl iodide was heated at 50° C. in a sealed tube for 6 hours. 30 ml of diethyl ether were added to the reaction mixture, and the resulting precipitate was collected by filtration, washed three times, each time with 20 ml of diethyl ether, and then dried. The resulting precipitate was then hydrogenated using the same procedure as described in Example 21(3). The crude product thus obtained was purified by column chromatography using an ion exchange resin and reverse phase chromatography to afford 83 mg of the title compound as a colorless powder. The spectral data (infra-red and ultra-violet absorption spectra and nuclear magnetic resonance spectrum) of the product were identical with those of the compound obtained as described in Example 20.

EXAMPLE 28

(1R,5S,6)-2-{(2S,4S)-2-[4-(2-Hydroxyethyl)-4methyl-1-piperaziniocarbonyl]pyrrolidin-4-ylthio}-6-[(1R)-1-hydroxyethyl]-1-methyl-1-carbapen-2-em-3-carboxylate hemisulfate 115 mg of (1R,5S,6S)-2-{(2S,4S)-2-[4-(2-hydroxyethyl)-4-methyl-1-piperaziniocarbonyl]pyrrolidin-4-ylthio}-6-[(1R)-1-hydroxyethyl]-1-methyl-1-carbapen-2-em-3-carboxylate hydrochloride (prepared, for example, as described in Example 30) were dissolved in 2 ml of water, and the solution was subjected to column chromatography through 10 ml of an ion exchange resin (Dowex 1 -x4, 50–100 mesh, $SO_4^{2-}$ type) using water as the eluent. Those fractions containing the title compound were collected and concentrated by evaporation under reduced pressure. The concentrate was then lyophilized, to afford 103 mg of the title compound as a powder.

Ultraviolet Absorption Spectrum ($H_2O$). $\lambda_{max}$ nm: 296.

Infrared Absorption Spectrum (KBr), $\nu_{max}$ cm$^{-1}$; 1756, 1659, 1598, 1464, 1384.

Nuclear Magnetic Resonance Spectrum ($D_2O$, 270 MHz, internal standard: sodium trimethylsilylpropionate-d4) δ ppm:
1.21 (3H, doublet, J=7.3 Hz);
1.29 (3, doublet, J=6.3 Hz);
1.95–2.05 (1H, multiplet);
3.01–3.12 (1H, multiplet);
3.32 and 3.33 (together 3H, two singlets;
3.34–3.59 (3H, multiplet);
3.59–4.30 (16H, multiplet);
4.80–4.90 (1H, multiplet).

EXAMPLE 29

(5R,6S)-2-{(2S,4S)-2-[4-(2-Hydroxyethyl)-4-methyl-1-piperaziniocarbonyl]pyrrolidin-4-ylthio}-6-[(1R)-1-hydroxyethyl]-1-carbapen-2-em-3-carboxylate hydrochloride 29(1) 4-Nitrobenzyl (5R,6S)-2-{(2S,4S)-[4-(2-p'-nitrobenzyloxycarbonyloxyethyl)-1-piperazinylcarbonyl]-1-(4-nitrobenzyloxcarbonyl)pyrrolidin-4-ylthio}-6-[(1R)-1-hydroxyethyl]-1-carbapen-2-em-3-carboxylate 115 μl of diisopropylethylamine and 116 μof diphenyl chlorophosphate were simultaneously added to a solution of 218 mg of 4-nitrobenzyl (5R,6S-6-[(1R)-1-hydroxyethyl]-2-oxo-1carbapenam-3-carboxylate in 3 ml of anhydrous acetonitrile, whilst ice-cooling, and the resulting mixture was stirred at the same temperature for 1 hour. A solution of 109 μl of diisopropylethylamine and 387 mg of (2S,4S)-4-mercapto-2-{4-[2-(p-nitrobenzyloxycarbonyl)oxyethyl]-1-piperazinylcarbonyl}-1-(p-nitrobenzyloxycarbonyl)pyrrolidine [prepared as described in Example 23(1) ] in anhydrous acetonitrile (2 ml) was then added, whilst ice-cooling, to the reaction mixture, and the resulting mixture was stirred at the same temperature for 2 hours, after which it was allowed to stand overnight, whilst ice-cooling. At the end of this time, the solvent was removed by distillation under reduced pressure, and the resulting residue was mixed with an aqueous solution of sodium chloride and extracted with ethyl acetate. The extract was washed with an aqueous solution of sodium hydrogen-carbonate and with an aqueous solution of sodium chloride, in that order, and dried over anhydrous magnesium sulfate. The solvent was again removed by distillation under reduced pressure, and the resulting residue was subjected to column chromatography through silica gel using a 50:4 by volume mixture of methylene chloride and methanol as the eluent. The combined fractions containing the title compound were then concentrated by evaporation under reduced pressure, to afford 493 mg of the title compound as a powder.

Infrared Absorption Spectrum (KBr), $\nu_{max}$ cm$^{-1}$: 1777, 1749, 1708, 1653, 1607, 1521, 14g8, 1404.

Nuclear Magnetic Resonance Spectrum ($CDCl_3$, 270 MHz), δ ppm:
1.36 (3H, doublet, J=6.35 Hz);
1.83–2.05 (2H, multiplet);
2.29–2.95 (5H, multiplet);
3.06–3.78 (8H, multiplet);
4.17–4.52 (4H, multiplet);

4.63-4.77 (1H, multiplet);
5.04-5.51 (6H, multiplet);
7.44 and 7.50 (together 2H, each doublet, J=8.30 Hz);
7.55 (2H, doublet, J=8.79 Hz);
7.64 (2H, doublet, J=8.79 Hz);
8.17-8.25 (6H, multiplet).

29(2)
(5R,6S)-2{(2,S,4S)-2-[4-(2-Hydroxyethyl)-4-methyl-1-piperaziniocarbonyl]pyrrolidin-4-ylthio}-6-[(1R)-1-hydroxyethyl]-1-carbapen-2-em-3-carboxylate hydrochloride 49 μl of methyl fluorosulfonate were added to a solution of 493 mg of 4-nitrobenzyl (5R, 6S)-2-{(2S,4S)-[4-(2-p'-nitrobenzyloxycarbonyloxyethyl)-1-piperazinylcarbonyl]-1-(4-nitrobenzyloxycarbonyl)pyrrolidin-4-ylthio}-6-[(1R)-1-hydroxyethyl]-1-carbapen-2-em-3-carboxylate [prepared as described in step (1) above] in 5 ml of anhydrous acetonitrile, whilst ice-cooling, after which the mixture was stirred at the same temperature for 30 minutes. At the end of this time, the solvent was removed by distillation under reduced pressure, and the resulting residue was dissolved in a mixture of 15 ml of tetrahydrofuran and 15 ml of water and hydrogenated at room temperature in the presence of 500 mg of a 10% w/w palladium-on-carbon catalyst for 75 minutes. At the end of this time, the catalyst was removed by filtration. The filtrate was washed with diethyl ether, and the aqueous layer was concentrated by evaporation under reduced pressure. The concentrate was subjected to column chromatography through 50 ml of an ion exchange resin (Dowex 1 -x4, 50-100 mesh, Cl− type) using water as the eluent. Those fractions containing the title compound were collected and lyophilized. The resulting powder was then subjected to column chromatography through a Lobar column (RP-8, size B) using water as the eluent. Those fractions containing the title compound were collected and lyophilized to afford 112 mg of the title compound as a colorless powder.

Infrared Absorption Spectrum (KBr), $\nu_{max}$ cm$^{-1}$: 1764, 1660, 1593, 1467, 1378, 1259.

Ultraviolet Absorption Spectrum (H$_2$O), $\lambda_{max}$ nm: 297.

Nuclear magnetic Resonance Spectrum (D$_2$O, 270 MHz, internal standard: sodium trimethylsilylpropionate-d4) δ ppm: 1.29 (3H, doublet, J=6.34 Hz);
1.98-2.11 (1H, multiplet);
2.95-3.14 (1H, multiplet);
3.15-3.27 (2H, multiplet);
3.32 (3H, singlet);
3.40-3.55 (2H, multiplet);
3.56-3.80 (6H, multiplet); 3.81-4.30 (10H, multiplet);
4.81-4.93 (1H, multiplet).

EXAMPLE 30
(1R,5S,6S)-2[(2S,4S)-2-(4,4-Dimethyl-1-homopiperaziniocarbonyl)pyrrolidin-4-ylthio]-6-[(1R)-1-hydroxyethyl]-1-methyl-1-carbapen-2-em-3-carboxylate hemisulfate 26 mg of (1R,5S,6S)-2-[(2S,4S)-2-(4,4-dimethyl-1-homopiperaziniocarbonyl) pyrrolidin-4-ylthio]-6-[(1R)-1-hydroxyethyl]-1-methyl-1-carbapen-2-em-3-carboxylate hydrochloride [prepared as described in Example 7(3)] were subjected to column chromatography through 25 ml of an ion exchange resin (Dowex 2 -x4, 50-100 mesh, SO$_4^{2-}$ type) using water as the eluent. Those fractions containing the title compound were collected and concentrated by evaporation under reduced pressure. The residue was then subjected to column chromatography through a Lobar column (a product of Merck & Co., Inc., LiChroprep RP-8, size B) using 5% by volume aqueous methanol. Those fractions containing the title compound were collected and lyophilized to afford 14 mg of the title compound as a powder.

Nuclear Magnetic Resonance Spectrum (D$_2$O, 270 MHz), δ ppm:
1.02 (3H, doublet, J=7.32 Hz);
1.10 (3H, doublet, J=6.35 Hz);
1.70-1.89 (1H, multiplet);
2.13 (2H, broad singlet);
2.73-2.95 (1H, multiplet);
3.02 and 3.03 (together 6H, two singlets);
3.04-3.32 (3H, multiplet);
3.41-3.89 (10H, multiplet);
4.02-4.08 (2H, multiplet);
4.62-4.68 (1H, multiplet).

EXAMPLE 31
(1R,5S,6S)-2-[(2S,4S)-2-(4,4-Dimethyl-1-homopiperaziniocarbonyl)pyrrolidin-4-ylthio]-6-[(1R)-1-hydroxyethyl]-1-methyl-1-carbapen-2-em-3-carboxylate hydrochloride.

25 mg of (1R,5S,6S)-2-[(2S,4S)-2-(4,4-dimethyl-1-homopiperaziniocarbonyl) pyrrolidin-4-ylthio]-6-[(1R)-1-hydroxyethyl]-1-methyl-1-carbapen-2-em-3-carboxylate hydrochloride [prepared as described in Example 7(3)] were subjected to column chromatography through 25 ml of an ion exchange resin (Dowex 1 -x4, 50-100 mesh, Cl− type) using water as the eluent. Those fractions containing the title compound were worked-up, purified and lyophilized in a similar manner to that described in Example 30, to afford 13 mg of the title compound as a powder.

Nuclear Magnetic Resonance Spectrum (D$_2$O, 270 MHz), δ ppm:
1.02 (3H, doublet, J=7.3 Hz);
1.10 (3H, doublet, J=6.3 Hz);
1.72-1.89 (1H, multiplet);
2.15 (2H, broad singlet);
2.75-2.94 (1H, multiplet);
3.02 and 3.03 (together 6H, two singlets);
3.11-3.25 (1H, multiplet);
3.26-3.34 (2H, multiplet);
3.41-3.92 (10H, multiplet);
4.02-4.11 (2H, multiplet);
4.63-4.69 (1H, multiplet).

EXAMPLE 32
(1R,5S,6S)-2-{(2S,4S)-4-(2-Hydroxyethyl)-4-methyl-1-homopiperaziniocarbonyl]pyrrolidin-4-ylthio}-6-[(R)-1-hydroxyethyl]-1-methyl-1-carbapen-2-em-3-carboxylate hydrochloride 32(1(2S,4S)-4-mercapto-2-{4-[2-(4-nitrobenzyloxycarbonyl)oxyethyl]-1-homopiperazinylcarbonyl}-1-(4-nitrobenzyloxycarbonyl)pyrrolidine trifluoromethansulfonate 5 ml of trifluoroacetic acid and 110 μl of trifluoromethanesulfonic acid were added, whilst ice-cooling, to a solution of 900 mg of (2S,4S)-4-(4-methoxybenzylthio)-2-{4-[2-(4-nitrobenzyloxycarbonyl)oxyethyl]-1-homopiperazinylcarbonyl}-1-(4-nitrobenzyloxycarbonyl)pyrrolidine dissolved in 1 ml of anisole, and the resulting mixture was stirred under the same conditions for 1 hour. At the end of this time, the solvent was removed by distillation under reduced pressure, and the resulting residue was washed with diethyl ether, to afford 750 mg of the title compound as a colorless powder.

32(2) 4-Nitrobenzyl (1R,5S,6S)-2-{(2S,4S)-2-[4-(2-p'-nitrobenzyloxycarbonyloxyethyl)-1-homopiperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 230 μl of diphenyl chlorophosphate and 200 μl of diisopropylethylamine were added dropwise, whilst ice-cooling, to a solution of 400 mg of 4-nitrobenzyl (1R,5R,6S)-6-[(1R)-1-hydroxyethyl]-1-methyl-2-oxo-1-carbapenam-3-carboxylate dissolved in 4 ml of anhydrous acetonitrile, and the resulting mixture was stirred at the same temperature for 30 minutes. A solution of 710 mg of (2S,4S)-4-mercapto-2-{4-[2-(4-nitrobenzyloxycarbonyl)oxyethyl]-1-homopiperazinylcarbonyl}-1-(4-nitrobenzyloxycarbonyl)pyrrolidine trifluoromethanesulfonate [prepared as described in step (1) above] in 3 ml of acetonitrile and 600 μl of diisopropylethylamine were then added dropwise, whilst ice-cooling, to the mixture, and the resulting mixture was then stirred at the same temperature for 4 hours, after which it was allowed to stand overnight at 4° C. The reaction mixture was then diluted with 200 ml of ethyl acetate and washed with 200 ml of water and with 200 ml of an aqueous solution of sodium chloride, in that order. The organic layer was then dried over anhydrous sodium sulfate and concentrated by evaporation under reduced pressure. The resulting residue was subjected to column chromatography through silica gel, using mixtures of ethyl acetate and methanol ranging from 9:1 to 8:2 by volume as the eluent. Those fractions containing the title compound were collected and concentrated by evaporation under reduced pressure, to afford 640 mg of the title compound as a powder.

Infrared Absorption Spectrum (KBr), $v_{max}$ cm$^{-1}$: 1768, 1750, 1710, 1649, 1522, 1347, 1260.

Nuclear Magnetic Resonance Spectrum (CDCl$_3$, 270 MHz), δ ppm:

1.27 (3H, doublet, J=7.3 Hz);
1.36 (3H, doublet, J=6.0 Hz);
1.80–2.05 (3H, multiplet);
2.40–3.00 (7H, multiplet);
3.23–3.78 (7H, multiplet);
4.00–4.29 (5H, multiplet);
4.61–4.77 (1H, multiplet);
5.03–5.53 (6H, multiplet);
7.42–7.67 (6H, multiplet);
8.16–8.25 (6H, multiplet).

32(3) (1R,5S,6S)-2-{(2S,4S)-2-[4-(2-Hydroxyethyl)-4-methyl-1-homopiperaziniocarbonyl]pyrrolidin-4-ylthio}-6-[(1R)-1-hydroxyethyl]-1-methyl-1-carbapen -b 2-em-3-carboxylate hydrochloride 80 μl of methyl trifluoromethanesulfonate were added dropwise, whilst ice-cooling, to a solution of 640 mg of 4-nitrobenzyl (1R,5S,6S)-2-{(2S,4S)-2-[4(2-p'-nitrobenzyloxycarbonyl)-1-homopiperazinylcarbonyl]1-(4-nitrobenzyloxycarbonyl)pyyrolidin-4-ylthio}-6-[(1R)-1-hydroxyethyl]-1-methyl-1-carbapen-2-em-3-carboxylate [prepared as described in step (2) above] in 10 ml of acetonitrile, and the resulting mixture was stirred for 1 hour. At the end of this time, the reaction mixture was concentrated by evaporation under reduced pressure, to afford a powdery compound, which was dissolved in 20 ml of a 1:1 by volume mixture of tetrahydrofuran and water and hydrogenated at room temperature in the presence of 1 g of a 10% w/w palladium-on-carbon catalyst for 1 hour. The catalyst was removed by filtration, and then the filtrate was extracted twice with diethyl ether. The aqueous layer was concentrated by evaporation under reduced pressure, and the concentrate was subjected to column chromatography through an ion exchange resin (Dowex 1 -x4, 50–100 mesh, Cl$^-$ type) using water as the eluent. Those fractions containing the title compound were collected and concentrated by evaporation under reduced pressure. The concentrate was then subjected to column chromatography through a reverse phase column (LiChroprep RP-8, size B) using 2% by volume aqueous methanol as the eluent. Those fractions containing the title compound were collected and concentrated by evaporation under reduced pressure, followed by lyophilization, to afford 139 mg of the title compound as a colorless powder.

Infrared Absorption Spectrum (KBr), $v_{max}$ cm$^{-1}$: 1768, 1707, 1638, 1521, 1345, 1209, 1136.

Ultraviolet Absorption Spectrum (H$_2$O), $\lambda_{max}$ nm: 297.

Nuclear Magnetic Resonance Spectrum (D$_2$O, 270 MHz, internal standard: sodium trimethylsilylpropionate-d4) δ ppm:

1.21 (3H, doublet, J=6.9 Hz);
1.28 (3H, doublet, J=6.3 Hz);
1.95–2.08 (1H, multiplet);
2.34 (2H, broad singlet);
3.03–3.14 (1H, multiplet);
3.24 (3H, singlet);
3.31–3.43 (1H, multiplet);
3.44–3.53 (3H, multiplet);
3.55–4.16 (13H, multiplet);
4.20–4.29 (2H, multiplet);
4.83–4.92 (1H, multiplet).

EXAMPLE 33

(1R,5S,6S)-6-[(1R)-1-Hydroxyethyl]-1-methyl-2-{(2S,4S)-2-[4-(1-Sulfopropyl-3-yl)-4-methyl-1-piperaziniocarbonyl]pyrrolidin-4-ylthio}-1-carbapen -2-em-3-carboxylate 130 mg of propane sultone were added to a solution of 753 mg of 4-nitrobenzyl (1R,5S,6S)-6[(1R)-1-hydroxyethyl]-1-methyl-2-[(2S,4S)-2-(4-methyl-1-piperazinylcarbonyl)-1-(4-nitrobenzyloxycarbonyl)pyrrolidin-4-ylthio ]-1-carbapen-2-em-3-carboxylate [prepared as described in Example 1(2)] in 10 ml of acetonitrile, and the resulting mixture was stirred at room temperature for 60 hours and then at 50° C. for 22 hours. At the end of this time, the solvent was removed by distillation under reduced pressure, and the resulting residue was dissolved in 30 ml of a 1:1 by volume mixture of tetrahydrofuran and water and hydrogenated at room temperature in the presence of 800 mg of a 10 % w/w palladium-on-carbon catalyst for 2.5 hours. The catalyst was removed by filtration, and then the filtrate was extracted twice with diethyl ether. The aqueous layer was then concentrated by evaporation under reduced pressure to a volume of 5 ml, and the concentrate was subjected to column chromatography through a reverse phase column (LiChroprep RP-8, size B) using water as the eluent. Those fractions containing the title compound were collected, concentrated by evaporation under reduced pressure and lyophilized, to afford 137 mg of the title compound as a powder.

Infrared Absorption Spectrum (KBr), $\nu_{max}$ cm$^{-1}$: 1759, 1659, 1597, 1470, 1387, 1184, 1041.

Ultraviolet Absorption Spectrum (H$_2$O). $\lambda_{max}$ nm: 297.

Nuclear Magnetic Resonance Spectrum (D$_2$O, 270 MHz, internal standard: sodium trimethylsilylpropionate-d4) δ ppm:
1.22 (3H, doublet, J=7.3 Hz);
1.29 (3H, doublet, J=6.6 Hz);
1.93–2.11 (1H, multiplet);
2.24–2.36 (1H, multiplet);
2.94–3.14 (411, multiplet);
3.26 and 3.27 (together 3H, two singlets);
3.32–3.57 (3H, multiplet);
3.64–4.30 (17H, multiplet);
4.80–4.90 (1H, multiplet).

EXAMPLE 34

(5R,6S)-2-[(2S,4S)-2-(4,4-Dimethyl-1-piperaziniocarbonyl)pyrrolidin-4-ylthio]-6-[(1R)-1-hydroxyethyl]-1-carbapen-2-em-3-carboxylate hydrochloride

34(1) 4-Nitrobenzyl (5R,6S)-6-[(1R)-1-hydroxyethyl]-2-[(2S,4S)-2-(4-methyl-1-piperazinylcarbonyl)-1-(4-nitrobenzyloxycarbonyl)pyrrolidin-4-ylthio]-1-carbapen-2-em-3-carboxylate 85 μl of diisopropylethylamine and 86 μl of diphenyl chlorophosphate were simultaneously added, whilst ice-cooling, to a solution of 161 mg of 4-nitrobenzyl (5R,6S)-6-[(1R)-1-hydroxyethyl]-2-oxo-1-carbapenam-3-carboxylate in 2 ml of anhydrous acetonitrile, and the resulting mixture was stirred at the same temperature for 1 hour. At the end of this time, 232 μof diisopropylethylamine and a solution of 310 mg of (2S,4S)-4-mercapto-2-(4-methyl-1-piperazinylcarbonyl)-1-(4-nitrobenzyloxycarbonyl)pyrrolidine trifluoromethanesulfonate [prepared as described in Example 1(1)] in 2 ml of anhydrous acetonitrile were added dropwise to the mixture, whilst ice-cooling, and the resulting mixture was stirred at the same temperature for 2 hours, after which it was allowed to stand overnight, whilst ice-cooling. At the end of this time, the solvent was removed by distillation under reduced pressure, and the resulting residue was worked up and purified in a similar manner to that described in Example 29(1), to afford 209 mg of the title compound as a powder.

34(2) (5R,6S)-2-[(2S,4S)-2-(4,4-Dimethyl-1-piperaziniocarbonyl)pyrrolidin-4-ylthio]-6-[(1R)-1-hydroxyethyl]-1-carbapen-2-em-3-carboxylate hydrochloride 27 μl of methyl fluorosulfonate were added to a solution of 205 mg of 4-nitrobenzyl (4R,6S)-6-[(1R)-1-hydroxyethyl]-2-[(2S,4S)-2-(4-methyl-1-piperazinylcarbonyl)-1-(4-nitrobenzyloxycarbonyl pyrrolidin-4-ylthio]-1-carbapen-2-em-3-carboxylate [prepared as described in step (1) above] in 2.1 ml of anhydrous acetonitrile, whilst ice-cooling, and the resulting mixture was stirred at the same temperature for 30 minutes. At the end of this time, the solvent was removed by distillation under reduced pressure, and the resulting residue was dissolved in a mixture of 7 ml of tetrahydrofuran and 7 ml of water and hydrogenated in the presence of 250 mg of a 10% w/w palladium-on-carbon catalyst. The reaction mixture was then worked up and purified in a similar manner to that described in Example 29(2), to afford 21 mg of the title compound as a powder.

Ultraviolet Absorption Spectrum (H$_2$O). $\lambda_{max}$ nm: 297.

EXAMPLE 35

(5R,6S)-2[(2S,4S)-2-(4,4-Dimethyl-1-homopiperaziniocarbonyl)pyrrolidin-4-ylthio]-6-[(1R)-1-hydroxyethyl]-1-carbapen-2-em-3-carboxylate hydrochloride

35(1) 4-Nitrobenzyl (5R,6S)-2-[(2S,4S)-2-(4-methyl-1-homopiperazinylcarbonyl)-1-(4-nitrobenzyloxycarbonyl)pyrrolidin-4-ylthio]-6-[(1R)-1-hydroxyethyl]-1-carbapen-2-em-3-carboxylate 76 μl of diisopropylethylamine and 77 μl of diphenyl chlorophosphate were simultaneously added, whilst ice-cooling, to a solution of 145 mg of 4-nitrobenzyl (5R,6S)-6-[(1R)-1hydroxyethyl]-2-oxo-1-carbapenam-3-carboxylate in 2 ml of anhydrous acetonitrile, and the resulting mixture was stirred at the same temperature for 1 hour. 247 μl of diisopropylamine and a solution of 361 mg of (2S,4S)-4-mercapto-2-(4-methyl-1-homopiperazinylcarbonyl)-1-(4-nitrobenzyloxycarbonyl)pyrrolidine bis(trifluoromethanesulfonate) [prepared as described in Example 7(1)] in 2 ml of anhydrous acetonitrile were added dropwise to the mixture, whilst ice-cooling, and the resulting mixture was stirred at the same temperature for 2 hours, after which is was allowed to stand overnight, whilst ice-cooling. At the end of this time, the solvent was removed by distillation under reduced pressure, and the resulting residue was worked up and purified in a similar manner to that described in Example 29(1), to afford 150 mg of the title compound as a powder.

35(2) (5R,6S)-2-[(2S,4S)-2-(4-Dimethyl-1-homopiperaziniocarbonyl)pyrrolidin-4-ylthio]-6-[(1R)-1-hydroxyethyl]-1-carbapen-2-em-3-carboxylate hydrochloride 18 μof methyl fluorosulfonate were added, whilst ice-cooling, to a solution of 141 mg of 4-nitrobenzyl (5R,6S)-2-[(2S,4S)-2(4-methyl-1-homopiperazinylcarbonyl)-1-(4-nitrobenzyloxycarbonyl)pyrrolidin-4-ylthio]-6-[(1R)-1-hydroxyethyl]-1-carbapen-2-em-3-carboxylate [prepared as described in step (1) above] in 1.5 ml of anhydrous acetonitrile, and the resulting mixture was stirred at the same temperature for 30 minutes. At the end of this time, the solvent was removed by distillation under reduced pressure, and the resulting residue was dissolved in a mixture of 5 ml of tetrahydrofuran and 5 ml of water and hydrogenated in the presence of 170 mg of a 10% w/w palladium-on-carbon catalyst. The reaction mixture was then worked up and purified in a similar manner to that described in Example 29(2), to afford 17 mg of the title compound as a powder.

Ultraviolet Absorption Spectrum (H$_2$O, $\lambda_{max}$ nm: 297.

EXAMPLE 36

(1R,5S,6S)-2-{(2S,4S)-2-[4-(2-Carbamoyloxyethyl)-4-methyl-1-homopiperaziniocarbonyl]pyrrolidin-4-ylthio}-6-[(1R)-1-hydroxyethyl]-1-methyl-1-carbapen-2-em-3-carboxylate hydrochloride

36(1)
(2S,4S)-2-[4-(2-Carbamoyloxyethyl)-1-homopiperazinylcarbonyl]4-mercapto-1-(4-nitrobenzyloxycarbonyl)pyrrolidine trifluoromethanesulfonate 2.7 ml of trifluoroacetic acid and 88 μl of trifluoromethanesulfonic acid were added, whilst ice-cooling, to a solution of 308 mg of (2S,4S)-4-(4-methoxybenzylthio)-2-[4-(2-carbamoyloxyethyl)-1-homopiperazinylcarbonyl]-1-(4-nitrobenzyloxycarbonyl)pyrrolidine dissolved in 543 μl of anisole, and the resulting mixture was stirred a the same temperature for 1 hour. At the end of this time, the reaction mixture was worked up in a similar manner to that described in Example 32(1), to afford 315 mg of the title compound.

36(2) 4-Nitrobenzyl
(1R,5S,6S)-2-{(2S,4S)-2-[4-(2-carbamoyloxyethyl)-1-homopiperazinylcarbonyl]-1-(4-nitrobenzyloxycarbonyl)pyrrolidin-4-ylthio}-6-[(1R)-1-hydroxyethyl]-1-methyl-1-carbapen-2-em-3-carboxylate 88 μl of diphenyl chlorophosphate and 74 μl of diisopropylethylamine were added dropwise, whilst ice-cooling, to a solution of 145 mg of 4-nitrobenzyl (1R,5R,6S)-6-[(1R)-1-hydroxyethyl]-1-methyl-2-oxo-1-carbapenam-3-carboxylate in 2 ml of anhydrous acetonitrile, and the resulting mixture was stirred at the same temperature for 1 hour. 202 μl of diisopropylethylamine and a solution of 310 mg of (2S,4S)-2-[4-(2-carbamoyloxyethyl)-1-homopiperazinylcarbonyl]-4-mercapto-1-(4-nitrobenzyloxycarbonyl)pyrrolidine trifluoromethanesulfonate [prepared as described in step (1) above] in 2.0 ml of anhydrous acetonitrile were then added dropwise to the mixture, whilst ice-cooling, and the resulting mixture was allowed to stand overnight at the same temperature. At the end of this time, the reaction mixture was worked up and purified in a similar manner to that described in Example 32(2), to afford 107 mg of the title compound as a powder.

36(3)
(1R,5S,6S)-2-{(2S,4S)-2-[4-(2-Carbamoyloxyethyl)-4-methyl-1-homopiperaziniocarbonyl]pyrrolidin-4-ylthio}-6-[(1R)-1-hydroxyethyl]-1-methyl-1-carbapen-2-em-3-carboxylate hydrochloride 14 μl of methyl fluorosulfonate were added dropwise to a solution of 105 mg of a 4-nitrobenzyl (1R,5S,6S)-2-{(2S,4S)-2-[4-(2-carbamoyloxyethyl)-1-homopiperazinylcarbonyl-1-(4-nitrobenzyloxycarbonyl)pyrrolidin-4-ylthio}-6-[(1R)-1-hydroxyethyl]-1-methyl-1-carbapen-2-em-3-carboxylate [prepared as described in step (2) above] in 2.2 ml of anhydrous acetonitrile, whilst ice-cooling, and the resulting mixture was then stirred for 1 hour. At the end of this time, the solvent was removed by distillation under reduced pressure, and the resulting residue was dissolved in a mixture of 5.5 ml) tetrahydrofuran and 5.5 ml of water and hydrogenated in the presence of 225 mg of a 10% w/w palladium-on-carbon catalyst. The reaction mixture was then worked up and purified in a similar manner to that described in Example 32(3), to afford 31 mg of the title compound as a powder.

Ultraviolet Absorption Spectrum (H₂O), $\lambda_{max}$ nm:

EXAMPLE 37

(1R,5S,6S)-2-[(2S,4S)-2-(4-Carbamoylmethyl-4-methyl-1-homopiperaziniocarbonyl)pyrrolidin-4-ylthio]-6-[(1R)-1-hydroxyethyl]-1-methyl-1-carbapen-2-em-3-carboxylate hydrochloride

37(1)
(2S,4S)-2-(4-Carbamoylmethyl-1-homopiperazinyl)-4-mercapto-1-(4-nitrobenzyloxycarbonyl)pyrrolidine trifluoromethanesulfonate 3.4 ml of trifluoroacetic acid and 110 μl of trifluoromethanesulfonic acid were added, whilst ice-cooling, to a suspension of 366 mg of (2S,4S)-4-(4-methoxybenzylthio)--2-(4-carbamoylmethyl-1-homopiperazinylcarbonyl)-1-(4-nitrobenzyloxycarbonyl)pyrrolidine in 679 μl of anisole, and the resulting mixture was stirred at room temperature for 1 hour. At the end of this time, the reaction mixture was worked up in a similar manner to that described in Example 32(1), to afford 355 mg of the title compound.

37(2) 4-Nitrobenzyl
(1R,5S,6S)-2-[(2S,4S)-2-(4-ylthio]-6-[(1R)-1-hydroxyethyl]-1-methyl-1-carbapen-2-em-3-carboxylate 104 μl of diphenyl chlorophosphate and 88 μl of diisopropylethylamine were added dropwise, whilst ice-cooling, to a solution of 171 mg of 4-nitrobenzyl (1R,5R,6S)-6-[(1R)-1-hydroxyethyl]-1-methyl-2-oxo-1-carbapenam-3-carboxylate in 2 ml of anhydrous acetonitrile, and the resulting mixture was stirred at the same temperature for 1 hour. 237 μl of diisopropylethylamine and a solution of 350 mg of (2S,4S)-2-(4-carbamoylmethyl-1-homopiperazinyl)-4-mercapto-1-(4-nitrobenzyloxycarbonyl)pyrrolidine trifluoromethanesulfonate [prepared as described in step (1) above] in 2 ml of anhydrous acetonitrile were then added to the mixture, whilst ice-cooling, and the mixture was allowed to stand overnight at the same temperature. At the end of this time, the reaction mixture was worked up and purified in a similar manner to that described in Example 32(2), to afford 143 mg of the title compound as a powder.

37(3)
(1R,5S,6S)-2-[(2S,4S)-2-(4-Carbamoylmethyl-4-methyl-1-homopiperaziniocarbonyl)pyrrolidin-4-ylthio]-6-[(1R)-1-hydroxyethyl]-1-methyl-1-carbapen-2-em-3-carboxylate hydrochloride 15.5 μl of methyl fluorosulfonate were added dropwise to a solution of 131 mg of 4-nitrobenzyl (1R,5S,6S)-2-[(2S,4S)-2-(4-carbamoylmethyl-1-homopiperazinylcarbonyl)pyrrolidin-4-ylthio]-6-[(1R)-1-hydroxyethyl]-1-methyl-1-carbapen-2-em-3-carboxylate [prepared as described in step (2) above] in 2.4 ml of anhydrous acetonitrile, whilst ice-cooling, and the resulting mixture was stirred for 1 hour. At the end of this time, the solvent was removed by distillation under reduced pressure, and the resulting residue was dissolved in a mixture of 6 ml of tetrahydrofuran and 6 ml of water and hydrogenated in the presence of 240 mg of a 10% w/w palladium-on-carbon catalyst. The reaction mixture was then worked up and purified in a similar manner to that described in Example 32(3), to afford 28 mg of the title compound as a powder.

Ultraviolet Absorption Spectrum (H$_2$O), $\lambda_{max}$ nm: 297.5.

PREPARATION 1

(2S,4S)-4-(4-Methoxybenzylthio)-2-(4-methyl-1-piperazinylcarbonyl)-1-(4-nitrobenzyloxycarbonyl)pyrrolidine

1(a)

(2S,4S)-4-(4-Methoxybenzylthio)-2-pyrrolidinecarboxylic acid 4.0 g of (2S,4S)-2-carbamoyl-4-(4-methoxybenzylthio)pyrrolidine hydrochloride were dissolved in 40 ml of 2N aqueous hydrochloric acid, and the resulting solution was stirred for 1.5 hours on an oil bath at 95°–100° C. At the end of this time, the solution was cooled to room temperature, and then about 40 ml of a 2N aqueous solution f sodium hydroxide were added to the solution, whilst stirring, to adjust its pH to a value of between 4 and 6. The crystals which separated were collected by filtration, washed with water and dried in the air, to yield 3.25 g of the title compound as crystals, melting at 198°–200° C.

Nuclear Magnetic Resonance Spectrum (hexadeuterated dimethyl sulfoxide, 270 MHz), δ ppm: 1.69 (1H, doublet of triplets, J=13.2 & 8.3 Hz); 2.44 (1H, doublet of triplets, J=13.2 & 6.8 Hz); 2.90 (1H, doublet of triplets, J=11.2 & 7.8 Hz); 3.15–3.60 (4H, multiplet); 3.66 (1H, triplet, J=8.3 Hz); 3.73 (3H, singlet); 3.74 (2H, singlet); 6.88 (2H, doublet, J=8.8 Hz); 7.25 (2H, doublet, J=8.8 Hz).

Infrared Absorption Spectrum (KBr), $\nu_{max}$ cm$^{-1}$: 1610, 1576, 1511, 1445, 1376, 1243.

1(b)

(2S,4S)-4-(4-Methoxybenzylthio)-1-(4-nitrobenzyloxycarbonyl)-2-pyrrolidinecarboxylic acid 1.87 g of (2S,4S)-4-(4-methoxybenzylthio)-2-pyrrolidinecarboxylic acid [prepared as described in step (a) above] was suspended in 80 ml of a 1:1 by volume mixture of tetrahydrofuran and water. This suspension was then converted to a homogeneous solution by the addition of 7 ml of a 1N aqueous solution of sodium hydroxide. Whilst stirring this solution on an ice bath, 10 ml of a tetrahydrofuran solution containing 1510 mg of 4-nitrobenzyloxycarbonyl chloride and 7 ml of a 1N aqueous solution of sodium hydroxide were gradually added dropwise at the same time, and the resulting mixture was stirred under the same conditions for 10 minutes. At the end of this time, the tetrahydrofuran was removed by evaporation under reduced pressure. 1N aqueous hydrochloric acid was added to the reaction solution to adjust its pH to a value of between 2 and 3. The crystals which separated were collected by filtration, washed well with water and dried in the air. They were then further washed with a small amount of diethyl ether and dried, to obtain 2.42 g of the title compound, melting at 96°–98° C.

Nuclear Magnetic Resonance Spectrum (CDCl$_3$, 270 MHz), δ ppm: 2.03–2.18 (1H, multiplet); 2.52–2.68 (1H, multiplet); 3.08–3.22 (1H, multiplet); 3.27–3.42 (1H, multiplet); 3.72 (2H, singlet); 3.79 (3H, singlet); 3.77–3.98 (1H, multiplet); 4.38 (1H, triplet, J=7.3 Hz); 5.03–5.35 (2H, multiplet); 6.85 (2H, doublet, J=8.8 Hz); 7.22 (2H, doublet, J=8.8 Hz); 7.42, 7.48 (2H, two doublets, J=8.3 Hz); 8.16, 8.22 (2H, two doublets, J=8.3 Hz); 5.4–6.6 (1H, broad).

Infrared Absorption Spectrum (KBr), $\nu_{max}$ cm$^{-1}$: 3000, 1746, 1673, 1511, 1341, 1178.

1(c)

(2S,4S)-4-(4-Methoxybenzylthio)-2-(4-methyl-1-piperazinylcarbonyl)-1-(4-nitrobenzyloxycarbonyl)pyrrolidine 11.7 g of (2S,4S)-4-(4-methoxybenzylthio-1-(4-nitrobenzyloxycarbonyl)-2-pyrrolidinecarboxylic acid [prepared as described in step (b) above] were dissolved in 100 ml of anhydrous acetonitrile. 4.9 g of N,N'-carbonyldiimidazole were then added to the solution, which was then stirred for 30 minutes at room temperature. At the end of this time, 3.5 g of N-methylpiperazine were added to the reaction solution, and it was then stirred at room temperature for 30 minutes, and then at 40° C. for 30 minutes. The reaction solution was then condensed to 30 ml by evaporation under reduced pressure, an the residue was diluted with 300 ml of ethyl acetate. The resulting solution was washed once with 100 ml of a saturated aqueous solution of sodium hydrogencarbonate three times with 100 ml of water and once with 100 ml of a saturated aqueous solution of sodium chloride. The ethyl acetate layer was condensed by evaporation under reduced pressure, to obtain 1.36 g of a crystalline residue. Recrystallization of this crystalline residue from 100 ml of ethanol gave 13.0 g of the title compound as colorless needles, melting at 140°–141° C.

Infrared Absorption Spectrum (KBr), $\nu_{max}$ cm$^{-1}$: 1710, 1656, 1340.

Nuclear Magnetic Resonance Spectrum (CDCl$_3$, 270 MHz), δ ppm: 1.72–1.84 (1H, multiplet); 2.24–2.31 (5H, multiplet); 2.42–2.52 (2H, multiplet); 3.02–3.16 (1H, multiplet); 3.30–3.70 (5H, multiplet); 3.72 (2H, singlet); 3.79, 3.80 (together 3H, two singlets); 3.81–4.07 (1H, multiplet); 4.56, 4.61 (together 1H, two triplets, J=8.3 Hz); 5.01–5.31 (2H, two AB quartets, J=13.7 Hz); 6.85 (2H, doublet, J=8.8 Hz); 7.23 (2H, doublet, J=8.8 Hz); 7.43, 7.47 (together 2H, two doublets, J=8.8 Hz); 8.18, 8.23 (together 2H, two doublets, J=8.8 Hz).

Mass spectrum m/e: 528 (M+).

PREPARATION 2 TO 6

By using 2-(2-aminoethyl)-1-methylpyrrolidine, 4-aminomethylpyridine, N,N-dimethylethylenediamine, 1-methylhomopiperazine or 3-aminoquinuclidine, instead of 1-methylpiperazine, the following compounds were obtained by a similar procedure to that described in Preparation 1(c).

PREPARATION 2

(2S,4S)-4-(4-Methoxybenzylthio)-2-(1-methyl-2-pyrrolidinylethylcarbamoyl)-1-(4-nitrobenzyloxycarbonyl)pyrrolidine Infrared Absorption Spectrum (KBr), $\nu_{max}$ cm$^{-1}$: 1718, 1689, 1660, 1607, 1550, 1530, 1514, 1448.

Nuclear Magnetic Resonance Spectrum (CDCl$_3$, 270 MHz), δ ppm: 1.45–2.68 (14H, multiplet); 2.95–3.31 (4H, multiplet); 3.42–3.58 (1H, multiplet); 3.64–4.04 (1H, multiplet); 3.71 (2H, singlet); 3.79 (3H, singlet); 4.22–4.28 (1H, multiplet); 5.16, 5.26 (2H, AB, J=13, 67 Hz); 6.84 (2H, doublet, J=8.79 Hz); 7.22 (2H, doublet, J=8.79 Hz); 7.56, 8.14 (1H, two broad singlets); 8.21 (2H, doublet, J=8.79 Hz).

PREPARATION 3

(2S,4S)-4-(4-Methoxybenzylthio)-1-(4-nitrobenzyloxycarbonyl)-2-(4-pyridinylmethylcarbamoyl)pyrrolidine Infrared Absorption Spectrum (KBr), $\nu_{max}$ cm$^{-1}$: 1708, 1606, 1512, 1461, 1416.

Nuclear Magnetic Resonance Spectrum (CDCl$_3$, 270 MHz), δ ppm: 1.78–2.67 (3H, multiplet); 3.16–3.22 (1H, multiplet); 3.30–3.51 (1H, multiplet); 3.72 (2H, singlet); 3.80 (3H, singlet); 4.40 (1H, triplet, J=6.96 Hz); 4.40–4.62 (2H, multiplet); 5.15–5.28 (2H, multiplet); 6.85 (2H, doublet, J=8.05 Hz); 7.10–7.52 (2H, multiplet); 7.22 (2H, doublet, J=8.05 Hz); 8.21 (2H, doublet, J=7.33 Hz); 8.51 (2H, broad singlet).

PREPARATION 4

(2S,4S)-2-(2-Dimethylaminoethylcarbamoyl)-4-(4-methoxybenzylthio)-1-(4-nitrobenzyloxycarbonyl)pyrrolidine Infrared Absorption Spectrum (KBr), $\nu_{max}$ cm$^{-1}$: 1713, 1650, 1525, 1346.

Nuclear Magnetic Resonance Spectrum (CDCl$_3$, 270 MHz), δ ppm: 2.14, 2.22 (together 6H, two singlets); 2.23–2.65 (4H, multiplet); 3.06–3.17 (1H, multiplet); 3.22–3.46 (3H, multiplet); 3.72 (2H, singlet); 3.79 (3H, singlet); 3.75–4.06 (1H, multiplet); 4.25 (1H, broad singlet); 5.13–5.28 (2H, multiplet); 6.45–6.80 (1H, broad); 6.84 (2H, doublet, J=8.8 Hz); 7.22 (2H, doublet, J=8.8 Hz); 7.48 (2H, doublet, J=8.3 Hz); 8.22 (2H, doublet, J=8.3 Hz).

PREPARATION 5

(2S,4S)-4-(4-Methoxybenzylthio)-2-(4-methyl-1-homopiperazinylcarbonyl)-1-(4-nitrobenzyloxycarbonyl)pyrrolidine Infrared Absorption Spectrum (liquid film), $\nu_{max}$ cm$^{-1}$: 1710, 1650, 1513.

Nuclear Magnetic Resonance Spectrum (CDCl$_3$, 270 MHz), δ ppm: 1.73–2.04 (3H, multiplet); 2.23–2.77 (8H, multiplet); 3.02–3.16 (1H, multiplet); 3.33–4.08 (6H, multiplet); 3.70, 3.72 (together 2H, two singlets); 3.79, 3.80 (together 2H, two singlets); 4.15–4.63 (1H, multiplet); 5.01–5.34 (2H, multiplet); 6.85 (2H, doublet, J=8.79 Hz); 7.24 (2H, doublet, J=8.79 Hz); 7.45, 7.47 (together 2H, two doublets, J=8.79 Hz); 8.19, 8.23 (together 2H, two doublets, J=8.79 Hz).

PREPARATION 6

(4S)-4-(4-Methoxybenzylthio)-1-(4-nitrobenzyloxycarbonyl)-2-[(3-quinuclidinyl)carbamoyl]pyrrolidine Nuclear Magnetic Resonance Spectrum (CDCl$_3$, 270 MHz), δ ppm: 1.1–2.0 (5H, multiplet); 2.1–3.0 (7H, multiplet); 3.0–4.1 (5H, multiplet); 3.72 (2H, singlet); 3.77 (3H, singlet); 4.30 (1H, triplet, J=7 Hz); 5.23 (2H, singlet); 6.65 (1H, broad); 6.85 (2H, doublet, J=8.5 Hz); 7.26 (2H, doublet, J=8.5 Hz); 7.50 (2H, doublet, J=8.5 Hz); 8.25 (2H, doublet, J=8.5 Hz).

PREPARATION 7

(2S,4S)-2-[4-(2-Hydroxyethyl)-1-piperazinylcarbonyl]-4-(4-methoxybenzylthio)-1-(4-nitrobenzyloxycarbonyl)pyrrolidine 10.9 g of N,N'-carbonyldiimidazole were added to a solution of 25.0 g of (2S,4S)-4-(4-methoxybenzylthio)-1-(4-nitrobenzyloxycarbonyl)-2-pyrrolidinecarboxylic acid in 200 ml of anhydrous acetonirile, and the resulting mixture was stirred at room temperature for 1 hour. At the end of this time, a solution of 10.9 g of 1-(2-hydroxyethyl)piperazine in 50 ml of anhydrous acetonitrile was added to the mixture, which was then stirred at room temperature for 45 minutes. The reaction mixture was then concentrated by evaporation under reduced pressure, and the resulting residue was diluted with 800 ml of ethyl acetate and then washed, three times with 200 ml of water, and then once with 150 ml of an aqueous solution of sodium chloride. The ethyl acetate layer was concentrated by evaporation under reduced pressure to a volume of 100 ml, and the crystals which precipitated were collected by filtration, to give 28.6 g of the title compound as colorless crystals, melting at 140°–141° C.

Infrared Absorption Spectrum (KBr), $\nu_{max}$ cm$^{-1}$: 1710, 1653, 1670, 1512, 1439, 1404, 1344.

Nuclear Magnetic Resonance Spectrum (CDCl$_3$, 270 MHz), δ ppm: 1.48–1.85 (2H, multiplet); 2.32–2.64 (6H, multiplet); 2.59 (2H, triplet, J=5.37 Hz); 3.03–3.16 (1H, multiplet); 3.30–3.71 (5H, multiplet); 3.65 (2H, triplet, J=5.37 Hz); 3.73 (2H, singlet); 3.79, 3.80 (together 3H, two singlets); 3.82–4.07 (1H, multiplet); 4.56, 4.61 (together 1H, two triplets, J=8.30 Hz); 5.02–5.31 (2H, multiplet); 6.85 (2H, doublet, J=8.79 Hz); 7.23 (2H, doublet, J=8.79 Hz); 7.43, 7.47 (together 2H, two doublets, J=8.79 Hz); 8.18, 8.23 (together 2H, two doublets, J=8.79 Hz).

PREPARATION 8

(2S,4S)-4-(4-Methoxybenzylthio)-2-(1-methyl-4-pyridiniomethylcarbamoyl)-1-(4-nitrobenzyloxycarbonyl)pyrrolidine fluorosulfonate 326 mg of (2S,4S)-4-(4-methoxybenzylthio)-2-(4-pyridiniomethylcarbamoyl)-1-(4-nitrobenzyloxycarbonyl)pyrrolidine were dissolved in 6 ml of methylene chloride, and the solution was placed on an ice bath. 57 μl of methyl fluorosulfonate were then added to the solution, still on the ice bath, and the resulting mixture was stirred for 1 hour at room temperature. At the end of this time, the solvent was removed by distillation under reduced pressure, to obtain 395 mg of the title compound as a powder.

Infrared Absorption Spectrum (KBr), $\nu_{max}$ cm$^{-1}$: 1704, 1644, 1608, 1581, 1513, 1344, 1287, 1246.

Nuclear Magnetic Resonance Spectrum (D$_2$O, 270 MHz), δ ppm: 1.85–1.90 (1H, multiplet); 2.45–2.54 (1H, multiplet); 3.16–3.35 (2H, multiplet); 3.59 (2H, singlet); 3.64 (3H, singlet); 3.64–4.48 (4H, multiplet); 4.00, 4.11 (together 3H, two singlets); 4.98–5.17 (2H, multiplet); 6.77, 6.79 (together 2H, two doublets, J=8.79 Hz); 7.13 (2H, doublet, J=8.79 Hz); 7.30 (1H, doublet, J=8.06 Hz); 7.39 (1H, doublet, J=8.79 Hz); 7.56 (1H, doublet, J=6.59 Hz); 7.67 (1H, doublet, J=6.59 Hz); 8.01 (1H, doublet, J=8.06 Hz); 8.06 (1H, doublet, J=8.79 Hz); 8.23 (1H, doublet, J=6.59 Hz); 8.38 (1H, doublet, J=8.59 Hz).

PREPARATION 9

(2S,4S)-2-[4-(2-Carbamoyloxyethyl)-1-piperazinylcarbonyl[-4-(4-methoxybenzylthio)-1-(4-nitrobenzyloxycarbonyl)pyrrolidine 1.43 ml of trichloroacetyl isocyanate was added, whilst ice-cooling, to a solution of 5.59 g of (2S,4S)-2-[4-(2-hydroxyethyl)-1-piperazinylcarbonyl]-4-(4-methoxybenzylthio)-1-(4-nitrobenzyloxycarbonyl)pyrrolidine in 50 ml of anhydrous methylene chloride, and the resulting mixture was stirred at the same temperature for 30 minutes. At the end of this time, the solvent was removed by distillation under reduced pressure, the resulting residue was dissolved in 120 ml of methanol, and the solution was stirred at room temperature for 4.5 hours in the presence of 35 g of silica gel (a product of Merck & Co., Inc., silica gel 60, 230–400 mesh). The silica gel was removed by filtration, and the filtrate was freed from methanol by evaporation under reduced pressure. The resulting residue was purified by column chromatography through silica gel. Those fractions eluted with an 8:1 by volume mixture of ethyl acetate and methanol were collected and concentrated by evaporation under reduced pressure, to give 5.76 g of the title compound as a colorless powder.

Infrared Absorption Spectrum (KBr), $\nu_{max}$ cm$^{-1}$: 3353, 1711, 1652, 1608, 1513, 1344, 1242.

Nuclear Magnetic Resonance Spectrum (hexadeuterated dimethyl sulfoxide, 270 MHz), δ ppm: 1.38–1.57 (1H, multiplet); 2.14–2.70 (7H, multiplet); 2.98–4.08 (9H, multiplet); 3.72, 3.74 (together 3H, two singlets); 3.77 (2H, singlet); 4.66, 4.77 (together 1H, two triplets, J=7.81 Hz); 5.02–5.25 (2H, multiplet); 6.45 (2H, broad singlet); 6.88 (2H, doublet, J=8.79 Hz); 7.26 (2H, doublet, J=8.79 Hz); 7.52, 7.60 (together 2H, two doublets, J=8.79 Hz); 8.20, 8.24 (together 2H, two doublets, J=8.79 Hz).

PREPARATIONS 10 TO 13

The procedure described in Preparation 7 was repeated, but using 1-carbamoylmethylpiperazine, 1-(4-nitrobenzyloxycarbonylmethyl)piperazine, 1-(4-nitrobenzyloxycarbonylmethyl)homopiperazine, and 1,2-dimethylpiperazine, respectively, in place of 1-(2-hydroxyethyl)piperazine, to prepare the following compounds.

PREPARATION 10

(2S,4S)-2-(4-Carbamoylmethylpiperazinylcarbonyl)-4-(4-methoxybenzylthio)-1-(4-nitrobenzyloxycarbonyl)-pyrrolidine Infrared Absorption Spectrum (KBr), $\nu_{max}$ cm$^{-1}$: 1708, 1654, 1608, 1583, 1513, 1438, 1404, 1344, 1300, 1241.

Nuclear Magnetic Resonance Spectrum (CDCl$_3$, 270 MHz), δ ppm: 1.72–1.83 (1H, multiplet); 2.02–2.10 (1H, multiplet); 2.34–2.72 (5H, multiplet); 2.99–3.18 (3H, multiplet); 3.30–3.64 (4H, multiplet); 3.73 (2H, singlet); 3.79, 3.80 (together 3H, two singlets); 3.82–4.13 (1H, multiplet); 4.52–4.77 (1H, multiplet); 5.01–5.36 (2H, multiplet); 5.56 (1H, broad singlet); 6.77, 6.88 (together 1H, two broad singlets); 6.84, 6.85 (together 2H, two doublets, J=8.79 Hz); 7.22, 7.23 (together 2H, two doublets, J=8.79 Hz); 7.43, 7.47 (together 2H, two doublets, J=8.79 Hz); 8.19, 8.23 (together 2H, two doublets, J=8.79 Hz).

PREPARATION 11

(2S,4S)-4-(4-Methoxybenzylthio)-2-[4-(4-nitrobenzyloxycarbonylmethyl)-1-piperazinylcarbonyl]-1-(4-nitrobenzyloxycarbonyl)pyrrolidine Infrared Absorption Spectrum (KBr), $\nu_{max}$ cm$^{-1}$: 1750, 1710, 1655, 1520, 1345.

Nuclear Magnetic Resonance Spectrum (CDCl$_3$, 270 MHz), δ ppm: 1.73–1.84 (1H, multiplet); 2.41–2.70 (5H, multiplet); 3.02–3.17 (1H, multiplet); 3.29, 3.30 (together 3H, two singlets); 3.37–3.70 (5H, multiplet); 3.72 (2H, singlet); 3.78, 3.79 (together 3H, two singlets); 3.82–4.07 (1H, multiplet); 4.53–4.63 (1H, multiplet); 5.01–5.31 (4H, multiplet); 6.85 (2H, doublet, J=8.3 Hz); 7.23 (2H, doublet, J=8.3 Hz); 7.42–7.53 (4H, multiplet); 8.18–8.25 (4H, multiplet).

PREPARATION 12

(2S,4S)-4-(4-Methoxybenzylthio)-2-[4-(4-nitrobenzyloxycarbonylmethyl)-1-homopiperazinylcarbonyl]-1-(4-nitrobenzyloxycarbonyl)pyrrolidine Infrared Absorption Spectrum (liquid film), $\nu_{max}$ cm$^{-1}$: 1748, 1709, 1650, 1608, 1520, 1429, 1404, 1346.

Nuclear Magnetic Resonance Spectrum (CDCl$_3$, 270 MHz), δ ppm: 1.71–2.03 (3H, multiplet); 2.42–3.17 (6H, multiplet); 3.32–4.08 (8H, multiplet); 3.73 (2H, singlet); 3.80, 3.82 (together 3H, two singlets); 4.49–4.63 (1H, multiplet); 5.02–5.35 (4H, multiplet); 6.85 (2H, doublet, J=8.30 Hz); 7.23 (2H, doublet, J=8.30 Hz); 7.43–7.52 (4H, multiplet); 8.15–8.25 (4H, multiplet).

PREPARATION 13

(2S,4S)-2-(3,4-Dimethyl-1-piperazinylcarbonyl)-4-(4-methoxybenzylthio)-1-(4-nitrobenzyloxycarbonyl)pyrrolidine Infrared Absorption Spectrum (KBr), $\nu_{max}$ cm$^{-1}$: 1711, 1655, 1608, 1513, 1439, 1403, 1344.

Nuclear Magnetic Resonance Spectrum (CDCl$_3$, 270 MHz), δ ppm: 1.01, 1.07 (together 3H, two doublets, J=6.35 Hz); 1.67–3.17 (8H, multiplet); 2.27, 2.29 (together 3H, two singlets); 3.29–4.08 (3H, multiplet); 3.72 (2H, singlet); 3.79, 3.80 (together 3H, two singlets); 4.18–4.44 (1H, multiplet); 4.50–4.67 (1H, multiplet); 5.00–5.32 (2H, multiplet); 6.85 (2H, doublet, J=8.30 Hz); 7.23 (2H, doublet, J=8.30 Hz); 7.39–7.49 (2H, multiplet); 8.16–8.24 (2H, multiplet).

PREPARATION 14

(2S,4S)-2-({4-[2-(4-Nitrobenzyloxycarbonyl)oxyethyl[-1-piperazinylcarbonyl}-4-(4-methoxybenzylthio)-1-(4-nitrobenzyloxycarbonyl)pyrrolidine 5.86 g of 4-dimethylaminopyridine and a solution of 10.35 g of p-nitrobenzyl chloroformate in 40 ml of anhydrous methylene chloride were added to a solution of 22.35 g of (2S,4S)-2-[4-(2-hydroxyethyl)-1-piperazinylcarbonyl]-4-(4-methoxybenzylthio)-1-(4-nitrobenzyloxycarbonyl)pyrrolidine (prepared as described in Preparation 7) in 160 ml of anhydrous methylene chloride, and the resulting mixture was stirred at room temperature for 1 hour. At the end of this time, the reaction mixture was diluted with 300 ml of ethyl acetate and washed with 100 ml of water, with 100 ml of a saturated aqueous solution of sodium hydrogencarbonate and with 100 ml of a saturated aqueous solution of sodium chloride, in that order. The solvents were removed by distillation under reduced pressure, and the resulting residue was purified by column chromatography through silica gel. Those fractions eluted with ethyl acetate were collected and concentrated by evaporation under reduced pressure, to give 26.35 g of the title compound as a colorless powder.

Infrared Absorption Spectrum (KBr), $\nu_{max}$ cm$^{-1}$: 1748, 1710, 1655, 1608, 1521, 1346, 1251.

Nuclear Magnetic Resonance Spectrum (CDCl$_3$, 270 MHz), δ ppm: 1.72–1.84 (1H, multiplet); 2.26–2.73 (6H, multiplet); 2.97–3.16 (1H, multiplet); 3.29–4.10 (1H, multiplet); 3.72 (2H, singlet); 3.79, 3.80 (together 3H, two singlets); 4.24–4.31 (2H, multiplet); 4.52–4.63 (1H, multiplet); 5.00–5.35 (4H, multiplet); 6.85 (2H, doublet, J=8.79 Hz); 7.23 (2H, doublet, J=8.79 Hz); 8.41–7.57 (4H, multiplet); 8.16–8.25 (4H, multiplet).

PREPARATION 15

(2S,4R)-4-Hydroxy-2-{4-[2-(4-nitrobenzyloxycarbonyl)oxyethyl]-1-piperazinylcarbonyl}-1-(4-nitrobenzyloxycarbonyl)pyrrolidine This Preparation illustrates three different ways of producing the same title compound.

15(a)

25.7 ml of diethyl cyanophosphonate and 68.7 ml of triethylamine were added dropwise, whilst ice-cooling, to a suspension of 47.8 g of trans-4-hydroxy-1-(4-nitrobenzyloxycarbonyl)-L-proline and 64.8 g of 1-[2-(4-nitrobenzyloxycarbonyloxy)ethyl)piperazine dihydrochloride in 400 ml of anhydrous dimethylformamide, and the resulting mixture was stirred at the same temperature for 30 minutes. At the end of this time, the reaction mixture was diluted with 1.5 liters of ethyl acetate and washed with water. The organic layer was dried over anhydrous magnesium sulfate and concentrated by evaporation under reduced pressure, to afford 87.6 g of the title compound as a powder.

Infrared Absorption Spectrum (KBr), $v_{max}$ cm$^{-1}$: 1749, 1709, 1650, 1607, 1522, 1499, 1347, 1263.

Nuclear Magnetic Resonance Spectrum (CDCl$_3$, 270 MHz), δ ppm: 1.63 (1H, singlet); 1.92–2.38 (8H, multiplet); 3.41–3.83 (6H, multiplet); 4.24–4.32 (2H, multiplet); 4.55–4.60 (1H, multiplet); 4.79–4.90 (1H, multiplet); 5.03–5.35 (4H, multiplet); 7.44–7.57 (4H, multiplet); 8.17–8.25 (4H, multiplet).

15(b)

608 μl of chlorotrimethylsilane and 670 μl of triethylamine were added, whilst ice-cooling, to a solution of 620 mg of trans-4-hydroxy-1-(4-nitrobenzyloxycarbonyl)-L-proline dissolved in 20 ml of anhydrous acetonitrile, and the resulting mixture was stirred at room temperature for 1hour. At the end of this time, the solvent was removed by distillation under reduced pressure, and the resulting residue was mixed with an aqueous solution of sodium chloride and then extracted with ethyl acetate. The extract was washed with an aqueous solution of sodium chloride, dried over anhydrous magnesium sulfate and freed from the solvent by distillation under reduced pressure, to afford 648 mg of trans-1-(4-nitrobenzyloxycarbonyl)-4-trimethylsilyloxy-L-proline as a powder. The whole of this product was then dissolved in 14 ml of anhydrous acetonitrile, and 330 mg of N,N'-carbonyldiimidazole were added to the solution. The mixture was then stirred at room temperature for 1 hour. At the end of this time, a solution of 630 mg of 1-[2-(4-nitrobenzyloxycarbonyl)oxyethyl)piperazine in 2 ml of anhydrous acetonitrile was added to the reaction mixture, and the resulting mixture was stirred overnight at room temperature and then at 40° C. for 1 hour. At the ed of this time, 14 ml of 1N aqueous hydrochloric acid were added, and the reaction mixture was stirred at room temperature for 1 hour. It was then made basic by the addition of an aqueous solution of sodium hydrogencarbonate, after which it was extracted with ethyl acetate. The ethyl acetate layer was washed with water, dried over anhydrous magnesium sulfate and freed from the solvent by distillation under reduced pressure. The resulting residue was subjected to column chromatography through silica gel using a 9:1 by volume mixture of ethyl acetate and methanol as the eluent. Those fractions containing the title compound were collected and concentrated by evaporation under reduced pressure, to afford 589 mg of the title compound as a powder. The infra-red absorption spectrum and nuclear magnetic resonance spectrum of the product thus obtained were identical with those of the compound prepared as describe din step (a), above.

15(c)

674 mg of trans-1-(4-nitrobenzyloxycarbonyl)-4-trimethylsilyloxy-L-proline [prepared as described in step (2) above] were dissolved in 14 ml of anhydrous acetonitrile, and 343 mg of N,N'-carbonyldiimidazole were added to the resulting solution. The resulting mixture was then stirred at room temperature for 1 hour. At the end of this time, a solution of 275 mg of 1-(2-hydroxyethyl)piperazine in 1 ml of anhydrous acetonitrile was added to the reaction mixture, and the resulting mixture was stirred overnight at room temperature. It was then concentrated by evaporation under reduced pressure, and the resulting residue was mixed with an aqueous solution of sodium chloride and extracted with ethyl acetate. The extract was washed with water and dried over anhydrous magnesium sulfate. The solvent was removed by distillation under reduced pressure, to give 574 mg of (2S,4R)-2-(4-(2-hydroxyethyl)-1-piperazinylcarbonyl)-4-trimethylsilyloxy-1-(4-nitrobenzyloxycarbonyl)pyrrolidine as an oil. The whole of this product was dissolved in 5.7 ml of methylene chloride, and 170 mg of 4-dimethylaminopyridine and 300 mg of 4-nitrobenzyl chloroformate were added to the resulting solution, whilst ice-cooling. The mixture was then stirred at room temperature for 1 hour, after which the solvent was removed by distillation under reduced pressure. The resulting residue was mixed with 15 ml of 1N aqueous hydrochloric acid and then stirred at room temperature for 1 hour. At the end of this time, the mixture was made mildly basic by the addition of an aqueous solution of sodium hydrogen-carbonate; it was then extracted with ethyl acetate. The extract was washed with water and dried over anhydrous magnesium sulfate; the solvent was then removed by distillation under reduced pressure, and the resulting residue was purified in a similar manner to that described in step (b) above, to afford 348 mg of the title compound. The infra-red absorption spectrum and nuclear magnetic resonance spectrum of the product thus obtained were identical with those of the compound prepared as described in step (a), above.

PREPARATION 16

(2S,4S)-4-Acetylthio-2-{4-[2-(4-nitrobenzyloxycarbonyl)oxyethyl]-1-piperazinylcarbonyl}-1-(4-nitrobenzyloxycarbonyl)pyrrolidine This Preparation illustrates two different ways of producing the same title compound.

16(a)

(2S,4S)-4-Acetylthio-2-{4-[2-(4-nitrobenzyloxycarbonyl)oxyethyl]-1-piperazinylcarbonyl}-1-(4-nitrobenzyloxycarbonyl)pyrrolidine 105 g of (2S,4R)-4-hydroxy-2-{4-[2-(4-nitrobenzyloxycarbonyl)oxyethyl]-1-piperazinylcarbonyl}-1-(4-nitrobenzyloxycarbonyl)pyrrolidine (prepared as described in Preparation 15) and 55 g of triphenylphosphine were dissolved in 700 ml of tetrahydrofuran, and a solution of 36.5 g of diethyl azodicarboxylate in 100 ml of tetrahydrofuran was added dropwise to it, whilst ice-cooling. The resulting mixture was then stirred at the same temperature for 10 minutes. At the end of this time, a solution of 15.9 g of mercaptoacetic acid in 100 ml of tetrahydrofuran was added dropwise to the mixture, and the resulting mixture was stirred at room temperature for 1 hour. The mixture was then concentrated by evaporation under reduced pressure. The concentrate was dissolved in 1.5 liters of ethyl acetate and washed with water and with an aqueous solution of sodium chloride, in that order. The organic layer was dried over anhydrous sodium sulfate and then concentrated by evaporation under reduced pressure. The resulting residue was mixed with 400 ml of diisopropyl ether and a soluble material was removed. This procedure was repeated four times in all. The residue was subjected to column chromatography through 3 kg of silica gel using mixtures of ethyl acetate and methanol ranging from 1:0 to 20:1 by volume as the eluent. Those fractions containing the title compound were collected and concentrated by evaporation under reduced pressure, to afford 88.4 g of the title compound as a colorless powder.

Infrared Absorption Spectrum (KBr), $\nu_{max}$ cm$^{-1}$.

Nuclear Magnetic Resonance Spectrum (CDCl$_3$, 270 MHz), δ ppm:
1.82–1.93 (1H, multiplet);
2.34 (3H, singlet);
2.35–2.82 (7H, multiplet);
3.37–3.70 (5H, multiplet);
3.91–4.05 (1H, multiplet);
4.07–4.17 (1H, multiplet);
4.23–4.36 (2H, multiplet);
4.64–4.77 (1H, multiplet);
5.02–5.35 (4H, multiplet);
7.43–7.57 (4H, multiplet);
8.18–8.26 (4H, multiplet).

16(b1)
(2S,4R)-4-Methanesulfonyloxy-2-{4-[2-(4-nitrobenzyloxycarbonyl)oxyethyl]-1-piperazinylcarbonyl}-1-(4-nitrobenzyloxycarbonyl)pyrrolidine 89 μl of triethylamine and 50 μl of methanesulfonyl chloride were added to a solution of 321 mg of (2S,4R)-4-hydroxy-2-{4-[2-(4-nitrobenzyloxycarbonyl)oxyethyl]-1-piperazinylcarbonyl}-1-(4-nitrobenzyloxycarbonyl)pyrrolidine in 3.2 ml of anhydrous tetrahydrofuran, whilst ice-cooling, and the resulting mixture was stirred at 0° to 5° C. for 30 minutes and then at room temperature for 1 hour. The reaction mixture was then concentrated by evaporation under reduced pressure, and the residue was mixed with an aqueous solution of sodium hydrogencarbonate and then extracted with ethyl acetate. The extract was washed with an aqueous solution of sodium chloride and dried over anhydrous magnesium sulfate; the solvent was then removed by distillation under reduced pressure, to afford 345 mg of the title compound as a powder.

Infrared Absorption Spectrum (KBr), $\nu_{max}$ cm$^{-1}$: 1751, 1710, 1654, 1607, 1523, 1436, 1406.

Nuclear Magnetic Resonance Spectrum (CDCl$_3$, 270 MHz), δ ppm:
2.22–3.01 (8H, multiplet);
3.06 (3H, singlet);
3.40–4.03 (6H, multiplet);
4.25–4.47 (2H, multiplet);
4.84 and 4.89 (together 1H, two triplets, J=7.33 Hz);
5.04–5.37 (5H, multiplet);
7.46 and 7.50 (together 2H, two doublets, J=8.79 Hz);
7.56 (2H, doublet, J=8.79 Hz);
8.19–8.26 (4H, multiplet);

16(b2)
(2S,4S)-4-Acetylthio-2-{4-[2-(4-nitrobenzyloxycarbonyl)oxyethyl]-1-piperazinylcarbonyl}-1-(4-nitrobenzyloxycarbonyl)pyrrolidine 51 μl of thioacetic acid were added to a suspension of 26 mg of sodium hydride (as a 55% W/W dispersion in mineral oil) in 1.4 ml of anhydrous dimethylformamide, whilst ice-cooling, and the resulting mixture was stirred at room temperature for 30 minutes. At the end of this time, a solution of 340 mg of (2S,4R)-4-methanesulfonyloxy-2-{4-[2-(4-nitrobenzyloxycarbonyl)oxyethyl]-1-piperazinylcarbonyl}-1-(4-nitrobenzyloxycarbonyl)pyrrolidine {prepared as described in step (b1) above} in 2 ml of anhydrous dimethylformamide was added to the mixture, and the resulting mixture was stirred at 80°–90° C. for 4 hours, after which the reaction mixture was allowed to cool to room temperature. The reaction mixture was then poured into an aqueous solution of sodium chloride and extracted with ethyl acetate. The extract was washed with water, dried over anhydrous magnesium sulfate and freed from the solvent by distillation under reduced pressure. The residue was purified in a similar manner to that described in step (a), above, to afford the title compound (166 mg). The infra-red absorption spectrum and nuclear magnetic resonance spectrum of the product thus obtained were identical with those of the compound obtained as described in step (a), above.

PREPARATION 17

(2S,4S)-4-(4-Methoxybenzylthio)-2-{4-[2-(4-nitrobenzyloxycarbonyl)oxyethyl]-1-homopiperazinylcarbonyl}-1-(4-nitrobenzyloxycarbonyl)pyrrolidine 860 mg of (2S,4S)-4-(4-methoxybenzylthio)-1-(4-nitrobenzyloxycarbonyl)-2-pyrrolidinecarboxylic acid [prepared as described in Preparation 1(b)] were dissolved in 8 ml of anhydrous acetonitrile, and 410 mg of N,N'-carbonyldiimidazole were added to the resulting solution. The resulting mixture was then stirred at room temperature for 30 minutes, after which a solution of 1250 mg of 4-[2-(4-nitrobenzyloxycarbonyl)oxyethyl]-homopiperazine bis(trifluoroacetate)in 5 ml of acetonitrile and 860 μl of diisopropylethylamine were added, in that order. The resulting mixture was then stirred at room temperature for 35 hours. At the end of this time, the reaction mixture was diluted with 100 ml of ethyl acetate and washed with an aqueous solution of sodium hydrogencarbonate and with an aqueous solution of sodium chloride, in that order. The organic layer was then dried over anhydrous sodium sulfate and concentrated by evaporation under reduced pressure. The residue was subjected to column chromatography through silica gel using mixtures of ethyl acetate and methanol ranging from 98:2 to 95:5 by volume as the eluent. Those fractions containing the title compound were collected and concentrated by evaporation under reduced pressure, to afford 900 mg of the title compound.

Infrared Absorption Spectrum (KBr), $\nu_{max}$ cm$^{-1}$: 1748, 1709, 1650, 1521, 1347, 1254.

Nuclear Magnetic Resonance Spectrum (CDCl$_3$, 270 MHz), δ ppm:

1.71-1.89 (2H, multiplet);
2.42-2.86 (7H, multiplet);
3.01-3.13 (1H, multiplet);
3.32-3.88 (8H, multiplet);
3.72 (2H, singlet);
3.78 and 3.80 (together 3H, two singlets);
4.01-4.27 (3H, multiplet);
4.51-4.61 (1H, multiplet);
5.00-5.33 (4H, multiplet);
6.84 (2H, doublet, J=8.3 Hz);
7.23 (2H, doublet, J=8.3 Hz);
7.41-7.56 (4H, multiplet);
8.16-8.24 (4H, multiplet).

PREPARATION 18

(2S,4S)-2-[4-(2-Carbamoyloxyethyl)-1-homopiperazinylcarbonyl]-4-(4-methoxybenzylthio)-1-(4-nitrobenzyloxycarbonyl)pyrrolidine and (2S,4S)-2-(4-Carbamoylmethyl-1-homopiperazinylcarbonyl)-4-(4-methoxybenzylthio-1-(4-nitrobenzyloxycarbonyl)-pyrrolidine A procedure similar to that described in Preparation 17 was repeated, except that 4-(2-carbamoyloxyethyl)-homopiperazine bis(trifluoroacetate) and 4-carbamoylmethylhomopiperazine bis(trifluoroacetate) were used instead of 4-[2-(4-nitrobenzyloxycarbonyl)oxyethyl]-homopiperazine bis(trifluoroacetate), to give the title compounds.

We claim:
1. A compound of formula (I):

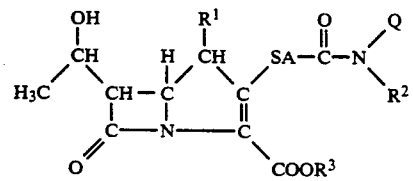

in which:
A is a fully saturated heterocyclic group having from 4 to 6 ring atoms, of which one is a nitrogen atom and the remainder are carbon atoms, said nitrogen atom having on its remaining valence a group or atom $R^4$, wherein:
 $R^4$ is a hydrogen atom; an alkenyl group having from 2 to 5 carbon atoms; an alkynyl group having from 2 to 5 carbon atoms; an alkyl group having from 1 to 6 carbon atoms; a substituted alkyl group having from 1 to 6 carbon atoms and having at least one substituent selected from the group consisting of substituents (a), defined below; or a group of formula —C(=NH)$R^5$, wherein $R^5$ is a hydrogen atom or an alkyl group having from 1 to 6 carbon atoms;
$R^1$ is a hydrogen atom or a methyl group;
$R^2$ is a hydrogen atom or an alkyl group having from 1 to 6 carbon atoms;
$R^3$ is a hydrogen atom or a negative ionic charge or forms an ester;
Q is
 (i) a group of formula —B—N$^+$R$^8$R$^9$R$^{10}$, wherein:
 $R^8$, $R^9$ and $R^{10}$ are independently selected from the group consisting of alkenyl groups having from 2 to 5 carbon atoms, alkynyl groups having from 2 to 5 carbon atoms, alkyl groups having from 1 to 6 carbon atoms and substituted alkyl groups which have from 1 to 6 carbon atoms and which have at least one substituent selected from the group consisting of substituents (b), defined below; and B represents an alkylene or alkylidene group having from 1 to 4 carbon atoms;
substituents (a):
hydroxy groups, carboxy groups, cyano groups, sulfamoyl groups, sulfo groups, halogen atoms, and groups of formula —NR$^a$R$^b$ or —CONR$^a$R$^b$, where R$^a$ and R$^b$ are independently selected from the group consisting of hydrogen atoms and alkyl groups having from 1 to 4 carbon atoms;
substituents (b):
hydroxy groups; carboxy groups; groups of formula —NR$^a$R$^b$, where R$^a$ and R$^b$ are as defined above; groups of formula —CONR$^c$R$^d$ or —OCONR$^c$R$^d$, where R$^c$ and R$^d$ are independently selected from the group consisting of hydrogen atoms, alkyl groups having from 1 to 4 carbon atoms and substituted alkyl groups which have from 1 to 4 carbon atoms and which have at least one substituent selected from the group consisting of substituents (d) defined below; cyano groups; sulfamoyl groups; ureido groups; sulfo groups; halogen atoms; alkoxy groups having from 1 to 4 carbon atoms; alkoxycarbonyl groups having from 2 to 5 carbon atoms; alkanoyl groups having from 1 to 4 carbon atoms; alkanoylamino groups having from 1 to 4 carbon atoms; alkanoyloxy groups having from 1 to 4 carbon atoms; alkylthio groups having from 1 to 4 carbon atoms; alkylsulfinyl groups having from 1 to 4 carbon atoms and alkylsulfonyl groups having from 1 to 4 carbon atoms;
substituents (d):
hydroxy groups, carboxy groups and groups of formula —CONR$^a$R$^b$ or —OCONR$^a$R$^b$, where R$^a$ and R$^b$ are as defined above;
or a pharmaceutically acceptable salt thereof and, where $R^3$ is a hydrogen atom or forms an ester compound, the compound also includes an anion provided by a pharmaceutically acceptable acid.

2. The compound of claim 1, wherein:
A is a fully saturated heterocyclic group having from 4 to 6 ring atoms, of which one is a nitrogen atom and the remainder are carbon atoms, said nitrogen atom having on its remaining valence a group or atom $R^4$, wherein:
 $R^4$ is a hydrogen atom; an alkenyl group having 3 or 4 carbon atoms; an alkynyl group having 3 or 4 carbon atoms; an alkyl group having 1 or 4 carbon atoms; a substituted alkyl group which has from 1 or 4 carbon atoms and which has at least one substituent selected from the group consisting of substituents (a$^i$), defined below; or a group of formula —C(=NH)$R^5$, wherein $R^5$ is a hydrogen atom or an alkyl group having from 1 to 4 carbon atoms;
substituents (a$^i$):
hydroxy groups, carboxy groups, carbamoyl groups, cyano groups, sulfamoyl groups, sulfo groups, halogen atoms, and groups of formula —NR$^{a'}$R$^{b'}$, where R$^{a'}$ and R$^{b'}$ are independently selected from the group consisting of hydrogen atoms and alkyl groups having from 1 to 3 carbon atoms.

3. The compound of claim 1, wherein $R^2$ is a hydrogen atom or an alkyl group having from 1 to 4 carbon atoms.

4. The compound of claim 1, wherein:

$R^8$, $R^9$ and $R^{10}$ are independently selected from the group consisting of alkenyl groups having 3 or 4 carbon atoms, alkynyl groups having 3 or 4 carbon atoms, alkyl groups having from 1 to 4 carbon atoms and substituted alkyl groups which have from 1 to 4 carbon atoms and which have at least one substituent selected from the group consisting of substituents (b$^j$), defined below; and B is an alkylene or alkylidene group having from 1 to 4 carbon atoms;

substituents (b$^j$):

hydroxy groups; carboxy groups; groups of formula —NR$^a$R$^b$, where R$^a$ and R$^b$ are as defined in claim 1; groups of formula —CONR$^c$R$^d$ or —OCONR$^{c''}$R$^{d''}$, where R$^c$ and R$^d$ are independently selected from the group consisting of hydrogen atoms, alkyl groups having from 1 to 3 carbon atoms and substituted alkyl groups which have from 1 to 3 carbon atoms and which have at least one substituent selected from the group consisting of substituents (d$^j$) defined below, and R$^{c''}$ and R$^{d''}$ are independently selected from the group consisting of hydrogen atoms and alkyl groups having from 1 to 3 carbon atoms; cyano groups; sulfamoyl groups; ureido groups; sulfo groups; halogen atoms; alkoxy groups having from 1 to 3 carbon atoms; alkoxycarbonyl groups having from 2 to 4 carbon atoms; alkanoyl groups having from 1 to 3 carbon atoms; alkanoylamino groups having from 1 to 3 carbon atoms; alkanoyloxy groups having from 1 to 3 carbon atoms; alkylthio groups having from 1 to 3 carbon atoms; alkylsulfinyl groups having from 1 to 3 carbon atoms and alkylsulfonyl groups having from 1 to 3 carbon atoms; and substituents (d$^j$):

hydroxy groups; carboxy groups; carbamoyl groups; and carbamoyloxy groups.

5. The compound of claim 1, wherein:

A is a fully saturated heterocyclic group having from 4 to 6 ring atoms, of which one is a nitrogen atom and the remainder are carbon atoms, said nitrogen atom having on its remaining valence a group or atom $R^4$, wherein:

$R^4$ is a hydrogen atom; an alkenyl group having 3 or 4 carbon atoms; an alkynyl group having 3 or 4 carbon atoms; an alkyl group having from 1 to 4 carbon atoms; a substituted alkyl group which has from 1 to 4 carbon atoms and which has at least one substituent selected from the group consisting of substituents (a$^i$), defined below; or a group of formula —C(=NH)R$^5$, wherein $R^5$ is a hydrogen atom or an alkyl group having from 1 to 4 carbon atoms;

$R^2$ is a hydrogen atom or an alkyl group having from 1 to 4 carbon atoms;

Q is a group of formula —B—N+R$^8$R$^9$R$^{10}$, wherein:

$R^8$, $R^9$ and $R^{10}$ are independently selected from the group consisting of alkenyl groups having 3 or 4 carbon atoms, alkynyl groups having 3 or 4 carbon atoms, alkyl groups having from 1 to 4 carbon atoms and substituted alkyl groups having from 1 to 6 carbon atoms and having at least one substituent selected from the group consisting of substituents (b$^j$), defined below; and B is an alkylene or alkylidene group having from 1 to 4 carbon atoms;

substituents (a$^j$):

hydroxy groups, carboxy groups, carbamoyl groups, cyano groups, sulfamoyl groups, sulfo groups, halogen atoms, and groups of formula —NR$^{a'}$R$^{b'}$, where R$^{a'}$ and R$^{b'}$ are independently selected from the group consisting of hydrogen atoms and alkyl groups having from 1 to 3 carbon atoms;

substituents (b$^j$):

hydroxy groups; carboxy groups; groups of formula —NR$^a$R$^b$, where R$^a$ and R$^b$ are as defined in claim 1; groups of formula —CONR$^c$R$^d$ or —OCONR$^{c''}$R$^{d''}$, where R$^c$ and R$^d$ are independently selected from the group consisting of hydrogen atoms, alkyl groups having from 1 to 3 carbon atoms and substituted alkyl groups which have from 1 to 3 carbon atoms and which have at least one substituent selected from the group consisting of substituents (d$^j$) defined below, and R$^{c''}$ and R$^{d''}$ are independently selected from the group consisting of hydrogen atoms and alkyl groups having from 1 to 3 carbon atoms; cyano groups; sulfamoyl groups; ureido groups; sulfo groups; halogen atoms; alkoxy groups having from 1 to 3 carbon atoms; alkoxycarbonyl groups having from 2 to 4 carbon atoms; alkanoyl groups having from 1 to 3 carbon atoms; alkanoylamino groups having from 1 to 3 carbon atoms; alkanoyloxy groups having from 1 to 3 carbon atoms; alkylthio groups having from 1 to 3 carbon atoms; alkylsulfinyl groups having from 1 to 3 carbon atoms and alkylsulfonyl groups having from 1 to 3 carbon atoms; and substituents (d$^j$):

hydroxy groups; carboxy groups; carbamoyl groups; and carbamoyloxy groups.

6. The compound of claim 1, wherein:

A is a fully saturated heterocyclic group having from 4 to 6 ring atoms, of which one is a nitrogen atom and the remainder are carbon atoms, said nitrogen atom having on its remaining valence a group or atom $R^4$, wherein:

$R^4$ is a hydrogen atom; an alkyl group having from 1 to 4 carbon atoms; an substituted alkyl group which has from 1 to 4 carbon atoms and which has at least one substituent selected from the group consisting of substituents (a$^{ii}$), defined below; or a group of formula —C(=NH)R$^5$, wherein $R^5$ is a hydrogen atom or an alkyl group having from 1 to 4 carbon atoms;

substituents (a$^{ii}$):

hydroxy groups, carboxy groups, carbamoyl groups, cyano groups, halogen atoms, and groups of formula —NR$^{a'}$R$^{b'}$, where R$^{a'}$ and R$^{b'}$ are independently selected from the group consisting of hydrogen atoms and alkyl groups having from 1 to 3 carbon atoms.

7. The compound of claim 1, wherein:

$R^2$ is a hydrogen atom; and

Q is a group of formula —B—N+R$^8$R$^9$R$^{10}$, wherein:

$R^8$, $R^9$ and $R^{10}$ are independently selected from the group consisting of alkyl groups having 1 to 3 carbon atoms and substituted alkyl groups which have from 1 to 3 carbon atoms and which have at least one substituent selected from the group consisting of substituents (b$^{ii}$), defined below; and B is an alkylene or alkylidene group having from 1 to 3 carbon atoms;

substituents (b$^{ii}$):

hydroxy groups; carboxy groups; groups of formula —NR$^{a''}$R$^{b''}$, where R$^{a''}$ and R$^{b''}$ are independently selected from the group consisting of hydrogen atoms and alkyl groups having from 1 to 3 carbon atoms; groups of formula —CONR$^{a''}$R$^{b''}$, where R$^{a''}$ and R$^{b''}$ are as defined above; cyano groups; sulfamoyl group; ureido groups; sulfo groups; halogen atoms; alkoxy groups having from 1 to 3 carbon atoms; alkoxycarbonyl groups having from 2 to 4 carbon atoms; alkanoyl groups having from 2 to 3 carbon atoms; alkanoylamino groups having from 2 to 3 carbon atoms; alkanoyloxy groups having from 2 to 3 carbon atoms; alkylthio groups having from 1 to 3 carbon atoms; alkylsulfinyl groups having from 1 to 3 carbon atoms and alkylsulfonyl groups having from 1 to 3 carbon atoms.

8. The compound of claim 1, wherein A is a fully saturated heterocyclic group having 5 ring atoms, of which one is a nitrogen atom and the remainder are carbon atoms, said nitrogen atom having on its remaining valence a group or atom R$^4$, wherein:

R$^4$ is a hydrogen atom; a methyl group; an ethyl group; or a substituted methyl or ethyl group which has at least one substituent selected from the group consisting of hydroxy groups, carbamoyl groups and halogen atoms.

9. A pharmaceutical composition for the treatment or prophylaxis of bacterial infections in a patient in need thereof, which composition comprises an effective amount of an antibacterial agent in admixture with a pharmaceutically acceptable carrier or diluent, wherein the antibacterial agent is selected from the group consisting of compounds of formula (I) and pharmaceutically acceptable salts and esters thereof, as defined in claim 1.

10. The composition of claim 1, wherein A is a fully saturated heterocyclic group having 5 ring atoms, of which one is a nitrogen atom and the remainder are carbon atoms, said nitrogen atom having on its remaining valence a group or atom R$^4$, wherein:

R$^4$ is a hydrogen atom; a methyl group; an ethyl group; or a substituted methyl or ethyl group which has at least one substituent selected from the group consisting of hydroxy groups, carbamoyl groups and halogen atoms.

11. A method for the treatment or prophylaxis of bacterial infections in an animal patient in need thereof, which method comprises administering to said animal an effective amount of an antibacterial agent in admixture with a pharmaceutically acceptable carrier or diluent, wherein the antibacterial agent is selected from the group consisting of compounds of formula (I) and pharmaceutically acceptable salts and esters thereof, as defined in claim 1.

12. The method of claim 11, wherein A is a fully saturated heterocyclic group having 5 ring atoms, of which one is a nitrogen atom and the remainder are carbon atoms, said nitrogen atom having on its remaining valence a group or atom R$^4$, wherein:

R$^4$ is a hydrogen atom; a methyl group; an ethyl group; or a substituted methyl or ethyl group which has at least one substituent selected from the group consisting of hydroxy groups, carbamoyl groups and halogen atoms.

* * * * *